United States Patent [19]

Brenner et al.

[11] Patent Number: 5,024,940

[45] Date of Patent: Jun. 18, 1991

[54] NUCLEIC ACIDS ENCODING THE DELTA CHAIN OF THE T CELL ANTIGEN RECEPTOR

[75] Inventors: Michael B. Brenner, Ashland; Jack L. Strominger, Lexington; Jonathan Seidman, Milton; Stephen H. Ip, Framingham; Michael S. Krangel, Newtonville, all of Mass.

[73] Assignees: T Cell Sciences, Inc., Cambridge; Dana-Farber Cancer Institute, Boston; President & Fellows of Harvard College, Cambridge, all of Mass.

[21] Appl. No.: 115,256

[22] Filed: Oct. 29, 1987

Related U.S. Application Data

[63] Continuation-in-part of Ser. No. 16,252, Feb. 19, 1987, which is a continuation-in-part of Ser. No. 882,100, Jul. 3, 1986, abandoned.

[51] Int. Cl.[5] .............................................. C12N 15/12

[52] U.S. Cl. ................................ 435/69.1; 435/172.3; 530/387; 536/27

[58] Field of Search ...................... 536/27; 435/68, 70, 435/172.3, 69.1

[56] References Cited

U.S. PATENT DOCUMENTS

| | | | |
|---|---|---|---|
| 4,444,744 | 4/1984 | Goldberg | 421/1.1 |
| 4,550,086 | 10/1985 | Reinherz | 436/508 |
| 4,713,332 | 12/1987 | Mak | 435/70 |
| 4,874,845 | 10/1989 | Saito et al. | 530/395 |

OTHER PUBLICATIONS

Van Den Elsen, P. et al., May 1986, PNAS U.S.A., 83:2944-2948.

Chien, Y-L. et al., Jun. 25, 1987, Nature 327: 677-682.

Hata, S. et al., Oct. 30, 1987, Science 238: 678-682.

Bond, H. et al., Oct. 30, 1987, Science 238: 682-684.

Van Den Elsen, P. et al., Nov. 29, 1984, Nature 312: 413-418.

Krissansen, G. W., 1986, Embo J. 5(8), 1799-1808.

Tunnacliffe et al., EMBO J. 5: 1245-1252 (1986).

LeFranc et al., Cell 45: 237-246 (1986).

Royer et al., J. Exp. Med. 160: 947-952 (1984).

Kyte and Doolittle, J. Mol. Biol. 157: 105-132 (1982).

Hopp and Woods, Proc. Natl. Acad. Sci., U.S.A., 78: 3824-3828 (1981).

Cochran et al., Proc. Natl. Acad. Sci., U.S.A., 82: 19-23.

Haj-Amad and Graham, 1986, J. Virol., 57: 267-276.

Mansour et al., 1985, Proc. Natl. Acad. Sci., U.S.A., 82: 1359-1363.

Subramani and Southern, 1983, Anal. Biochem., 135: 1-15.

Kaufman and Sharp, 1982, J. Mol. Biol. 159: 601-621.

Kuroda et al., 1986, EMBO J., 5: 1359-1365.

Maeda et al., 1985, Nature (London), 315: 592-594.

(List continued on next page.)

*Primary Examiner*—Richard A. Schwartz
*Assistant Examiner*—John D. Ulm
*Attorney, Agent, or Firm*—Pennie & Edmonds

[57] ABSTRACT

The present invention provides purified polypeptides which comprises at least a portion of a a δT cell receptor polypeptide, a γT cell receptor polypeptide, a γδT cell receptor complex or a γδT cell receptor complex. Substances capable of forming complexes with these polypeptides are also provided.

Additonally, methods for detecting T cells which have within them or on their surfaces a polypeptide of the present invention are provided. Moreover, methods for diagnosing immune system abnormalities are provided which comprise measuring in a sample from a subject the number of T cells which have within them or on their surfaces a polypeptide of the present invention.

47 Claims, 37 Drawing Sheets

OTHER PUBLICATIONS

Kramer et al., 1986, Science, 231: 1580–1584.
Valenzuela et al., 1982, Nature (London), 298: 347.
Melton et al., 1984, Nucl. Acids Res., 12: 7035–7056.
Peden, 1983, Gene, 22: 277.
Young and Davis, 1983, Proc. Natl. Acad. Sci., U.S.A., 80: 1194–1198.
Pardoll et al., Faseb J., 1: 103–109 (1987).
Reilly et al., Nature, 321: 878–880 (Jun. 1986).
Haars et al., J. Exp. Med., 164: 1–24 (Jul. 1986).
Moingeon et al., Nature, 323: 638–640 (Oct. 1986).
Jones et al., Nature, 323: 635–638 (Oct. 1986).
Lanier and Weiss, Nature, 324: 268 (1986).
LeFranc et al., Proc. Natl. Acad. Sci., U.S.A., 83: 9596–9600 (1986).
European Patent Application Pub. No. 200,350, published Nov. 5, 1986.
MacLeod et al., Proc. Natl. Acad. Sci., U.S.A., 83: 6989–6993 (1986).
Brenner et al., Nature (London), 322: 145–149 (1986).

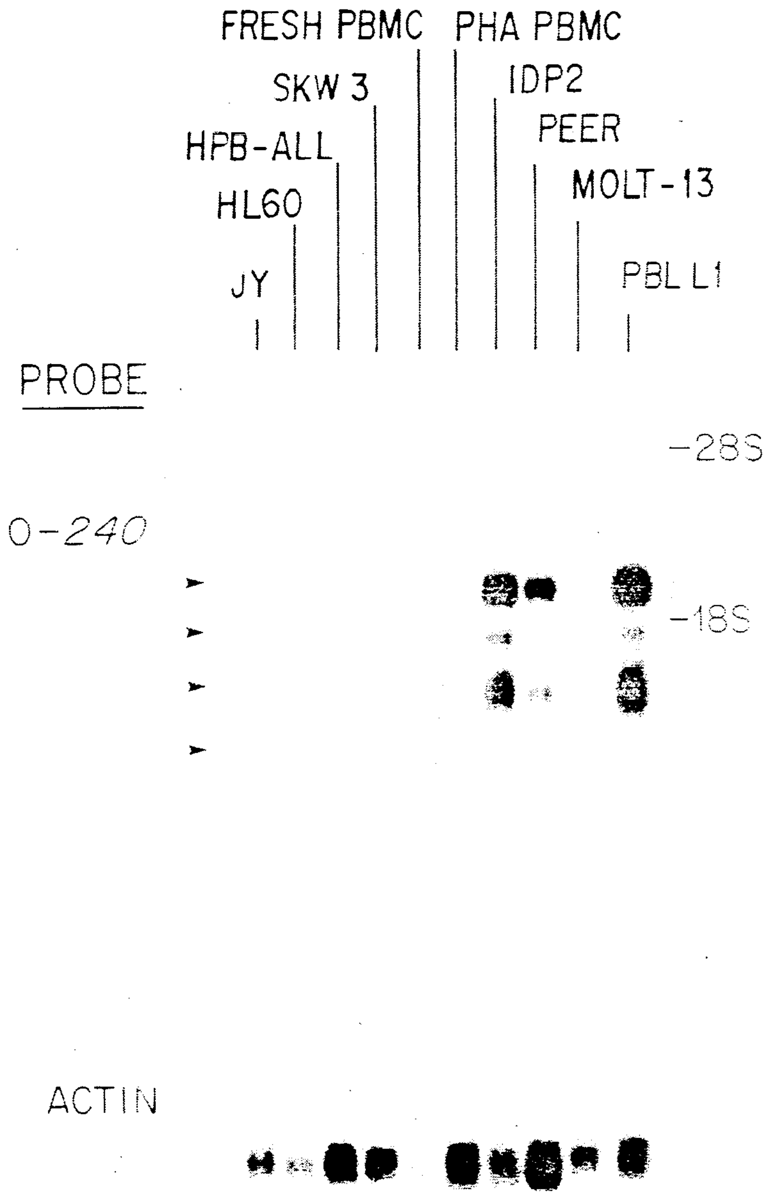
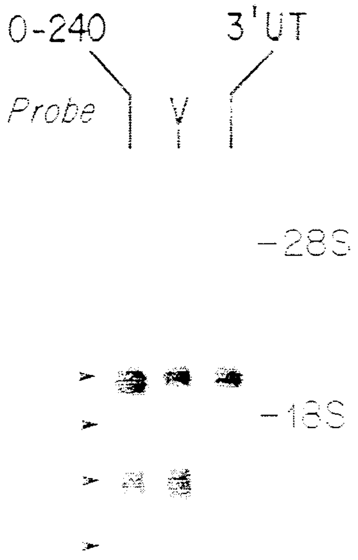
FIG. 12B
FIG. 12A

FIG. 15

```
                                  -10                              L   -1  +1    V                        10
Group O          C   V   F   V   A   F   S   Y   S   G   S   S   V   A   Q   K   V   T   Q   A   Q   S   S   V   S   M
Composite:     G TGT GTA TTT GTG GCC TTC AGC TAC TCT GGA TCA AGT GTG GCC CAG AAG GTT ACT CAA GCC CAG TCA TCA GTA TCC ATG
DN-4:                                                          - --T --- -CA --G T-- --G C-T --- AAG AA- AAG --T G--

                               20                                          30                                      40
 P   V   R   K   A   V   T   L   N   C   L   Y   E   T   S   W   W   S   Y   Y   I   F   W   Y   K   Q   L   P   S   K
CCA GTG AGG AAA GCA GTC ACC CTG AAC TGC CTG TAT GAA ACA AGT TGG TGG TCA TAT TAT ATT TTT TGG TAC AAG CAA CTT CCC AGC AAA
-AG --- GCA G-- T-- -CA --- --- G-- --- ACC --- --C --- --- GAT ACT AAT --C CTC T-G --C --- --- --A --G -AA *** G-A GGG

                               50                                              60                                  70
 E   M   I   F   L   I   R   Q   G   S   D   E   Q       N   A   K   S   G   R   Y   S   V   N   F   K   K   A   A   K
GAG ATG ATT TTC CTT ATT CGC CAG GGT TCT GAT GAA CAG *** AAT GCA AAA AGT GGT CGC TAT TCT GTC AAC TTC AAG AAA GCA GCG AAA
C-- G-- -C- C-- G-C --- -T- --A -AA G-A T-C A-G --- TAT --- --- -CG TTA AAC --- -TC --- --G --- --- C-- --- --- --T --G

                               80                                          90    V                                 100
 S   V   A   L   T   I   S   A   L   Q   L   E   D   S   A   K   Y   F   C   A   L   A   V   R   G   K   L   L   E   R
TCC GTC GCC TTA ACC ATT TCA GCC TTA CAG CTA GAA GAT TCA GCA AAG TAC TTT TGT GCT CTT GCT GTA CGG GGA AAA CTC CTA GAA AGG
--- T-- AG- C-G GAG --C --C -A- -CG --- --G -GG --- G-T --G -C- --T --C --- --- --C ATG -AG --- -AT *** *** A-C -G- G--

                          110                                  J   120                                C          130
 N   G   G   Y   A   V   F   P   S   D   K   L   I   F   G   K   G   T   R   V   T   V   E   P   R   S   Q   P   H   T
AAT GGG GGA TAC GCG GTC TTT CCA TCC GAT AAA CTC ATC TTT GGA AAA GGA ACC CGT GTG ACT GTG GAA CCA AGA AGT CAG CCT CAT ACC
-CG C-A *** *** *** *** *** G-T A-- --C --- --- G-- --- --- C-- --- --- -AA --- --- --- --- --- -A- --C --- --- -CG G--

                          140                                      150                                         160
 K   P   S   V   F   V   M   K   N   G   T   N   V   A   C   L   V   K   E   F   Y   P   K   D   I   R   I   N   L   V
AAA CCA TCC GTT TTT GTC ATG AAA AAT GGA ACA AAT GTC GCT TGT CTG GTG AAG GAA TTC TAC CCC AAG GAT ATA AGA ATA AAT CTC GTG
--- --- --T --- --C A-- --- --- --- --- --- --- --T --- --- --- --- --A --T --- --- --T --A --G G-G -CT --- -GC --- AGA

                          170                                      180                                         190
 S   S   K   K   I   T   E   F   D   P   A   I   V   I   S   P   S   G   K   Y   N   A   V   K   L   G   K   Y   E   D
TCA TCC AAG AAG ATA ACA GAG TTT GAT CCT GCT ATT GTC ATC TCT CCC AGT GGG AAG TAC AAT GCT GTC AAG CTT GGT AAA TAT GAA GAT
--- --- --- --- --T GTG --A --C --C --- --- --A --- --- --C --- --C --- --- --- -G- --- --- --- --- --- C-G --- -G- ---
```

FIG. 15 (cont.)

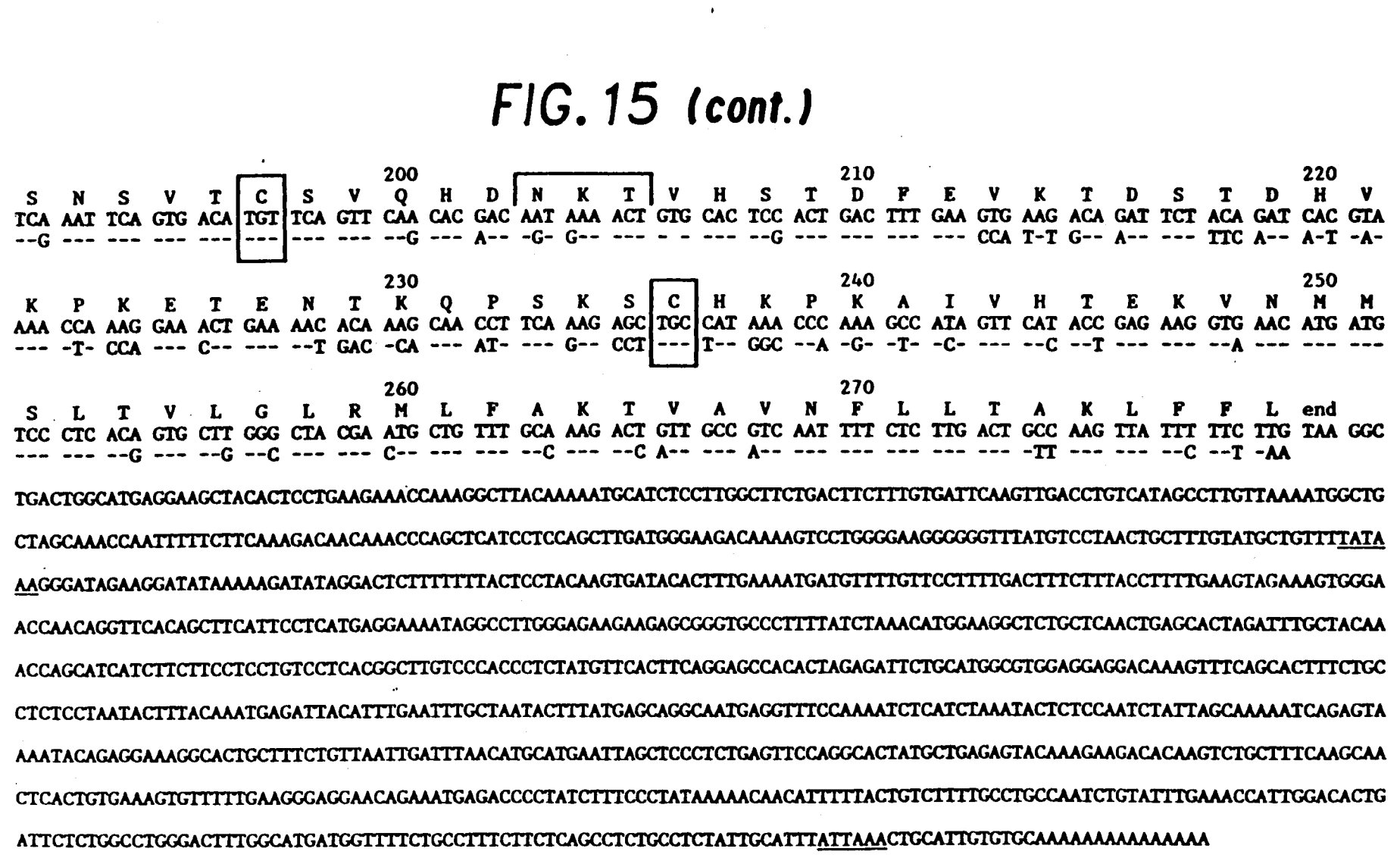

```
                                200                                          210                                                            220
 S   N   S   V   T   C   S   V   Q   H   D   N   K   T   V   H   S   T   D   F   E   V   K   T   D   S   T   D   H   V
TCA AAT TCA GTG ACA TGT TCA GTT CAA CAC GAC AAT AAA ACT GTG CAC TCC ACT GAC TTT GAA GTG AAG ACA GAT TCT ACA GAT CAC GTA
--G --- --- --- --- --- --- --- --G --- A-- -G- G-- --- - - --- --G --- --- --- --- CCA T-T G-- A-- --- TTC A-- A-T -A-

                                230                                          240                                                            250
 K   P   K   E   T   E   N   T   K   Q   P   S   K   S   C   H   K   P   K   A   I   V   H   T   E   K   V   N   M   M
AAA CCA AAG GAA ACT GAA AAC ACA AAG CAA CCT TCA AAG AGC TGC CAT AAA CCC AAA GCC ATA GTT CAT ACC GAG AAG GTG AAC ATG ATG
--- -T- CCA --- C-- --- --T GAC -CA --- AT- --- G-- CCT --- T-- GGC --A -G- -T- -C- --- --C --T --- --- --A --- --- ---

                                260                                          270
 S   L   T   V   L   G   L   R   M   L   F   A   K   T   V   A   V   N   F   L   L   T   A   K   L   F   F   L  end
TCC CTC ACA GTG CTT GGG CTA CGA ATG CTG TTT GCA AAG ACT GTT GCC GTC AAT TTT CTC TTG ACT GCC AAG TTA TTT TTC TTG TAA GGC
--- --- --G --- --G --C --- --- C-- --- --- --C --- --C A-- --- A-- --- --- --- --- --- -TT --- --- --C --T -AA
```

TGACTGGCATGAGGAAGCTACACTCCTGAAGAAACCAAAGGCTTACAAAAATGCATCTCCTTGGCTTCTGACTTCTTTGTGATTCAAGTTGACCTGTCATAGCCTTGTTAAAATGGCTG

CTAGCAAACCAATTTTTCTTCAAAGACAACAAACCCAGCTCATCCTCCAGCTTGATGGAAGACAAAAGTCCTGGGGAAGGGGGTTTATGTCCTAACTGCTTTGTATGCTGTTTTATA

AAGGGATAGAAGGATATAAAAAGATATAGGACTCTTTTTTTACTCCTACAAGTGATACACTTTGAAAATGATGTTTTGTTCCTTTTGACTTTCTTTACCTTTTGAAGTAGAAAGTGGGA

ACCAACAGGTTCACAGCTTCATTCCTCATGAGGAAAATAGGCCTTGGGAGAAGAAGAGCGGGTGCCCTTTTATCTAAACATGGAAGGCTCTGCTCAACTGAGCACTAGATTTGCTACAA

ACCAGCATCATCTTCTTCCTCCTGTCCTCACGGCTTGTCCCACCCTCTATGTTCACTTCAGGAGCCACACTAGAGATTCTGCATGGCGTGGAGGAGGACAAAGTTTCAGCACTTTCTGC

CTCTCCTAATACTTTACAAATGAGATTACATTTGAATTTGCTAATACTTTATGAGCAGGCAATGAGGTTTCCAAAATCTCATCTAAATACTCTCCAATCTATTAGCAAAAATCAGAGTA

AAATACAGAGGAAAGGCACTGCTTTCTGTTAATTGATTTAACATGCATGAATTAGCTCCCTCTGAGTTCCAGGCACTATGCTGAGAGTACAAAGAAGACACAAGTCTGCTTTCAAGCAA

CTCACTGTGAAAGTGTTTTTGAAGGGAGGAACAGAAATGAGACCCCTATCTTTCCCTATAAAAACAACATTTTTACTGTCTTTTGCCTGCCAATCTGTATTTGAAACCATTGGACACTG

ATTCTCTGGCCTGGGACTTTGGCATGATGGTTTTCTGCCTTTCTTCTCAGCCTCTGCCTCTATTGCATTTATTAAACTGCATTGTGTGCAAAAAAAAAAAAAAA

```

  - - - - - - - - - - - - - - - - - - - - - - - - - - - - - - - - - - - - - - - - - - - - - -
```

NUCLEIC ACIDS ENCODING THE DELTA CHAIN OF THE T CELL ANTIGEN RECEPTOR

This invention was supported by NIH Grants, and the Government has certain rights in the invention.

BACKGROUND OF THE INVENTION

This application is a continuation-in-part of U.S. Ser. No. 016,252, filed Feb. 19, 1987, which is a continuation-in-part of U.S. Ser. No. 882,100, filed July 3, 1986, now abandoned, the contents of which are hereby incorporated by reference into the present application.

Within this application several publications are referenced by Arabic numerals within parentheses. Full citations for these references may be found at the end of the specification immediately preceding the claims. The disclosures of these publications in their entirety are hereby incorporated by reference into this application in order to more fully describe the state of the art to which this invention pertains.

Understanding T cell recognition of antigen and the restriction of the process by major histocompatibility complex (MHC) encoded antigens has been an important goal in immunology. A major step forward occurred with the immunochemical identification of clone specific disulfide-linked heterodimers on T cells, composed of subunits termed T cell antigen receptors (TCR) $\alpha$ and $\beta$. The TCR $\alpha$ and $\beta$ subunits have a relative molecular mass ($M_r$) of approximately 50,000 and 40,000 daltons, respectively (1, 2, 3). Genes that rearrange during T cell ontogeny and encode the TCR$\beta$ (4, 5) and TCR$\alpha$ (6, 7, 8) subunits were isolated either by subtractive hybridization or by probing with oligonucleotides.

A unique feature of the human TCR $\alpha$, $\beta$ was the observed comodulation (2), coimmunoprecipitation (9, 10) and required coexpression (11) of the TCR $\alpha$, $\beta$ molecules with the T3 glycoprotein, which suggested that these two structures were related. Subsequently, the direct physical association of the two protein complexes was demonstrated by chemically cross-linking the TCR $\alpha$, $\beta$ molecules to the T3 glycoprotein and identifying the components of the cross-linked complex as the TCR subunit and the T3 glycoprotein ($M_r$ 28,000) subunit (12). A T3 counterpart is similarly associated with murine TCR $\alpha$, $\beta$ (13, 14).

A third gene that rearranges in T cells, designated TCR $\gamma$, has been identified in mouse (15, 16, 17) and in man (18, 19). However, there are major differences between the human and mouse TCR $\gamma$ gene in terms of its genetic structure; for example, the cDNA of the human TCR $\gamma$ gene indicates five potential sites for N-linked glycosylation in the TCR $\gamma$ gene product, which contrasts with the notable absence of such sites in the murine TCR $\gamma$ gene. Thus, the human TCR $\gamma$ gene product will have a high molecular weight which is not predictable from its genetic sequence.

The TCR $\gamma$ gene rearrangements occur in lymphocytes with suppressor-cytotoxic as well as helper phenotypes and may produce a large number of TCR $\gamma$ chains (18, 19, 20, 21, 22, 23). However, the function of the TCR $\gamma$ gene is unknown. Furthermore, neither the protein encoded by the TCR $\gamma$ gene nor its possible association with other structures (as occurs with TCR $\alpha$, $\beta$ and T3 glycoproteins) have been defined. In humans, the multiple glycosylation sites render it impossible to predict with accuracy the nature and size of the TCR $\gamma$ polypeptide structure. Additionally, the published literature does not teach or suggest the utility of TCR $\gamma$ with regard to diagnosing, monitoring or staging human diseases.

It appears increasingly likely that the TCR $\alpha$, $\beta$ molecule alone determines both antigen recognition and MHC restriction on at least some T cells (24, 25). However, it is not clear that TCR $\alpha$, $\beta$ accounts for the process of T cell selection during T cell ontogeny or for all antigen specific recognition by mature T cells. For example, suppressor T lymphocytes remain an enigma; in some cases they delete or fail to rearrange TCR genes (26,27). Thus, it is of great importance to determine if a second T cell receptor exists, to define its structure (particularly with regard to the possible use of the TCR $\gamma$ gene product) and ultimately to understand what function or functions it serves.

SUMMARY OF THE INVENTION

The present invention provides a purified polypeptide which comprises at least a portion of a $\delta$ T cell receptor polypeptide. Additionally, a substance capable of specifically forming a complex with at least one $\delta$ T cell receptor polypeptide is provided.

Also provided is a method for detecting T cells, each of which has a $\delta$ T cell receptor polypeptide. This method comprises contacting a sample which contains T cells with substances capable of forming complexes with $\delta$ T cell receptor polypeptides so as to form cellular complexes between the substances and the $\delta$ T cell receptor polypeptides. These cellular complexes are detected and thereby T cells, each of which has a $\delta$ T cell receptor polypeptide, are detected.

The invention further provides a method for diagnosing an immune system abnormality in a subject. This method comprises determining the number of T cells in a sample from the subject and contacting the sample with substances capable of forming complexes with at least one $\delta$ T cell receptor polypeptide so as to form cellular complexes between the substances and the $\delta$ T cell receptor polypeptides. The percentage of T cells in the sample which have a $\delta$ T cell receptor polypeptide is determined and compared with the percentage of T cells which have a $\delta$ T cell receptor polypeptide in a sample from a normal subject who does not have the immune system abnormality. A difference in the percentage of T cells so determined would be indicative of the immune system abnormality.

A further method for diagnosing an immune system abnormality in a subject is provided by the present invention. This method comprises determining the number of $\delta$ T cell receptor polypeptide bearing T cells in a sample from the subject and determining the amount of $\delta$ T cell receptor polypeptides in the $\delta$ T cell receptor bearing T cells. The amount of $\delta$ T cell receptor polypeptides so determined is compared with the amount of $\delta$ T cell receptor polypeptides in an equal number of $\delta$ T cell receptor polypeptide bearing T cells in a sample from a normal subject who does not have the immune system abnormality. A difference in the amount so determined would be indicative of the immune system abnormality.

A further method for diagnosing an immune system abnormality in a subject is provided. This method comprises determining in a sample from the subject the number of T cells which have a $\delta$ T cell receptor polypeptide and the number of T cells consisting of the group of T cells which have one of the surface markers T4, T8 and $\alpha$, $\beta$ T cell receptor. The numbers of T cells so determined are compared with the number of T cells which have a $\delta$ T cell receptor polypeptide and the number of T cells in the group which have the same surface marker as the group of T cells determined in the sample from the subject, in a sample from a subject who does not have the immune system abnormality. A difference in the number of T cells so determined which have a $\delta$ T cell receptor polypeptide relative to the number of T cells in the group so determined would be indicative of the immune system abnormality.

The present invention also provides a purified polypeptide which comprises at least a portion of a T cell receptor polypeptide. Additionally, a substance capable of specifically forming a complex with at least one $\gamma$ T cell receptor polypeptide is provided Furthermore, a method for detecting T cells, each of which has a $\gamma$ T cell receptor polypeptide is provided. This method comprises contacting a sample which contains T cells with substances capable of forming complexes with $\gamma$ T cell receptor polypeptides so as to form cellular complexes between the substances and the $\gamma$ T cell receptor polypeptides. These cellular complexes are detected and thereby T cells, each of which has a $\gamma$ T cell receptor polypeptide, are detected.

A further method for diagnosing an immune system abnormality in a subject is provided by the present invention This method comprises determining the number of T cells in a sample from the subject and contacting the sample with substances capable of forming complexes with at least one $\gamma$ T cell receptor polypeptide so as to form cellular complexes between the substances and the $\gamma$ T cell receptor polypeptides. The percentage of T cells in the sample which have a $\gamma$ T cell receptor polypeptide is determined and compared with the percentage of T cells which have a $\gamma$ T cell receptor polypeptide in a sample from a normal subject who does not have the immune system abnormality. A difference in the percentage of T cells so determined would be indicative of the immune system abnormality.

Still another method for diagnosing an immune system abnormality is provided. This method comprises determining the number of $\gamma$ T cell receptor polypeptide bearing T cells in sample from the subject and the amount of $\gamma$ T cell receptor polypeptides in the $\gamma$ T cell receptor polypeptide bearing T cells. The amount of $\gamma$ T cell receptor polypeptides so determined is compared with the amount of $\gamma$ T cell receptor polypeptides in an equal number of $\gamma$ T cell receptor polypeptide bearing T cells in a sample from a normal subject who does not have the immune system abnormality. A difference in the amount so determined would be indicative of the immune system abnormality.

. Yet another method is provided by the present invention for diagnosing an immune system abnormality in a subject. This method comprises determining in a sample from the subject the number of T cells which have a $\gamma$ T cell receptor polypeptide and the number of T cells consisting of the group of T cells which have one of the surface markers T4, T8 and $\alpha$, $\beta$ T cell receptor. The numbers of T cells so determined are compared with the number of T cells which have a $\gamma$ T cell receptor polypeptide and the number of T cells in the group which have the same surface marker as the group of T cells determined in the sample from the subject, in a sample a from a subject who does not have the immune system abnormality A difference in the number of T cells so determined which have a $\gamma$ T cell receptor polypeptide relative to the number of T cells in the group so determined would be indicative of the immune system abnormality.

The invention further provides a purified complex which comprises at least a portion of a $\delta$ T cell receptor polypeptide and at least a portion of a $\gamma$ T cell receptor polypeptide. Also provided are substances capable of specifically forming a complex with at least one $\gamma$, $\delta$ T cell receptor complex. Moreover, a method for detecting T cells, each of which has a $\gamma$, $\delta$ T cell receptor complex, is provided. This method comprises contacting a sample which contains T cells with substances capable of forming complexes with $\gamma$, $\delta$ T cell receptor complexes so as to form cellular complexes between the substances and the $\gamma$, $\delta$ T cell receptor complexes. These cellular complexes are detected and thereby T cells, each of which has a $\gamma$, $\delta$ T cell receptor complex, are detected.

Still further, the present invention provides another method for diagnosing an immune system abnormality in a subject. This method comprises determining the number of T cells in a sample from the subject and contacting the sample with substances capable of forming complexes with at least one $\gamma$, $\delta$ T cell receptor complex so as to form cellular complexes between the substances and the $\gamma$, $\delta$ T cell receptor complexes. The percentage of T cells which have a $\gamma$, $\delta$ T cell receptor complex is determined and compared with the percentage of T cells which have a $\gamma$, $\delta$ T cell receptor complex in a sample from a normal subject who does not have the immune system abnormality. A difference in the percentage of T cells so determined would be indicative of the immune system abnormality.

The invention provides yet another method of diagnosing an immune system abnormality in a subject. This method comprises determining the number of $\gamma$, $\delta$ T cell receptor complex bearing T cells in a sample from the subject and the amount of $\gamma$, $\delta$ T cell receptor complexes in the $\gamma$, $\delta$ T cell receptor complex bearing T cells. The amount of $\gamma$, $\delta$ T cell receptor complexes so determined is compared with the amount of $\gamma$, $\delta$ T cell receptor complexes in an equal number of $\gamma$, $\delta$ T cell receptor complex bearing T cells in .a normal subject who does not have the immune system abnormality. A difference in the amount so determined would be indicative of the immune system abnormality.

Yet another method for diagnosing an immune system abnormality is provided by the present invention. This method comprises determining in a sample from the subject the number of T cells which have a $\gamma$, $\delta$ T cell receptor complex and the number of T cells consisting of the group which have one of the surface markers T4, T8 and $\alpha$, $\beta$ T cell receptor complex. The numbers of T cells so determined are compared with the number of T cells which have a $\gamma$, $\delta$ T cell receptor complex and the number of T cells in the group which have the same surface marker as the group of T cells determined in the sample from the subject, in a sample from a subject who does not have the immune system abnormality. A difference in the number of T cells so determined which have a $\gamma$, $\delta$ T cell receptor complex relative to the number of T cells in the group would be indicative of the immune system abnormality.

Figure 1A:
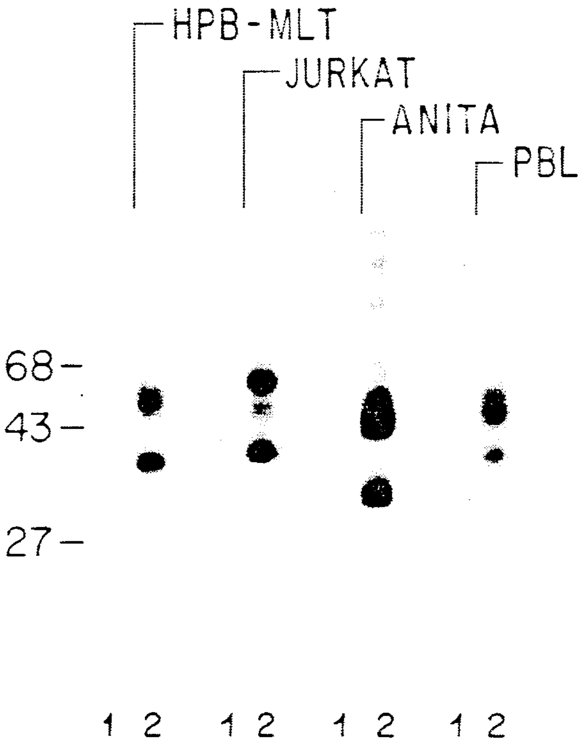
FIG. 1: Reactivity of framework monoclonal antibodies recognizing TCR $\alpha$, $\beta$.

A.

Lane 1: Control antibody, normal mouse serum.

Lane 2: Anti-framework TCR α, β monoclonal antibody (βF1).

B.

Lane 1: Control antibody, normal mouse serum.

Lane 2: Anti-T3 monoclonal antibody (UCHT-1).

Lane 3: Anti-framework TCR α, β monoclonal antibody (WT31).

C. Three dimensional display of flow cytometry analysis of normal adult peripheral blood lymphocytes. Red and green fluorescence were measured compared to non-specific control FITC- and biotin- conjugated monoclonal antibodies. Cells unreactive with either monoclonal antibody were non T cells (lower left corner); cells that were double positive, i.e. reacting with both OKT\3 and βF1, make up the large population of lymphocytes in the center region of the grid; cells that were βF1− but OKT\3+ comprise a small but distinct group of lymphocytes (4% of the T3+ cells) observed along the X-axis.

FIG. 2: SDS-PAGE analysis of cell surface T3 and T3-associated (cross-linked) molecules by immunoprecipitation from IDP1 and IDP2 cell lines.

A. IDP1 cell line 2 (WT31+) and cell line 3 (WT31−).

Lanes 1, 2, 7, 8 : Normal mouse serum.

Lanes 3, 4, 9, 10: Anti-T3 monoclonal antibody (UCHT-1).

Lanes 5, 6, 11, 12: Anti-framework TCR α, β monoclonal antibody (F1).

B. IDP2 cell line 7 (88% WT31−T3+)

Lanes 1, 4, 7, 10: Normal mouse serum.

Lanes 2, 5, 8, 11: Anti-framework TCR monoclonal antibody (βF1 ).

Lanes 3, 6, 9, 12: Anti-T3 monoclonal antibody (UCHT-1).

$^{125}$I-labeled samples XL-cross-linked with DSP.

C. IDP2 cell line 5 (WT31+ T3+) and cell line 7 (88% WT31−T3+).

Lanes 1, 3: Normal mouse serum.

Lanes 2, 4: Anti-T3 monoclonal antibody (UCHT-1).

FIG. 3 Northern blot analysis of RNA isolated from IDP2 cell lines using TCR α, TCR βand TCR γ cDNA probes.

A.

Lane 1 IDP2 cell line 6 (WT31−) p1 Lane 2: T leukemic cell line HBP-MLT.

B.

Lane 1 : IDP2 cell line 5 (WT31+T3+).

Lane 2: IDP2 cell line 7 (88% WT31−T3+).

Lane 3: Cell line HPB-MLT.

FIG. 4: Anti-V γ and anti-C γ peptide sera immunoprecipitations from IDP2 cell line 7.

A.

Lane 1: Normal mouse serum.

Lane 2: Anti-V γ peptide mouse serum.

Lane 3: Normal rabbit serum.

Lane 4: Anti-C γ peptide rabbit serum.

B.

Lane 1: Normal mouse serum.

Lane 2: Anti-T3 monoclonal antibody (UCHT-1).

Lane 3: Normal rabbit serum.

Lane 4, 5: Anti-C γ peptide rabbit serum.

FIG. 5 Immunoprecipitations of TCR γ, δ and T3 from a human tumor and peripheral blood lymphocyte lines.

Immunoprecipitations from $^{125}$I-labelled cell lysates were analyzed by SDS-PAGE (10% acrylamide) under reducing (R) or nonreducing (N or NR) conditions. Size markers, $M_r$ in thousands.

A. TCR, γ, δ and T3 subunits on IDP2 and PEER cells Immunoprecipitations were performed using 1 μg control mAb P3 (mAb secreted by the P3X63.Ag8 myeloma lanes 1, 3, 5 and 6): 1 μg UCHT1 (anti-T3) (40) (lanes 2, 4, 7 and 8); 10 μl normal rabbit serum (NRS 25 lane 9) and 10 μl anti-C peptide sera (anti-TCR γ) (lane 10). Arrows indicate positions of TCR γ subunits which change mobility under R and NR conditions.

B. TCR γ, δ and T3 subunit on peripheral blood T cell clone, PBL C1 and the WT31−PBL LINE. Immunoprecipitations were performed using control mAb P3 (lanes 1, 4, 9 and 12), 1 μg βF1 (anti-TCR β) (lanes 2,5, 10 and 13). NRS (lanes 7 and 15) and anti-C peptide sera (lanes 8 and 16). Open arrow indicates disulphide-linked βF1 and unreactive T3-associated species; solid arrow indicates non-disulphide-linked, T3-associated material that displays increased SDS-PAGE mobility under nonreducing conditions (like TCR δ in A).

Figure 6:
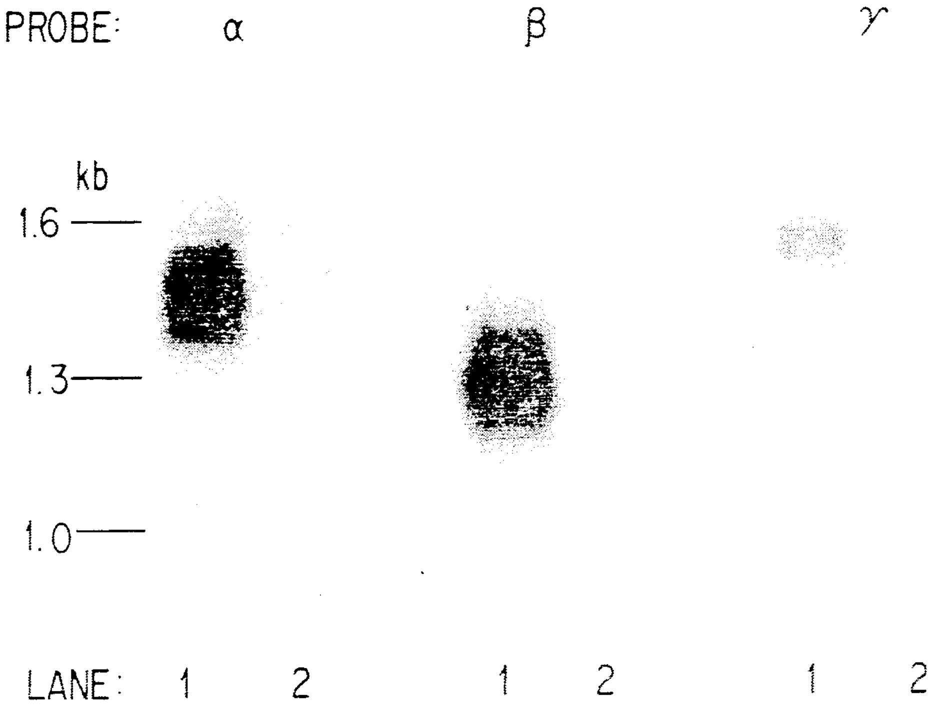

FIG. 6 Northern blot analysis of RNA isolated from PBL C1.

Total RNA preparations from the T leukemic cell line HPB-MLT (lane 1 for each probe and PBL C1 (lane for each probe) were analyzed on Northern Blots using TCR α, TCR β and TCR γ cDNA probes.

FIG. 7 Two-dimensional gel analysis of TCR γ polypeptides and precursors.

Panels A–D Comparison of reduced (separated) and nonreduced (dimeric) T3-associated polypeptides from PBL C1 cells were lysed in CHAPS and immunoprecipitated with anti-T3 mAb. Two-dimensional gel electrophoresis was carried out under reducing conditions (A,C) or nonreducing conditions (B,D). The T3 γ, δ and ε positions are labeled and focused to similar positions under both R and N conditions. After cleaving the disulphide bond, the T3 associated polypeptides (40K and 36K) migrated to focusing positions close to T3 γ R conditions, but shifted to a more acidic position (close to T3 δ) under N conditions (when both components of the dimer were present (68K)). Size markers, $M_r$.

Panels E–H Analysis of glycosylated and non-glycosylated IDP2 and PBL C1 TCR peptide precursors. IDP2 and PBL C1 cells were pulse-labelled with $^{35}$S-methionine, lysed under denaturing conditions and immunoprecipitated with anti-C γ peptide sera. Immunoprecipitations were then either treated and with endo-H or mock treated and analyzed by two-dimensional gel electrophoresis. Glycosylated TCR γ peptides are denoted by open arrows, and nonglycosylated TCR γ peptides by solid arrows. Apparent relative molecular masses were calculated from migration of standards used in panels A and B (not shown). A small amount of contaminating actin, denoted by a diamond in each panel, served as an internal marker. E, IDP2 TCR γ, mock incubated; F, IDP2 TCR γ, endo H treated; G, PBL C1 TCR γ mock incubated; H, PBL C1 TCR γ endo-H treated.

FIG. 8 Rearrangement of the γ and β genes in T cells expressing the TCR γ polypeptide.

Genomic DNAs isolated from the IDP2 cell line, PBL C1, PBL C2, WT31− PBL LINE, fetal thymus, newborn thymus, PBL and a B cell line (JY for germline) were examined in Southern blot analysis for TCR γ (A, B) and TCR β (C) gene rearrangements. Genomic DNAs were digested with BamHI (A, C) or EcoRI (B)

fractionated on agarose gels and transferred to nitrocellulose filters for hybridization with $^{32}P$-labelled $J_{\gamma\ 1,3}$ (A,B) or $C_{\beta 2}$ probes (C). Arrows and roman numerals denote TCR $\gamma$ rearrangements. Size markers in kb.

FIG. 9 Cytolysis by IDP2 and PBL C1 cells

Panels A,C IDP2 or PBL C1 effector cells were incubated (at effector:target, (E:T) ratios indicated) with $^{51}$ Cr-labelled target cells K562 (erythroid line), U937 (monocytic line), MOLT-4, CEM (T leukemic lines), Daudi (Burkitt's lymphoma line) or allergenic or autologous PBL (3-day PHA blasts of human PBL). The % specific release of $^{51}$Cr for each target is shown. The same assays were carried out after prebinding anti-T3 mAb UCHT1 to the effector cells for 30 minutes at 0° C. (+anti-T3).

Panel B. Inhibition of IDP2 cytolysis of MOLT-4 target cells by various mAb. IDP2 and $^{51}$Cr-labelled MOLT-4 cells were incubated together at a 40:1 E:T ratio in the presence of various dilutions of anti-MHC Class 1 mAb W6/32 (anti-HLA-A, B, C monomorphic determinant) (58), anti-HLA-A, B, C (monomorphic determinant) (59), 4E (anti-HLA-B and C locus) (60), 131 (anti-HLA-A locus) (61) or anti-MHC Class II mAb LB3.1 (anti-DR specific)(62), anti-Leu 10 (anti-DQ specific)(63) or anti-T3 mAb UCHT1. Higher dilutions were used for mAb as ascites (W6/32, 4E, 131, LB3.1 and UCHT1) and lower dilutions were used for commercial mAb(anti-Leu 10) or culture supernatant (anti-HLA-A, B, C).

Figure 10:
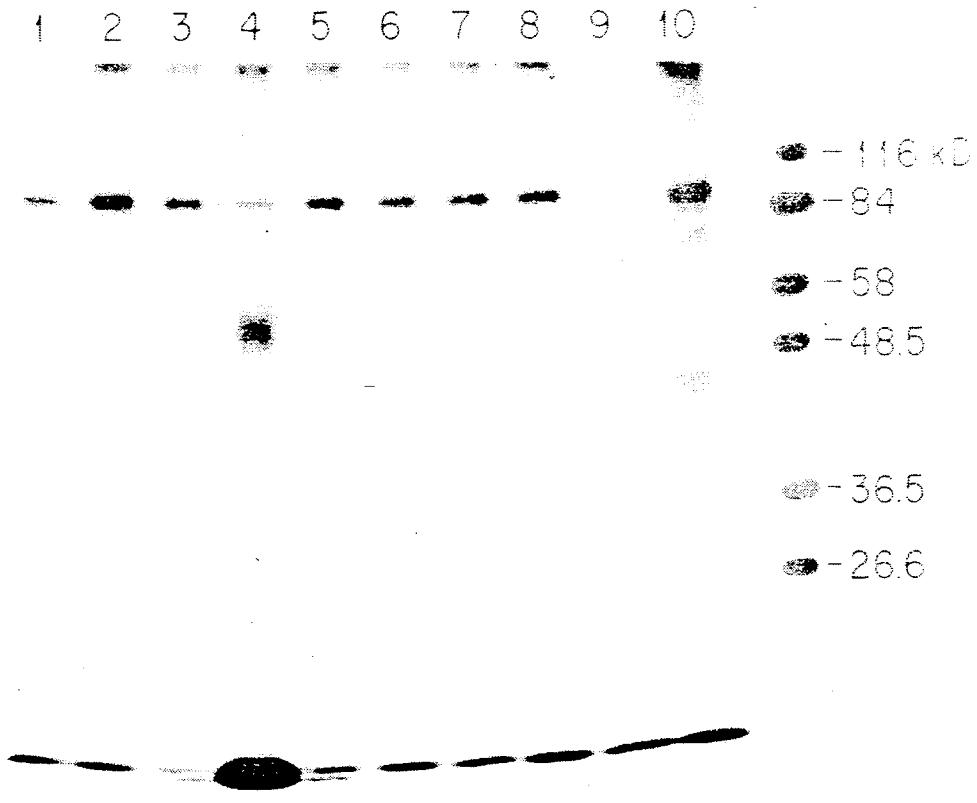

FIG. 10. Immunoprecipitation of a TCR $\gamma$ chain derived from Peer cells

Lanes 1–8 are various hybridoma culture supernatates from the same hybridoma fusion experiment; Lane 4 is anti-$\gamma$ chain monoclonal antibody 34D12; Lane 9 is control P3x63Ag8.653 culture supernate; Lane 10 is control normal mouse serum.

Figure 11:
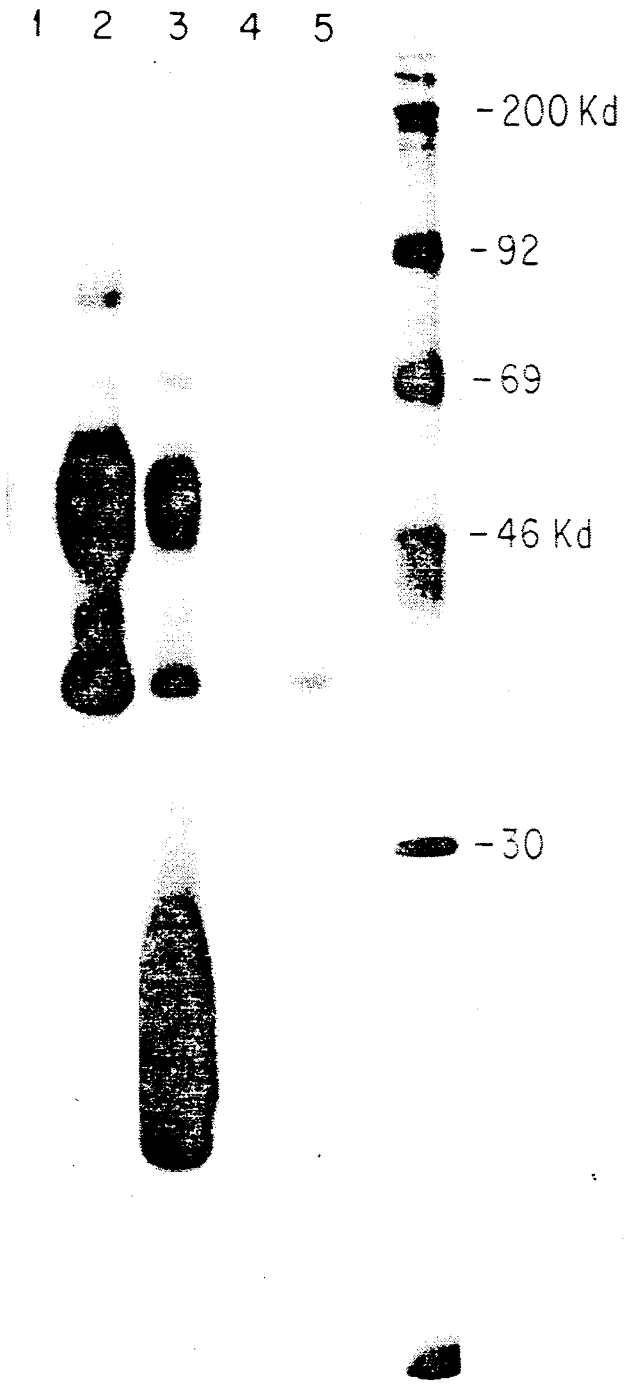

FIG. 11. Immunoprecipitation of a TCR $\delta$ chain derived from IDP2 cells

Lane 1 is control P3x63Ag.8.653 culture supernate; Lanes 2 and 5 are monoclonal antibody 4A1 culture supernatate; Lane 3 is Leu 4; Lane 4 is control normal rabbit serum.

IDP2 cells were $^{125}$I labeled using lactoperoxidase and solublized in 2% Triton X100. In Lanes 4 and 5, this lysate was boiled for 3 minutes in 1% SDS, diluted with 4 volumes of 1% Triton X100 and renatured overnight at 4° C. This resulted in separation of the TCR $\gamma$ and $\delta$ chains. After such chain separation, monoclonal antibody 4A1 specifically immunoprecipitated the TCR $\delta$ chain (Lane 5) as described hereinabove.

FIG. 12A. Northern blot analysis of group O hybridizing transcripts

RNA sources are: JY, B cell line; HL60, myeloid cell line; .HPB-ALL and SKW3, TCR $\alpha\beta$ and surface TCR-T cell lines, respectively; fresh and PHA PBMC, fresh and 2 days PHA activated peripheral blood mononuclear cells; IDP2, PEER, Molt-13 and PBL-L1 (identical to WT31 - PBL Line, ref. 75), TCR $\gamma\delta$ T cell lines. Arrowheads mark the positions of the four major transcripts detected; 18s and 28s rRNA served as markers.

FIG. 12B. Northern blot analysis using IDP2 RNA

IDP2 RNA treated as described in materials and methods was probed with nick-translated 0-240, a 330 bp Eco RI-Sca I fragment of 0-240/38 (V probe; see FIG. 14) labelled by hexanucleotide priming, or a 550 bp Hae III fragment of 0-240 (3′ UT; see FIG. 14) labeled by nick-translation.

Figure 13A:
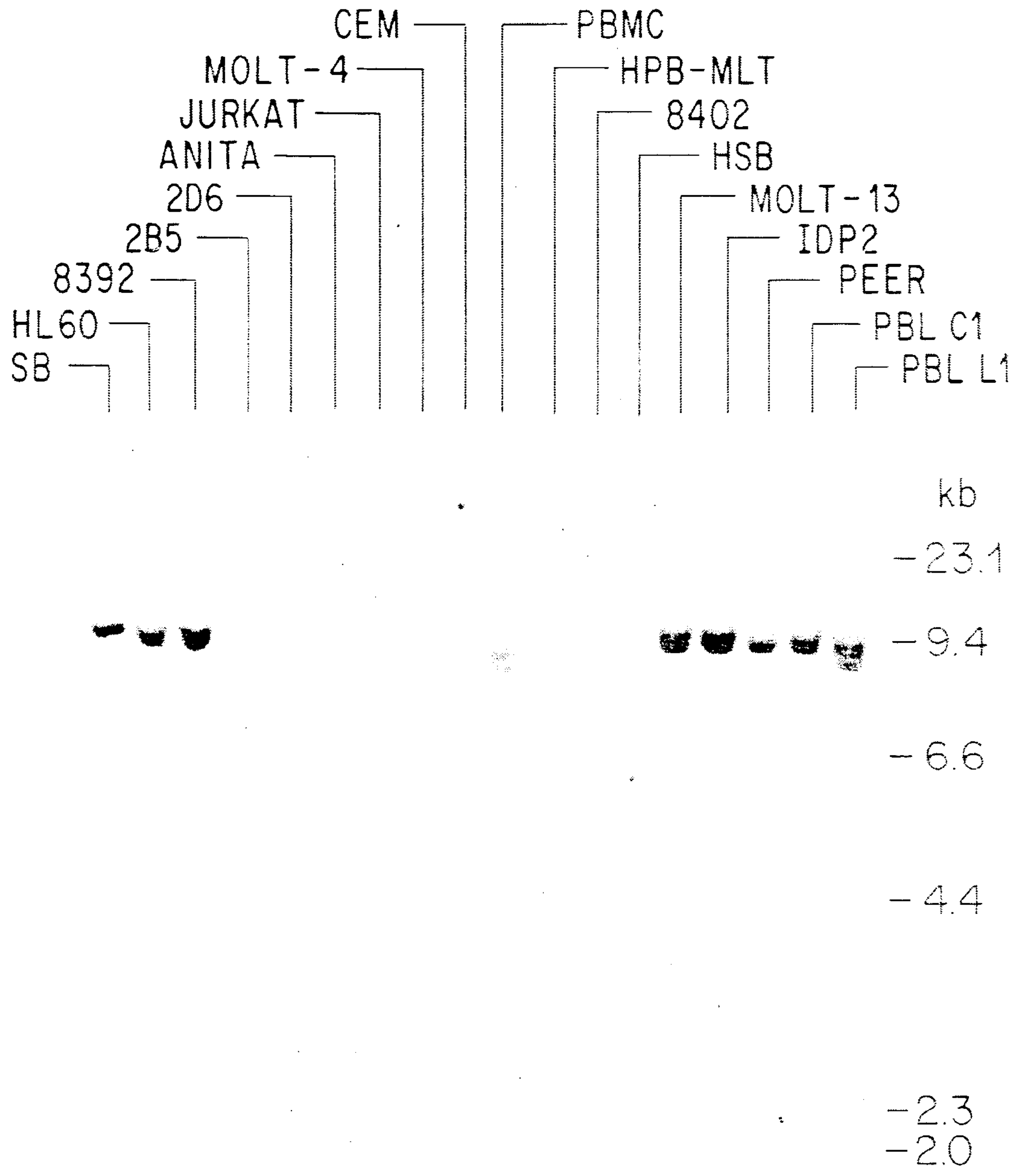

FIG. 13A. Southern blot analysis of genomic DNA (Xba I digest)

5 μg high molecular weight genomic DNA samples were digested with Xba I, electrophoresed through 0.7% agarose, transferred to nitrocellulose, and probed with nick-translated 0-240. DNA sources are: SB and 8392, B cell lines; HL60, myeloid cell line; 2B5 (unpublished), 2D6 (unpublished),.Anita, Jurkat and HPB-MLT TCR $\alpha\beta$ T cell lines; Molt-4, CEM, 8402 and HSB, surface TCR$^-$ T cell lines; PBMC, fresh peripheral blood mononuclear cells; Molt-13, IDP2, PEER and PBL L1, TCR $\gamma\delta$ T cell lines. Bacteriophage lambda DNA digested with Hind III was used as a molecular weight standard Germline bands are marked by arrowheads.

Figure 13B:
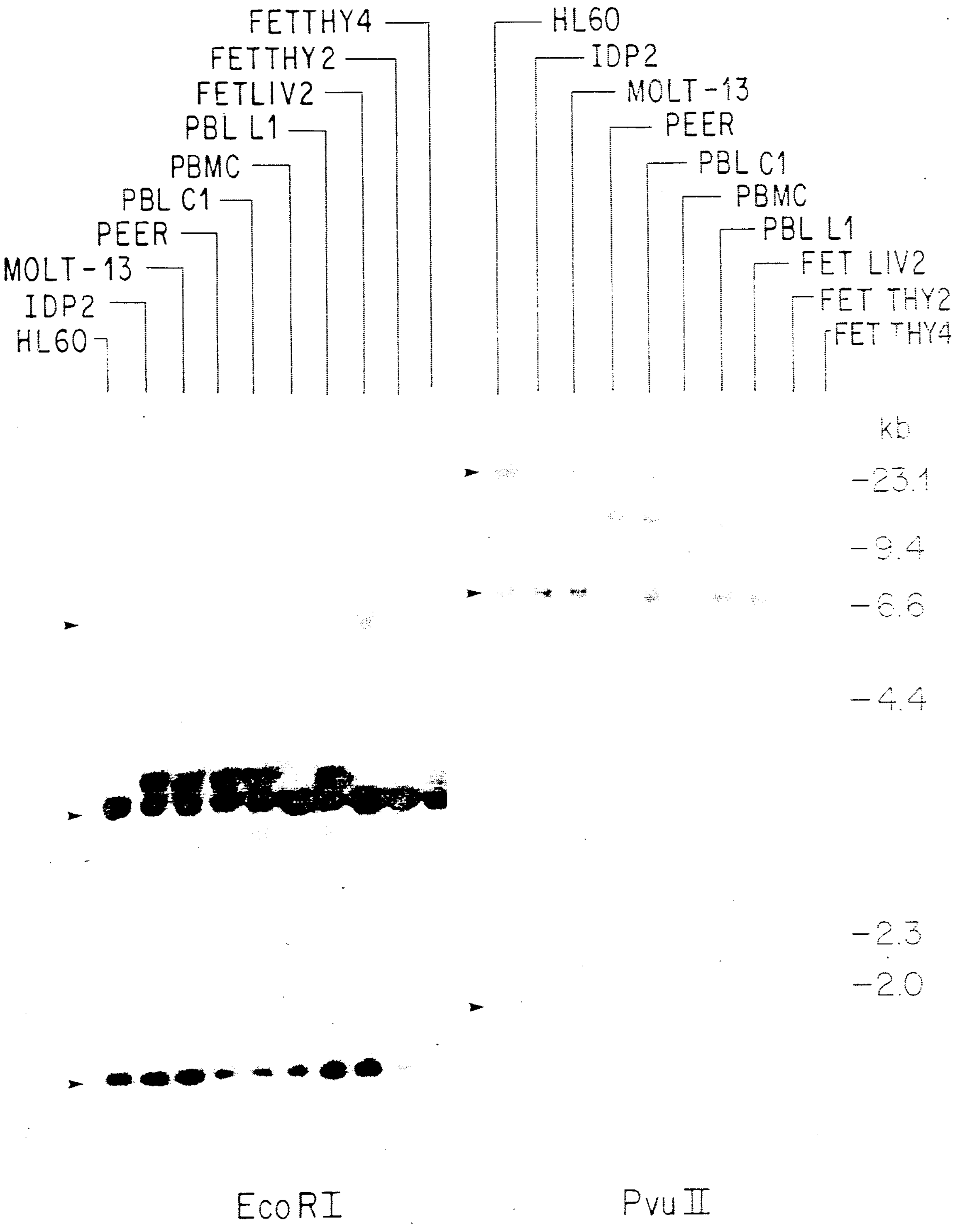

FIG. 13B. Southern blot analysis of genomic DNA (Eco RI and Pvu II digests)

Genomic DNA samples digested with Eco RI or Pvu II probed with the 425 bp 5′ Eco RI fragment of clone 0-240/38 (VJC probe; see FIG. 14) labelled by nick-translation. PBL C1 is a TCR $\gamma\delta$ T cell clone (75); FET LIV 2 and FET THY 2 are fetal liver and thymus samples from the same fetus; FE THY 4 is from distinct fetus; other DNA samples are those used in FIG. 13A. Germline bands in each digest are marked by arrowheads.

Figure 14:
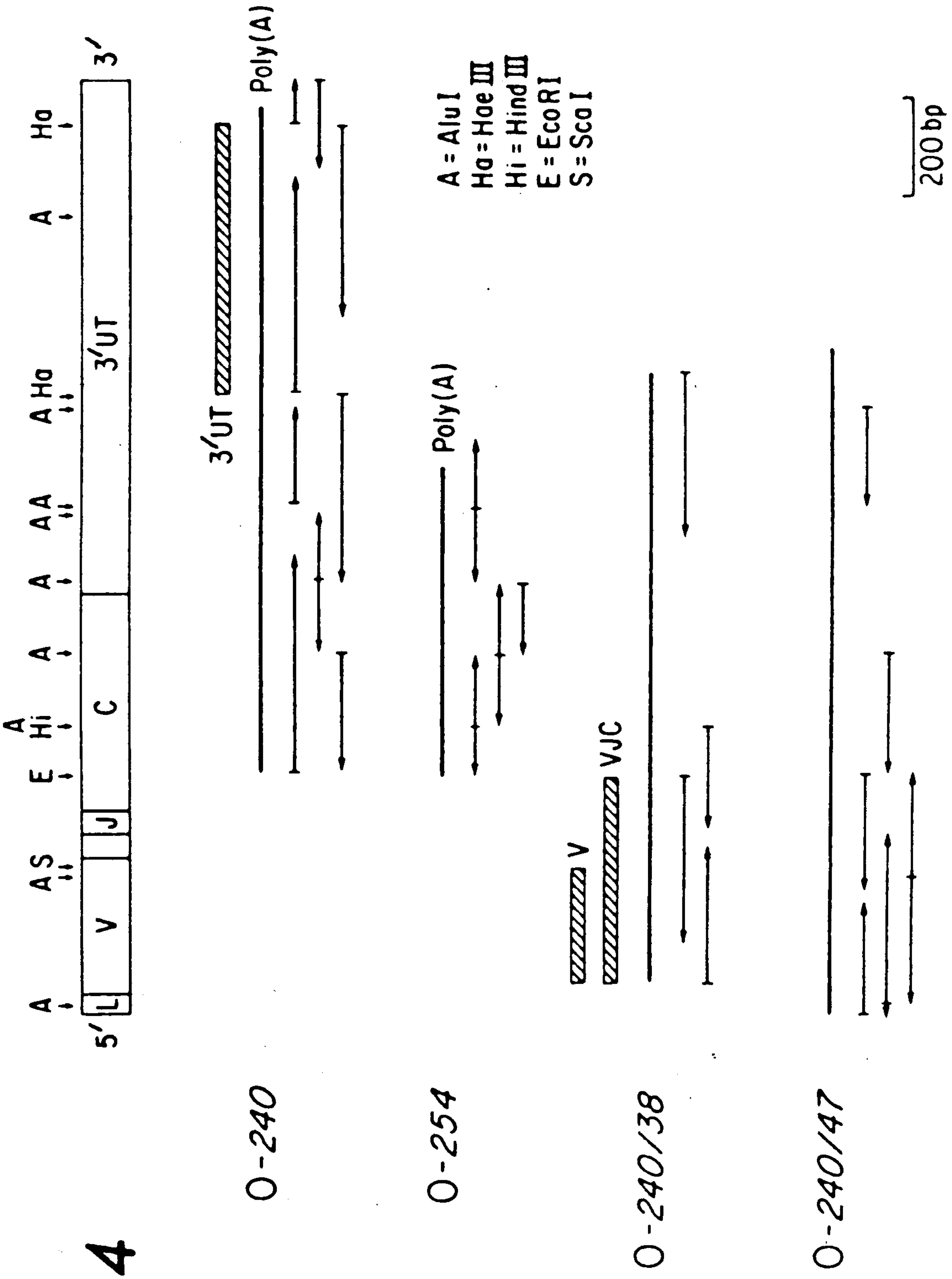

FIG. 14. Organization and sequencing strategy of group O cDNA clones

FIG. 15. Composite nucleotide sequence of group O cDNA clones.

Amino acid residues are numbered from the presumed amino terminal processing point. Cysteine residues are boxed, potential N-linked glycosylation sites are bracketed, and polyadenylation signals used in 0-240 and 0-254 are underlined. The composite nucleotide sequence is compared with that of the coding region of murine cDNA clone DN-4 (79). (−) denotes identity and (*) denotes a gap.

Figure 16:
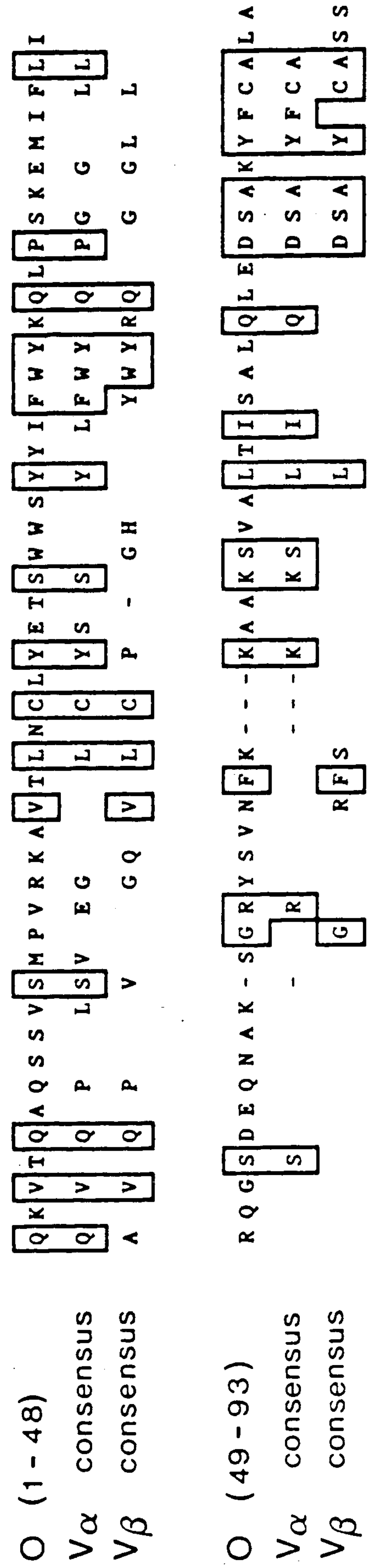

FIG. 16. Amino acid sequence comparisons to consensus human TCR V region sequences.

Blanks indicate consensus assignment at that position. (−) indicates a gap. Identities between the O-composite sequence and consensus residues are boxed.

Figure 17:
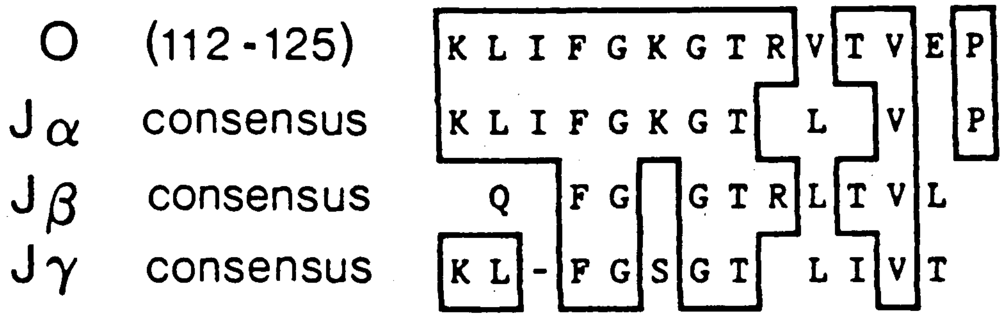

FIG. 17. Amino acid sequence comparisons to consensus human TCR J region sequences.

Figure 18:
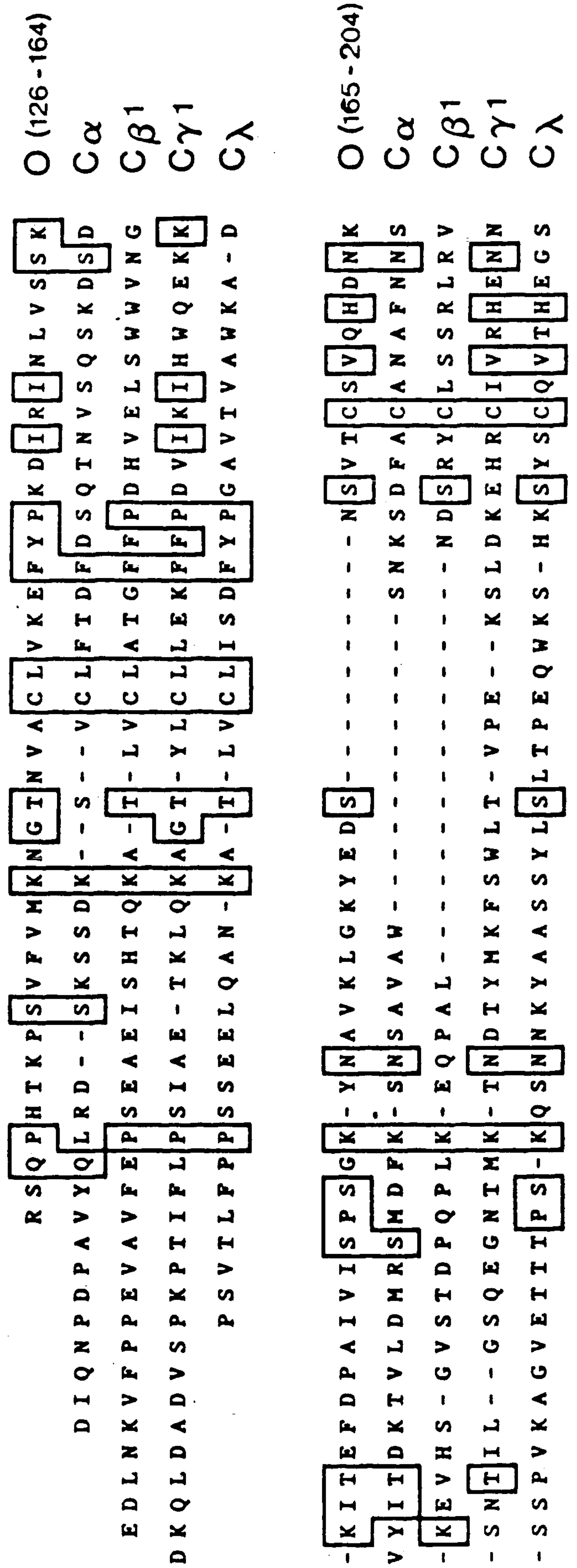
Figure 18:
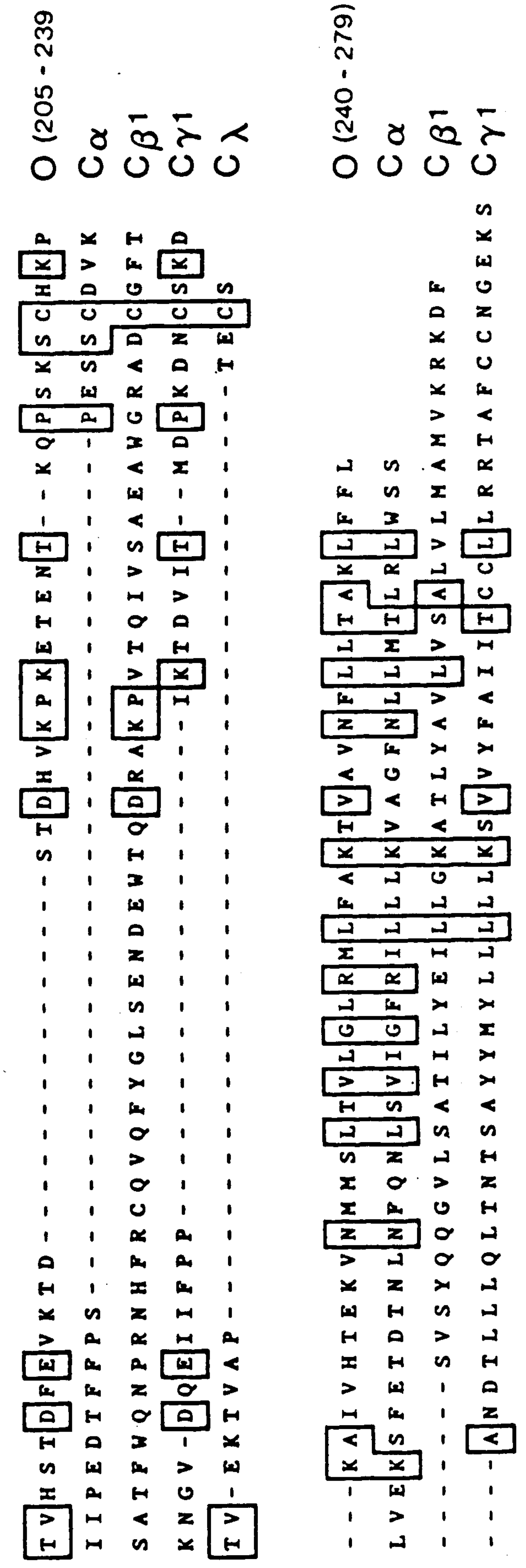

FIG. 18. Amino acid sequence comparisons to human TCR and immunoglobulin C region sequences.

Figure 19:
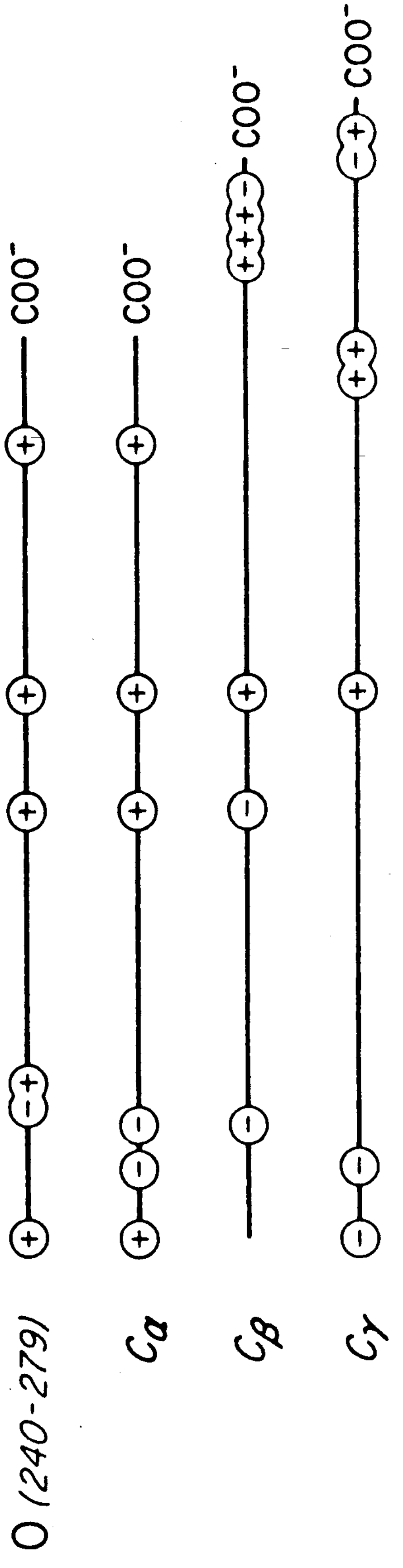

FIG. 19. Distribution of charged and uncharged amino acids in the region flanking and including the presumed transmembrane region of the o-composite sequence compared with those of Cα, Cβ, and Cγ.

Figure 20:
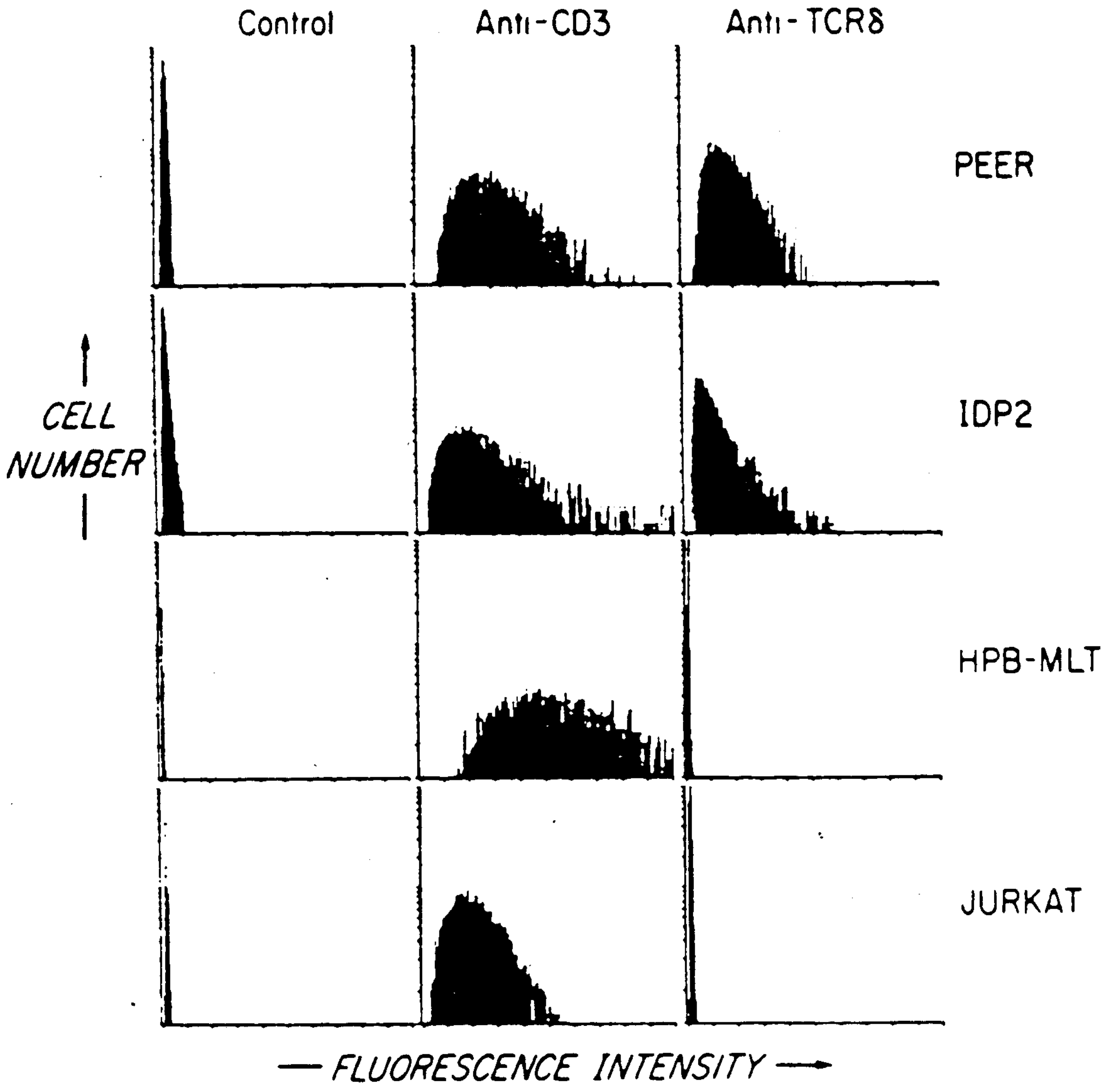

FIG. 20. Cytofluorographic analysis of T cell lines with anti-TCR δ1

Figure 21:
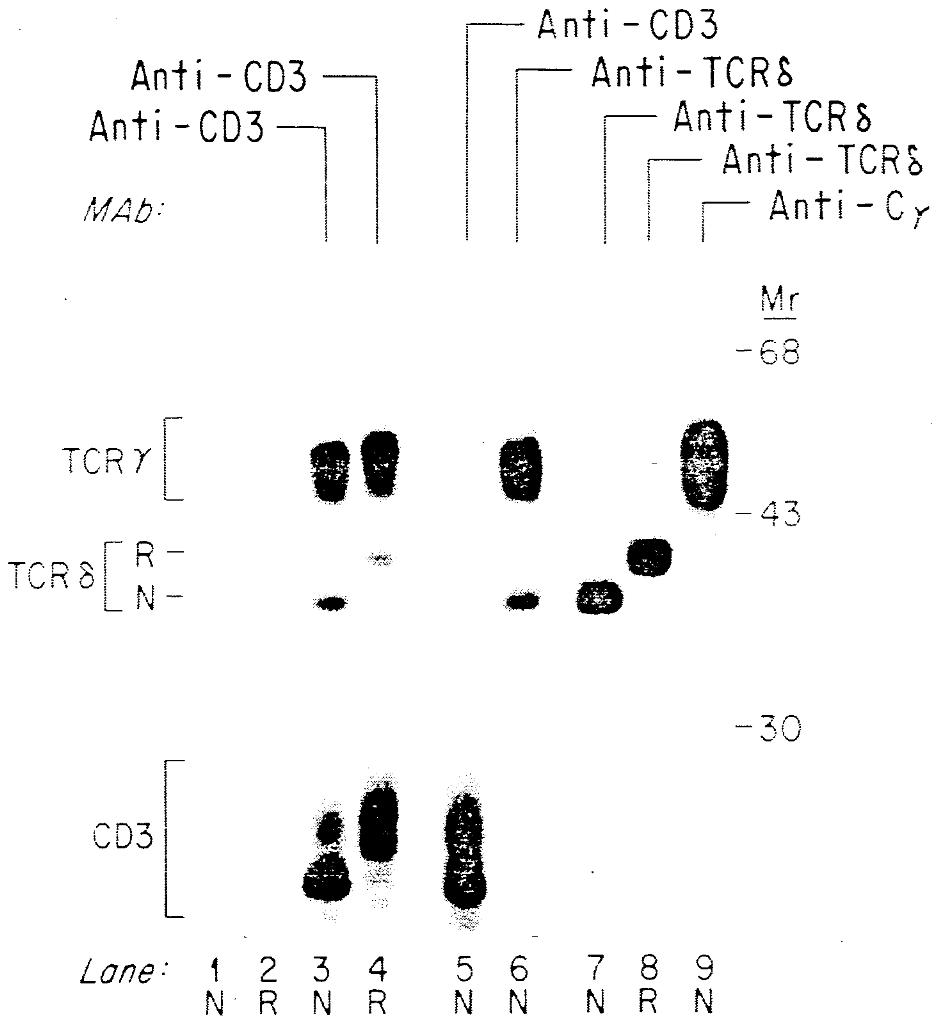

FIG. 21. Immunochemical analysis of the specificity of mAb anti-TCR δ1

Surface $^{125}$I-labeled IDP2 cells were immunoprecipitated using control mAb P3 (lanes 1 and 2), anti-Leu 4 (lanes 3–5), anti-TCR δ1 (lanes 6–8), or anti-Cγ serum (lane 9) and were then resolved by SDS-PAGE and visualized by autoradiography N=nonreducing conditions, R=reducing conditions.

Figure 22:
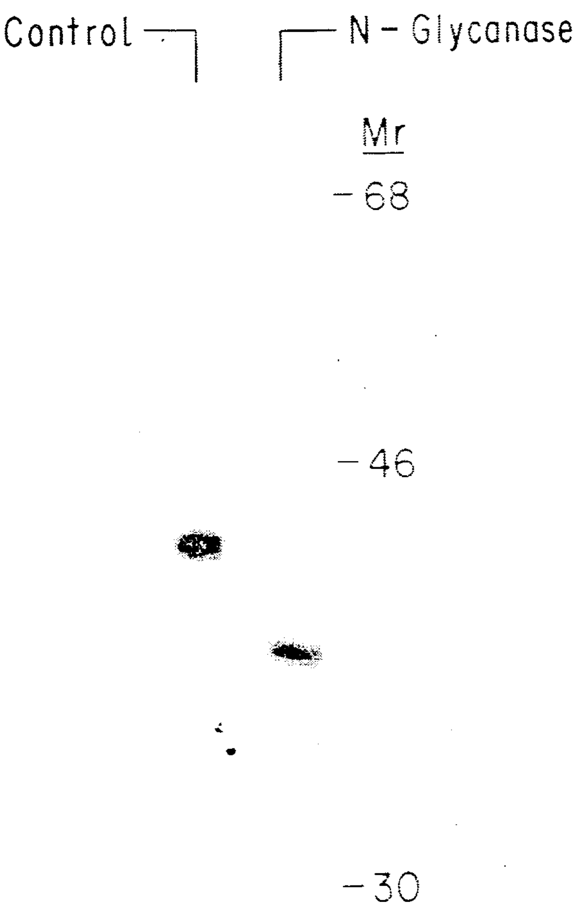

FIG. 22. N-glycanase digestion of TCR δ.

Figure 23:
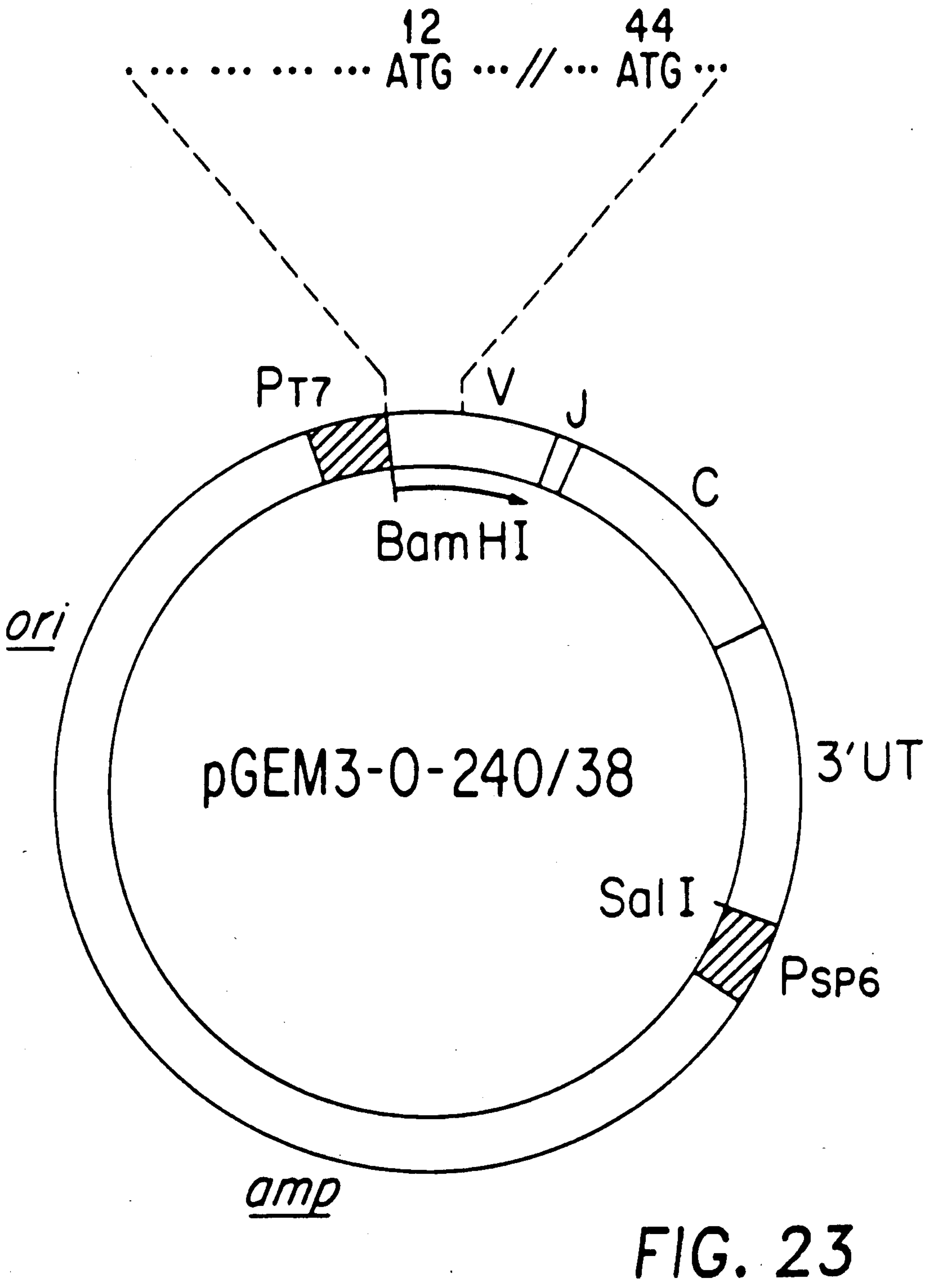

FIG. 23. Map of pGEM3-O-240/38

Figure 24:
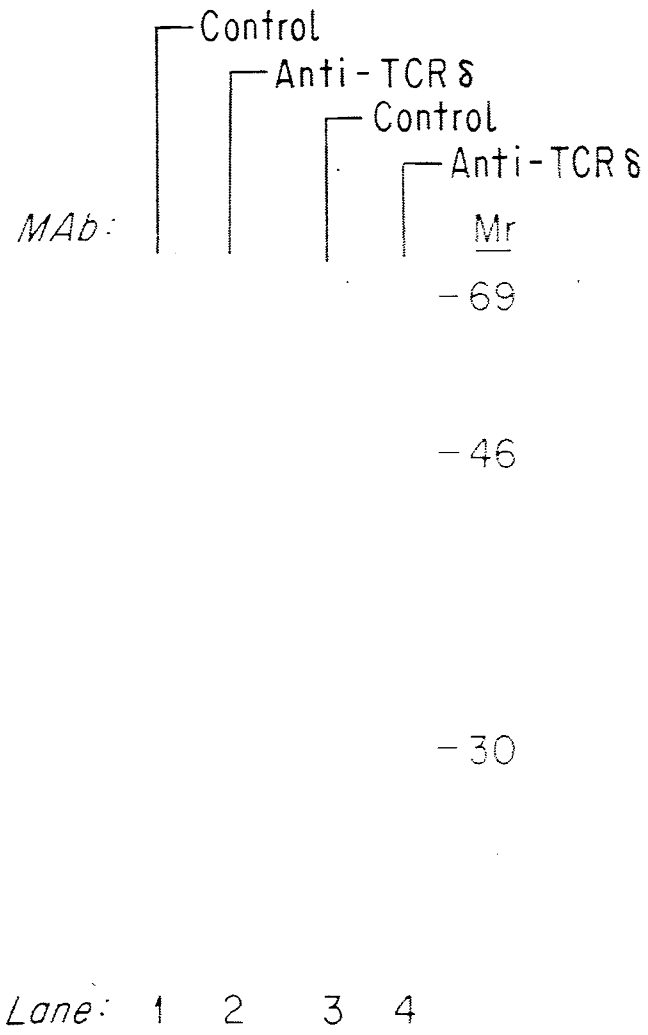

FIG. 24. Immunoprecipitation of in vitro translation products of cDNA clone IDP2 O-240/38 by mAb anti-TCR δ1

Figure 25:
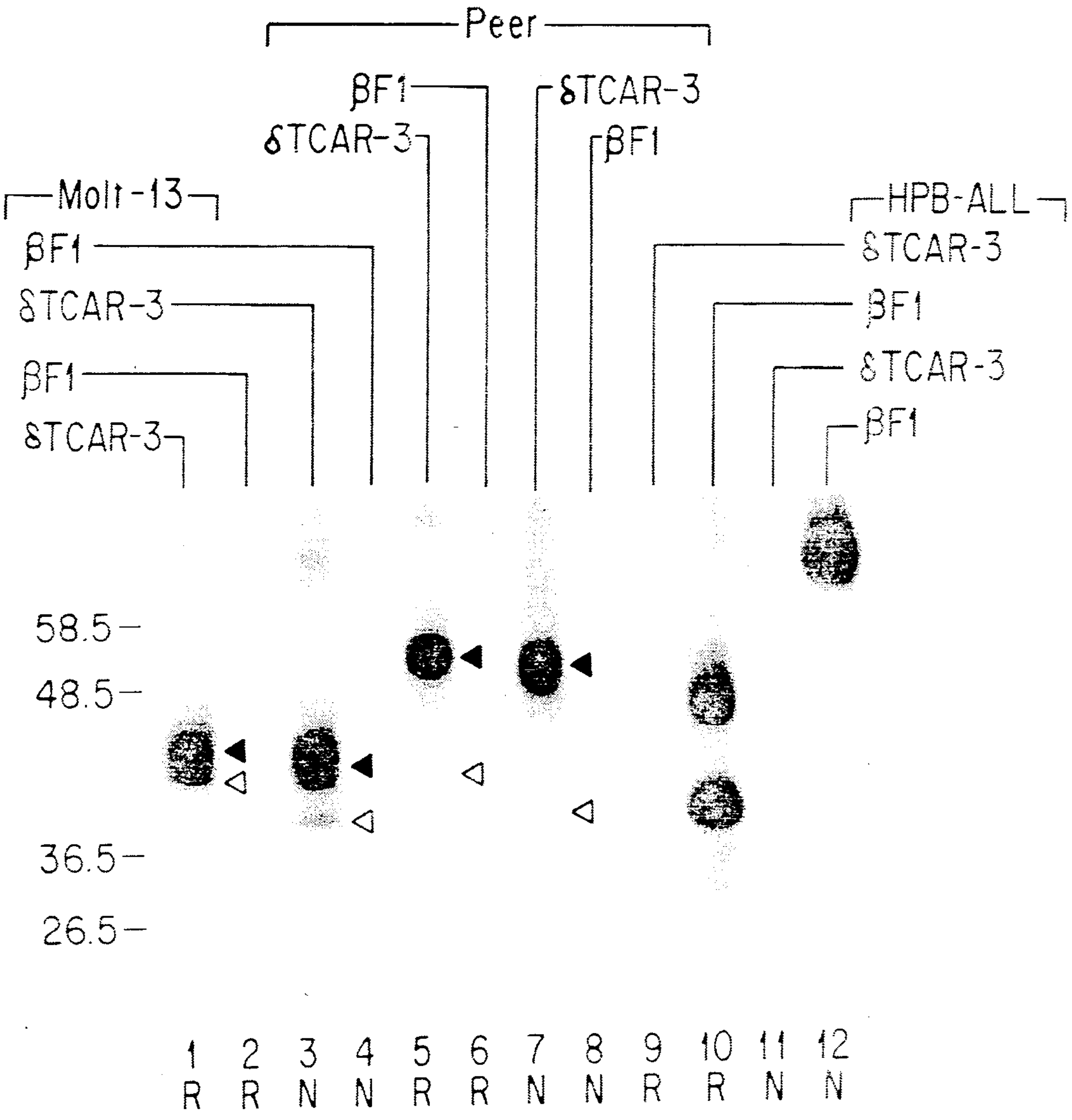

FIG. 25. Immunoprecipitation and SDS-PAGE analysis of T cell antigen receptor.

Open arrowheads indicate the position of the δ chains. The solid arrowheads indicate the position of the γ chains. Lysates were immunoprecipitated using δTCAR-3 antibody (odd numbered lanes) or βF1 antibody (even numbered lanes).

Figure 26:
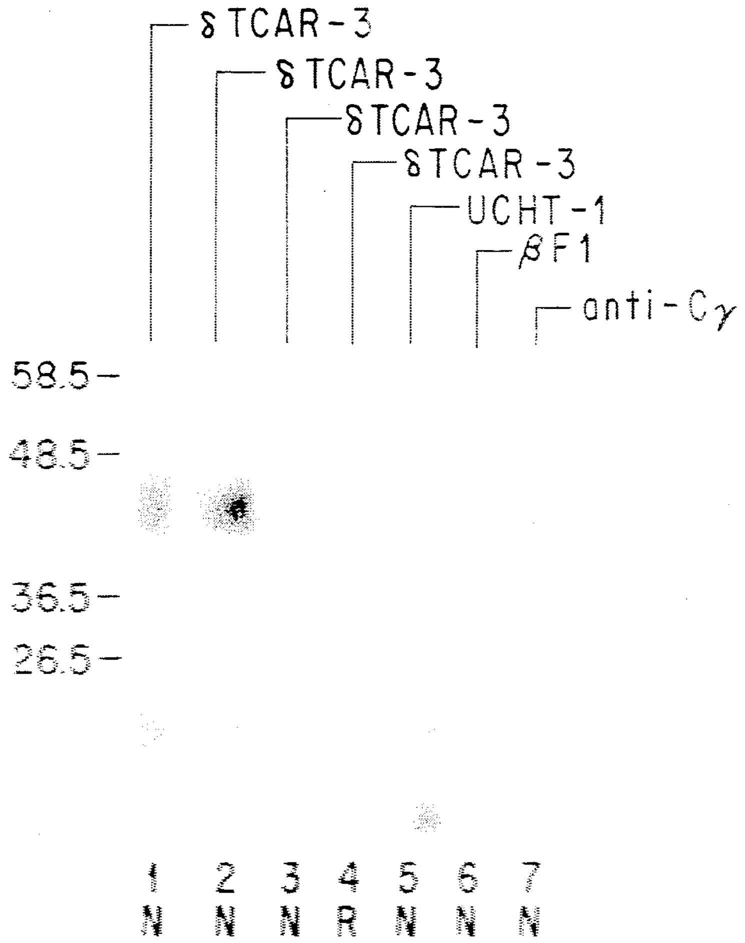

FIG. 26. Immunoprecipitation of δ chain by δTCAR-3 antibody

Molt-13 cells solubilized in Tris-buffered saline (pH 8) containing 0.3% CHAPS (lane 1) or in 1% Triton X-100 (lanes 2–7). Lane 1, δTCAR-3 immunoprecipitates γδ heterodimer with the CD3 proteins. Lane 2, δ TCAR-3 immunoprecipitates γδ heterodimer without the CD3 proteins. Lanes 3 and 4, δTCAR-3 immunoprecipitates single δ chain from denatured lysates (N) and reducing (R) conditions, respectively. Lane 5, UCHT-1 immunoprecipitates the CD3 proteins. Lane 6, βF1 antibody does not immunoprecipitate a heterodimer from MOLT-13 cells. Lane 7, anti-Cγ antiserum immunoprecipitates a single γ chain.

Figure 27:
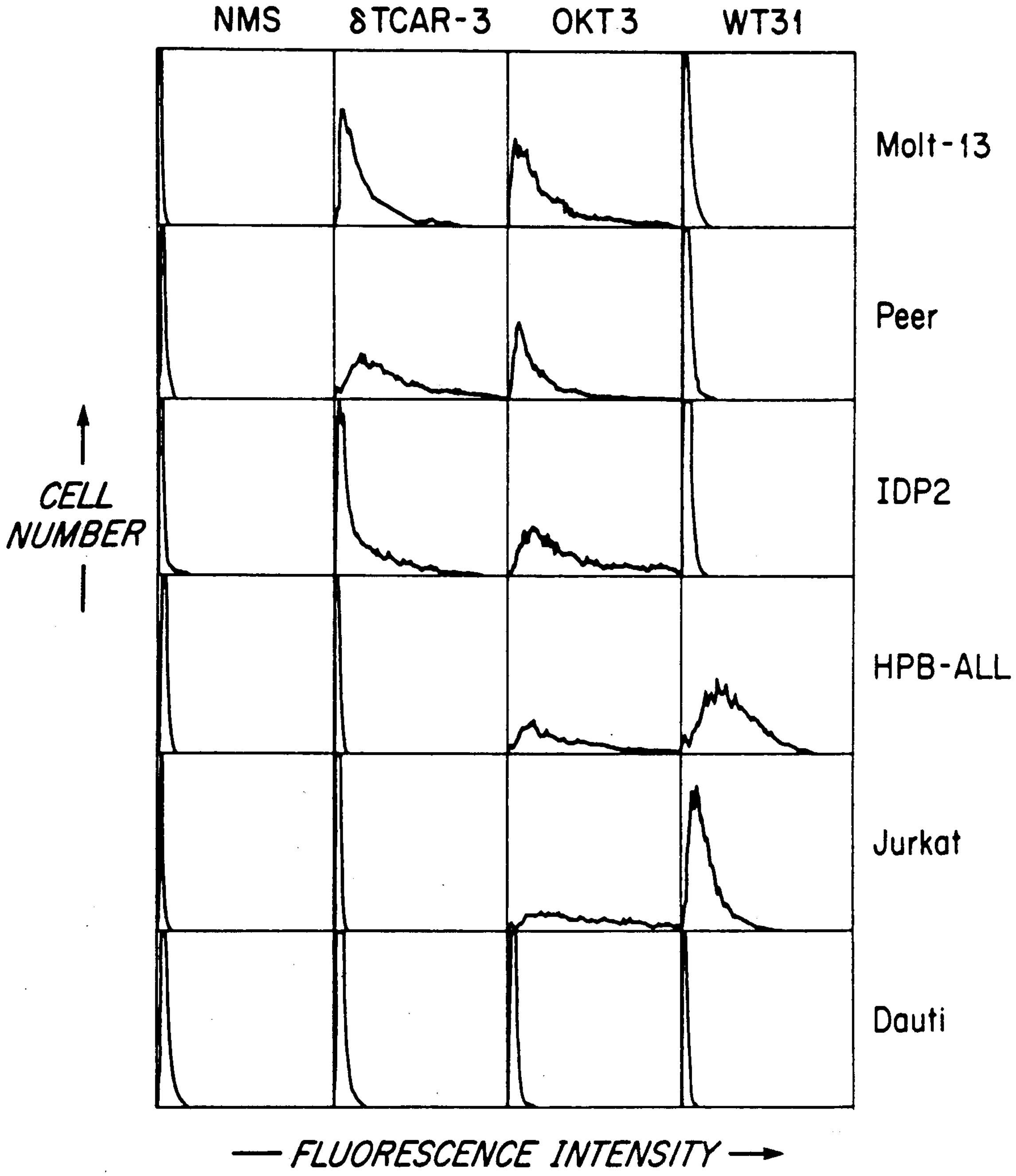

FIG. 27. Analysis of cell surface staining by flow cytometry.

γ, δ positive cells (MOLT-13, PEER, IDP2) and α, β positive cells (HPB-ALL, JURKAT) were incubated with δ TCAR-3, OKT 3, WT31 and normal mouse serum (NMS) antibodies and analyzed by flow cytometry. The B cell line, DAUDI, was the negative control.

Figure 28:
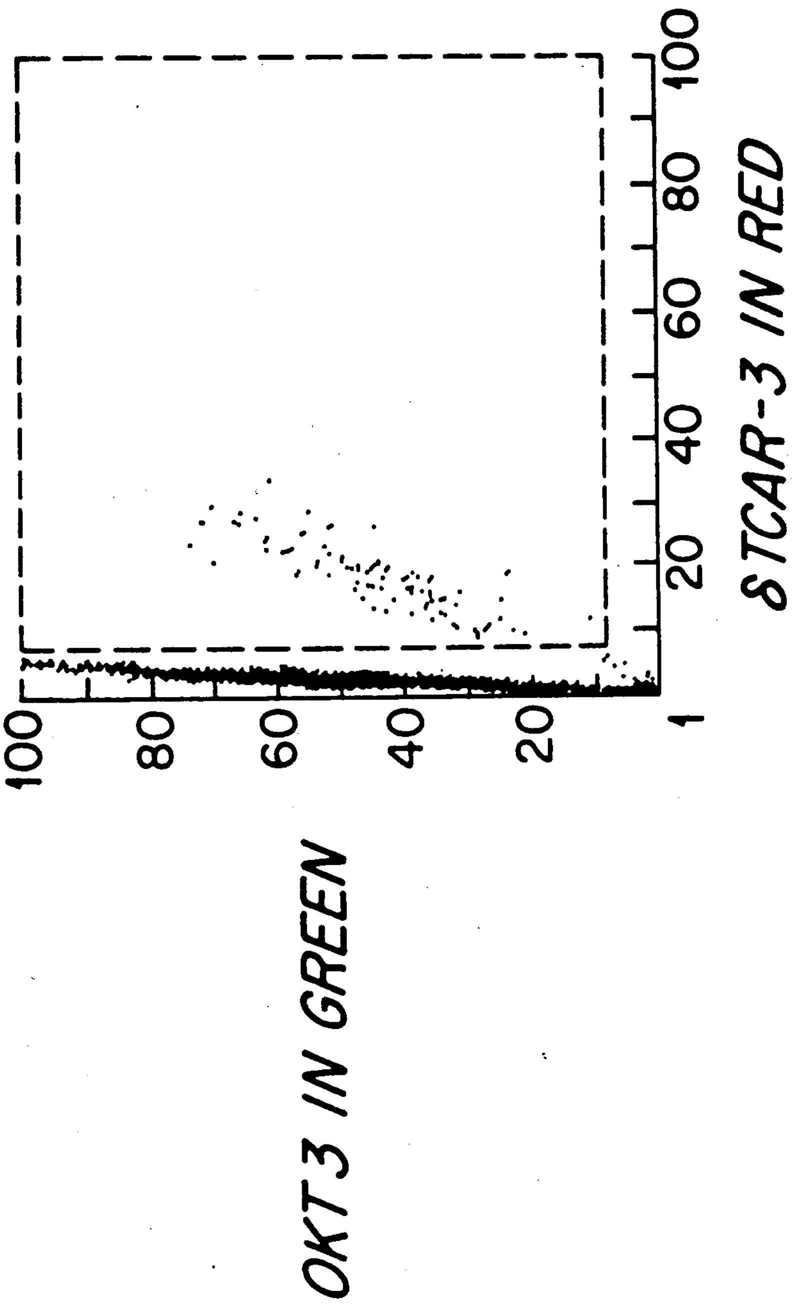

FIG. 28. Two color cytofluorographic analysis of δTCAR-$3^+$ and OKT $3^+$ peripheral blood lymphocytes.

The FITC fluorescence is depicted on the Y axis and PE fluorescence on the X axis. The $CD3^+$ γ,$δ^+$ cells in this sample represent 2.4% of $CD3^+$ lymphocytes.

Figure 29A:
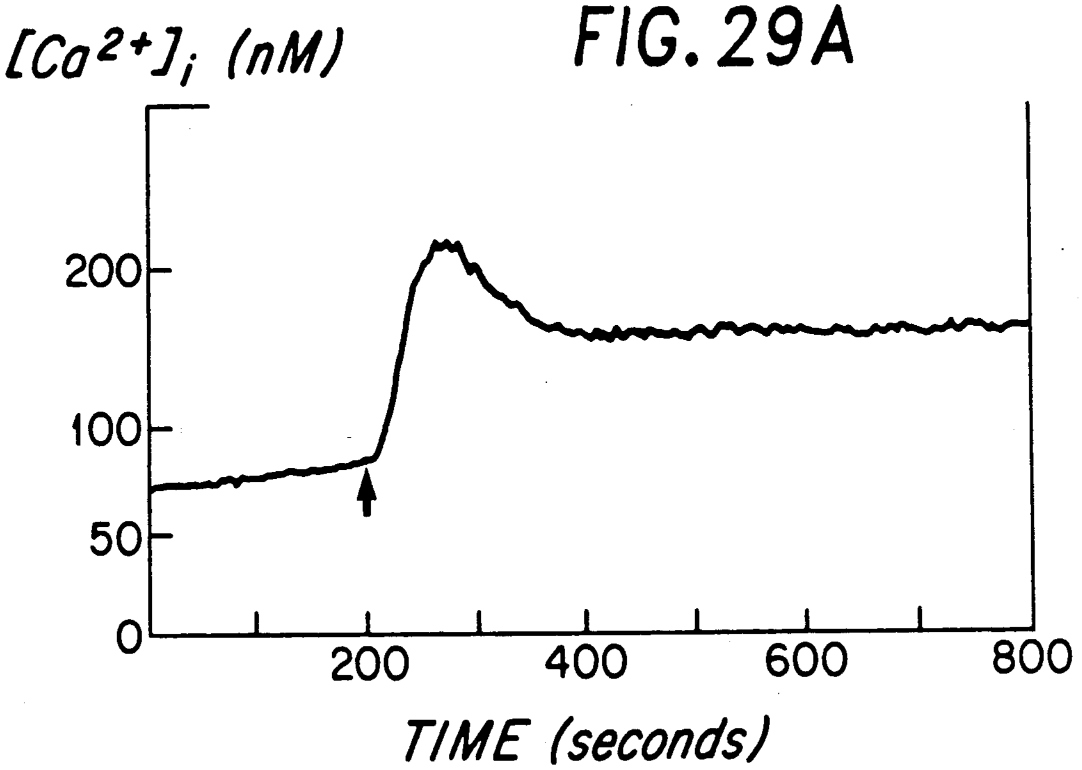
Figure 29B:
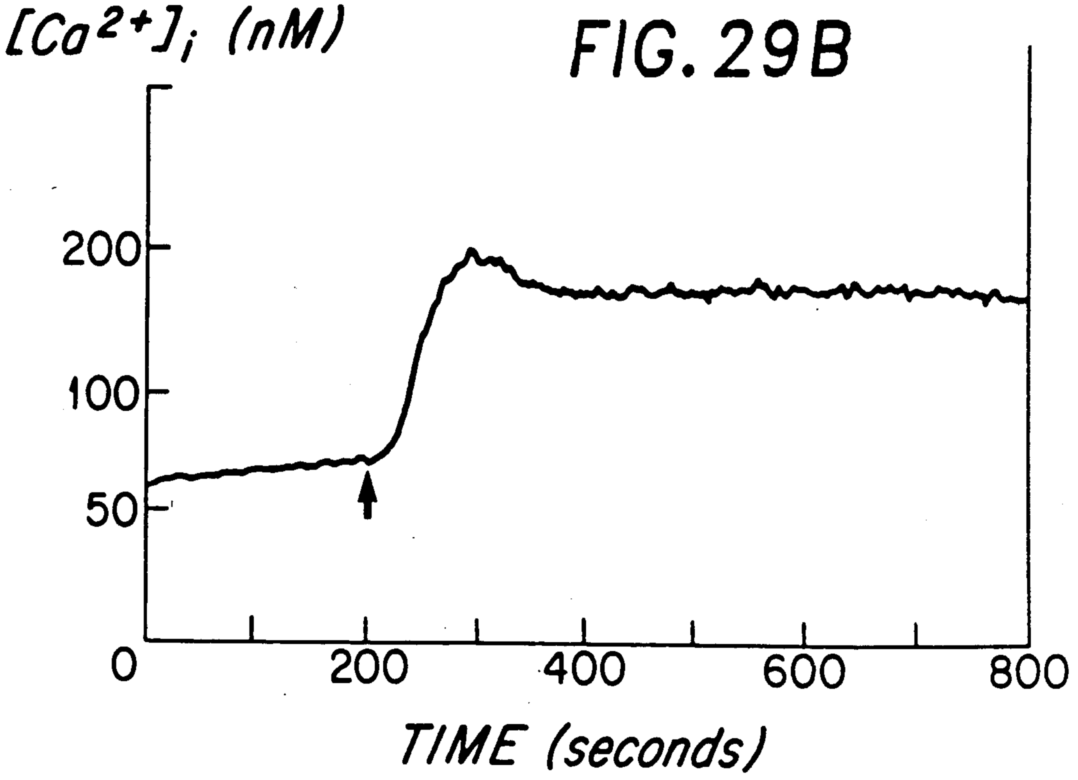

FIG. 29. Measurement of intracytoplasmic $Ca^{2+}$ concentration ($[Ca^{2+}]_i$) versus time Top panel:δTCAR-3

Bottom panel:Anti-Leu antibody

Arrows indicate the time of addition of antibody.

DETAILED DESCRIPTION OF THE INVENTION

The present invention provides a purified polypeptide which comprises at least a portion of a δ T cell receptor polypeptide. This polypeptide may have at least one intrachain, covalent, disulphide bridge Additionally, the polypeptide may comprise a δ T cell receptor polypeptide having a molecular weight of about 40,000 daltons. Furthermore, the δ T cell receptor polypeptide may be a human δ T cell receptor polypeptide. In one embodiment of the invention the polypeptide comprises at least a portion of the amino acid sequence shown in FIG. 15.

A substance capable of specifically forming a complex with at least one δ T cell receptor polypeptide is also provided by the invention. In one embodiment of the invention, the substance is capable of specifically forming a complex with one δ T cell receptor polypeptide. In another embodiment of the invention, the substance is capable of specifically forming a complex with more than one δ T cell receptor polypeptide. The substance may be an antibody. The antibody may be a polyclonal antibody or a monoclonal antibody.

Also provided is a method for detecting T cells, each of which has a δ T cell receptor polypeptide. This method comprises contacting a sample containing T cells with substances capable of forming complexes with δ T cell receptor polypeptides so as to form cellular complexes between the substances and the δ T cell receptor polypeptides. These cellular complexes are detected and thereby T cells, each of which has a δ T cell receptor polypeptide, are detected.

Accordingly, in one embodiment of the invention, the δ T cell receptor polypeptides are present on the surfaces on the T cells. In another embodiment of the invention, the δ T cell receptor polypeptides are present in the cytoplasm of the T cells.

This method may be performed by forming complexes with a specific δ T cell receptor polypeptide In one embodiment of the invention, the specific δ T cell receptor polypeptide is present only in suppressor T cells.

The invention further provides a method for diagnosing an immune system abnormality in a subject. Within this application, immune system abnormality means a condition of immunological responsiveness to antigens characterized by an increased or a decreased immune response compared to a normal or standard immune response. Accordingly, immune system abnormality includes, but is not limited to, immunodeficiency conditions and diseases, e.g. acquired immune deficiency syndrome and congenital immunodeficiencies and hyperimmune conditions and diseases, e.g. allergies and hayfever. The method of the present invention comprises determining the number of T cells in a sample from the subject and contacting the sample with the substances capable of forming complexes with at least one δ T cell receptor polypeptide so as to form cellular complexes between the substances and δ T cell receptor polypeptides The percentage of T cells in the sample which have a δ T cell receptor polypeptide is determined and compared with the percentage of T cells which have a δ T cell receptor polypeptide in a sample from a normal subject who does not have the immune system abnormality A difference in the percentage of T cells so determined would be indicative of the immune system abnormality.

In one embodiment of the invention, the immune system abnormality is a cancer. The cancer may be a leukemia or a lymphoma. In another embodiment of the invention, the immune system abnormality is acquired immune deficiency syndrome In yet another embodiment of the invention, the immune system abnormality is congenital immunodeficiency. In still a further embodiment of the invention, the immune system abnormality is an autoimmune disease.

The subject in whom the immune system abnormality is diagnosed may be an animal. In one embodiment of the invention the subject is a human. Furthermore, the sample from the subject may comprise blood or tissue.

Yet another method for diagnosing an immune system abnormality is provided by the present invention. This method comprises determining the number of δ T cell receptor polypeptide bearing T cells in a sample from the subject and the amount of δ T cell receptor polypeptides in the T cell receptor polypeptide bearing T cells. The amount of δ T cell receptor polypeptides so determined is compared with the amount of δ T cell receptor polypeptides in an equal number of δ T cell receptor polypeptide bearing T cells in a sample from a normal subject who does not have the immune system abnormality. A difference in the amount so determined would be indicative of the immune system abnormality. In one embodiment of the invention, the amount of a single δ T cell receptor polypeptide is determined A further method for diagnosing an immune system abnormality in a subject is provided. This method comprises determining in a sample from the subject the number of T cells which have a δ T cell receptor polypeptide and the number of T cells consisting of the group of T cells which have one of the surface markers T4, T8 and α, β T cell receptor. The numbers of T cells so determined is compared with the number of T cells which have a δ T cell receptor polypeptide and the number of T cells in the group which have the same surface marker as the group of T cells determined in the sample from the subject, in a sample from a subject who does not have the immune system abnormality. A difference in the number of T cells so determined which have a δ T cell receptor polypeptide relative to the number of T cells in the group so determined would be indicative of the immune system abnormality.

The present invention also provides a nucleic acid molecule encoding a δ T cell receptor polypeptide having a molecular weight of about 40,000 daltons. In one embodiment of the invention, the molecule is a DNA molecule. In another embodiment of the invention the DNA molecule comprises at least a portion of the nucleic acid sequence shown in FIG. 15. Further provided is a nucleic acid molecule which is complementary to the nucleic acid molecule which encodes a δ T cell receptor polypeptide.

A purified polypeptide which comprises at least a portion of a γ T cell receptor polypeptide is also provided by the present invention. This polypeptide may comprise a γ T cell receptor polypeptide having a molecular weight of about 55,000 daltons. In one embodiment of the invention, the polypeptide has a peptide sequence with a molecular weight within the range from about 31,000 daltons to about 40,000 daltons. Additionally, the polypeptide may be a human γ T cell receptor polypeptide.

The present invention further provides a purified complex which comprises two γ T cell receptor polypeptides of the present invention associated with each other. In one embodiment of the invention, the two γ T cell receptor polypeptides are associated with each other through at least one interchain, covalent, disulphide linkage. In another embodiment of the invention, the two γ T cell receptor polypeptides are noncovalently associated with each other. In still another embodiment of the invention, the two γ T cell receptor polypeptides have the same constant domain. In yet a further embodiment of the invention, the two γ T cell receptor polypeptides have different constant domains.

The present invention also provides a substance capable of specifically forming a complex with at least one γ T cell receptor polypeptide. In one embodiment of the invention, the substance is capable of specifically forming a complex with one γ T cell receptor polypeptide. In another embodiment of the invention, the substance is capable of specifically forming a complex with more than one γ T cell receptor polypeptide. The substance may be an antibody. In one embodiment of the invention, the antibody is a polyclonal antibody. In another embodiment of the invention, the antibody is a monoclonal antibody A method for detecting T cells, each of which has a γ T cell receptor polypeptide, is further provided. This method comprises contacting a sample which contains T cells with substances capable of forming complexes with γ T cell receptor polypeptides so as to form cellular complexes between the substances and the γ T cell receptor polypeptides. These cellular complexes are detected and thereby T cells, each of which has a γ T cell receptor polypeptide, are detected. In one embodiment of the invention, the Δ T cell receptor polypeptides are present on the surfaces of the T cells. In another embodiment of the invention, the γ T cell receptor polypeptides are present in the cytoplasm of the T cells. In yet another embodiment of the invention, the substances are capable of forming complexes with a specific γ T cell polypeptide. The specific γ T cell receptor polypeptide may be present only in suppressor T cells. Furthermore, the γ T cell receptor polypeptide may be associated with another γ T cell receptor polypeptide. In one embodiment of the invention, the γ T cell receptor polypeptide is associated with another γ T cell receptor polypeptide. In another embodiment of the invention, the γ T cell receptor polypeptide is associated with another γ T cell receptor polypeptide only in non-major histocompatibility restricted cytotoxic T lymphocytes Furthermore, the non-major histocompatibility complex restricted cytotoxic T lymphocytes may be T killer cells or natural killer-like cells.

The present invention further provides a method for diagnosing an immune system abnormality in a subject. This method comprises determining the number of T cells in a sample from the subject and contacting the sample with substances capable of forming complexes with at least one γ T cell receptor polypeptide so as to form cellular complexes between the substances and γ T cell receptor polypeptides. The percentage of T cells in the sample which have a γ T cell receptor polypeptide is determined and compared with the percentage of T cells which have a γ T cell receptor polypeptide in a normal subject who does not have the immune system abnormality. A difference in the percentage of T cells so determined would be indicative of the immune system abnormality In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In still a further embodiment of the invention, the immune system abnormality is an autoimmune disease.

The subject in which the immune system abnormality is diagnosed may be an animal. Additionally, the subject in which the immune system abnormality is diagnosed may be a human. Furthermore, the sample of which the percentage of T cells which have a γ T cell receptor polypeptide is determined may comprise blood or tissue.

Yet another method for diagnosing an immune system abnormality in a subject is provided by the present invention. This method comprises determining the number of γ T cell receptor polypeptide bearing T cells in a sample from the subject and the amount of γ T cell receptor polypeptides in the γ T cell receptor polypeptide bearing T cells. The amount of γ T cell receptor polypeptides so determined is compared with the amount of γ T cell receptor polypeptides in an equal number of γ T cell receptor polypeptide bearing T cells in a sample from a normal subject who does not have the immune system abnormality. A difference in the amount so determined would be indicative of the immune system abnormality. In one embodiment of the invention, the amount of a single γ T cell receptor polypeptide is determined.

Further provided is another method for diagnosing an immune system abnormality in a subject This method comprises determining in a sample from the subject the number of T cells which have a $\gamma$ T cell receptor polypeptide and the number of T cells consisting of the group of T cells which have one of the surface markers T4, T8 and $\alpha$, $\beta$ T cell receptor The numbers of T cells so determined are compared with the of T cells which have a $\gamma$ T cell receptor polypeptide and the number of T cells in the group which have the same surface marker as the group determined in the sample from the subject, in a sample from a subject who does not have the immune system abnormality. A difference in the number of T cells so determined which have a T cell receptor polypeptide relative to the number of T cells in the group so determined would be indicative of the immune system abnormality.

A purified complex which comprises at least a portion of a $\delta$ T cell receptor polypeptide and at least a portion of a $\gamma$ T cell receptor polypeptide is further provided by the present invention. This complex may comprise a $\delta$ T cell receptor polypeptide having a molecular weight of about 40,000 daltons and a $\gamma$ T cell receptor polypeptide having a molecular weight of about 55,000 daltons. Furthermore, the $\delta$ T cell receptor polypeptide may be a human $\delta$ T cell receptor polypeptide and the $\gamma$ T cell receptor polypeptide may be a human $\gamma$ T cell receptor polypeptide. Moreover, the $\delta$ T cell receptor polypeptide and the $\gamma$ T cell receptor polypeptide may be associated with each other through at least one interchain, covalent, disulphide linkage, or may be noncovalently associated with each other.

Also provided is a substance capable of specifically forming a complex with at least one $\gamma$, $\delta$ T cell receptor complex. This substance may be capable of forming a complex with one $\gamma$, $\delta$ T cell receptor complex. Furthermore, the substance may be capable of forming a complex with more than one $\gamma$, $\delta$ T cell receptor complex.

In one embodiment of the invention, the substance is an antibody. In another embodiment of the invention, the substance is a polyclonal antibody. In yet another embodiment of the invention, the substance is a monoclonal antibody.

The present invention further provides a method for detecting T cells, each of which has a $\gamma$, $\delta$ T cell receptor complex. This method comprises contacting a sample containing T cells with substances capable of forming complexes with $\gamma$, $\delta$ T cell receptor complexes so as to form cellular complexes between the substances and the $\gamma$, $\delta$ T cell receptor complexes. These cellular complexes are detected and thereby T cells, each of which has a $\gamma$, $\delta$ T cell receptor complex, are detected In one embodiment of the invention, the $\gamma$, $\delta$ T cell receptor complexes are present on the surface of the T cells. In another embodiment of the invention, the $\gamma$, $\delta$ T cell receptor complexes are present in the cytoplasm of the T cells. In yet another embodiment of the invention, the substances are capable of forming complexes with a specific $\gamma$, $\delta$ T cell receptor complex. The specific $\gamma$, $\delta$ T cell receptor complex may be present only in suppressor T cells.

A method for diagnosing an immune system abnormality in a subject is further provided by the present invention. This method comprises determining the number of T cells in a sample from the subject and contacting the sample with substances capable of forming complexes with at least one $\gamma$, $\delta$ T cell receptor complex so as to form cellular complexes between the substances and $\gamma$, $\delta$ T cell receptor complexes. The percentage of T cells in the sample which have a $\gamma$, $\delta$ T cell receptor complex is determined and compared with the percentage of T cells which have a $\gamma$, $\delta$ T cell receptor complex in a sample from a normal subject who does not have the immune system abnormality. A difference in the percentage of T cells so determined would be indicative of the immune system abnormality. In one embodiment of the invention, the immune system abnormality is a cancer. The cancer may be a leukemia or a lymphoma. In another embodiment of the invention, the immune system abnormality is acquired immune deficiency syndrome. In yet another embodiment of the invention, the immune system abnormality is congenital immunodeficiency. In yet a further embodiment of the invention, the immune system abnormality is an autoimmune disease.

The subject in which the immune system abnormality may be an animal. Furthermore, the subject in which the immune system abnormality is diagnosed may be a human. Moreover, the sample in which the percentage of T cells which have a $\gamma$, $\delta$ T cell receptor complex is determined may comprise blood or tissue.

Still another method for diagnosing an immune system abnormality in a subject is provided by the present invention. This method comprises determining the number of $\gamma$, $\delta$ T cell receptor complex bearing T cells in a sample from the subject and the amount of $\gamma$, $\delta$ T cell receptor complexes in the $\gamma$, $\delta$ T cell receptor complex bearing T cells. The amount so determined is compared with the amount of $\gamma$, $\delta$ T cell receptor complexes in an equal number of $\gamma$, $\delta$ T cell receptor complex bearing T cells in a sample from a normal subject who does not have immune system abnormality. A difference in the amount so determined would be indicative of the immune system abnormality. In one embodiment of the invention, the amount of a single $\gamma$, $\delta$ T cell receptor complex is determined.

Yet a further method for diagnosing an immune system abnormality is provided This method comprises determining in a sample from the subject the number of T cells which have a $\gamma$, $\delta$ T cell receptor complex and the number of T cells consisting of the group of T cells which have one of the surface markers T4, T8 and $\alpha$, $\beta$ T cell receptor complex. The numbers of T cells so determined are compared with the number of T cells which have a $\gamma$, $\delta$ T cell receptor complex and the number of 1. cells in the group which have the same surface marker as the group of T cells determined in the sample from the subject, in a sample from a subject who does not have the immune system abnormality. A difference in the number of T cells so determined which have a $\gamma$, $\delta$ T cell receptor complex relative to the number of T cells in the group so determined would be indicative of the immune system abnormality.

The various methods for diagnosing abnormalities and for detecting T cells provided by the present invention are based upon the novel polypeptides and substances capable of forming complexes with these polypeptides as described more fully hereinabove. The methods utilize methods for detecting and quantifying T cells, including but not limited to, fluorescence activated cell sorting and autoradiography, which are well known to those skilled in the art to which this invention pertains.

EXAMPLES

Example 1

Materials and Methods

Lymphocyte culture and cell population analysis

Viable lymphocytes were isolated by Ficoll-hypaque density centrifugation and stained with 0.5 micrograms of a specific monoclonal antibody, e.g. WT31 (28, 29) or OKT®3, OKT®4 or OKT®8 (Ortho Diagnostic Systems, Inc., Raritan, N.J.), for 30 minutes at 4° C. After washing, the cell pellets were stained again with fluorescein isothiocyanate (FITC)-conjugated goat antimouse IgG(ab)'$_2$ fragments Fluorescence activated cell sorter(FACS) analyses were performed on an Ortho cytofluorograph or a Coulter Epics as previously described (37). Specifically stained positive cells were determined relative to a negative control profile for each cell line (stained with a nonspecific control monoclonal antibody). Cells having fluorescence intensity channel numbers greater than the intercept of the negative control profile with the baseline were counted as positive, and the % positive was calculated relative to the total number of cells counted.

All IL-2 dependent cell lines were propagated in vitro in media composed of RPMI 1640, 10% human serum and conditioned media containing 2-5 units of interleukin-2 activity as previously described (34).

Alloantigen (allo) activated cultures were stimulated with irradiated allogenic peripheral blood lymphocytes at weekly intervals. Mitogen, i.e. phytohemagglutinin (PHA), activated lines were stimulated with a 1:1,000 dilution of PHA (Difco, Detroit, Mich.) at culture initiation.

Reactivity and characterization of cell culture using monoclonal antibodies Immunoprecipitates from $^{125}$I-labeled lymphocyte lysates were analyzed by sodium dodecyl sulfate-polyacrylamide gel electrophoresis (SDS-PAGE). The radioiodinated T leukemia cell lines HPB-MLT and Jurkat, the HTLV-1 transformed cell line ANITA and resting peripheral blood lymphocytes were solubilized in 1% Triton-X-100 (TX-100) and immunoprecipitated with a control antibody, normal mouse serum (NMS) or a framework antibody to TCR α, β i.e., Fl (54). The βF1 monoclonal antibody was prepared according to standard procedures (46, 47, 52). Spleen cells from mice immunized with purified TCR α, β as described in (28) were used for the fusion experiments. A positive clone, βF1, was obtained by immunoprecipitation with T cell lines and peripheral blood lymphocytes as described above.

$^{125}$I-labeled lymphocytes were solubilized in 0.1% TX-100 and immunoprecipitated with NMS, the anti-T3 antibody UCHT-1 (40) and a framework antibody to TCR i.e., WT31. The efficiency of immunoprecipitation with WT31 was improved at the lower TX-100 concentration used here and the monoclonal antibody 187.1 (53) was used as a second antibody.

Two-color FACS analysis of normal adult peripheral blood lymphocytes was performed using an anti-TCR α, β monoclonal antibody and an anti-T3 monoclonal antibody. Peripheral blood lymphocytes were stained first with an FITC-conjugated anti-T3 monoclonal antibody (OKT®3) and then with a biotinyl-anti-TCR α, β monoclonal antibody (βF1) followed by phycoerythrin-conjugated avidin (PE-avidin, Becton Dickenson, Mt. View, Calif.).

Viable lymphocytes were isolated by ficoll-hypaque density centrifugation for SDS-PAGE and FACS analyses. For SDS-PAGE analysis, lymphocytes were radioiodinated by the lactoperoxidase technique, solubilized in 1% TX-100 and immunoprecipitated using 1 microgram of a specific antibody, i.e. monoclonal antibody βF1 or monoclonal antibody UCHT-1, or 1 microliter of NMS. The immunoprecipitates were then analyzed by 10.5% SDS-PAGE under reducing conditions. The $^{125}$I-labeled molecules were visualized by autoradiography as previously described (28).

Two-colored cytofluorographic analysis was performed by first staining with FITC-OKT®3 monoclonal antibody for 45 minutes at 4° C. After washing, the lymphocytes were fixed in 1% paraformaldehyde for 15 minutes at 23° C. then incubated in 70% ethanol in phosphate buffered saline (PBS) for 5 minutes at −20° C. After further washing, the cells were stained with the biotinyl-βF1 monoclonal antibody followed by PE-avidin. Analysis was performed on an Ortho® cytofluorograph (Ortho Diagnostic Systems, Inc., Westwood, Mass.).

Analysis of cell surface protein molecules associated with T3 molecules on IDP1 and IDP2 cell lines IDP1 cell line 2 (WT31$^+$) and cell line 3 (WT31$^-$) were $^{125}$I-labeled as described above. Radioiodinated, intact lymphocytes were then either cross-linked by incubation in PBS (pH 8) containing 50 micrograms/ml dithio-bis-succinimidyl propionate (DSP) or mock incubated. The cells were then solubilized in 1% TX-100 and immunoprecipitated as previously described (12). T3 associated molecules ($M_r$ 40,000-55,000) in the anti-T3 immunoprecipitations were detected at low levels in the noncross-linked samples and at higher levels in the cross-linked samples.

IDP2 cell line 7 (88% WT31$^-$T3$^+$) was $^{125}$I-labeled and treated with DSP or mock incubated. Immunoprecipitations were performed using NMS, the anti-T3 monoclonal antibody UCHT-1 and the anti-TCR α, β monoclonal antibody βF1 either without or with preclearing TCR α, β molecules with the monoclonal antibody βF1. A small fraction of radiolabeled TCR α, β was detected in samples which were not precleared but not in samples which were precleared with βF1.

IDP2 cell line 5 (WT31$^+$T3$^+$) and cell line 7 (88% WT31$^-$T3$^+$) were $^{125}$I-labeled, solubilized in 1% TX-100 and immunoprecipitated using NMS or the anti-T3 monoclonal antibody UCHT-1. The T3 heavy subunit ($M_r$ 27,000) appeared similar on these two cell lines, while the T3 light subunits ($M_r$ 19,000-25,000) did not.

$^{125}$I-labeling, solubilization in 1% TX-100, immunoprecipitation and visualization after 10.5% SDS-PAGE analysis by autoradiography were performed as previously described (28). Chemical cross-linking was performed for 30 minutes at 23° C. on intact radiolabeled lymphocytes using DSP (50 micrograms/ml) in PBS (pH 8) as previously described (12). After immunoprecipitation, all samples were examined by SDS-PAGE under reducing conditions using 5% 2-mercaptoethanol, which cleaved both the . disulfide bonds between protein subunits and the DSP chemical cross-link Northern blot analysis of RNA isolated from IDP2 cell lines using TCR α, TCR β and TCR γ cDNA probes Total RNA (15 micrograms) isolated from IDP2 cell line 6 (WT31−) and from T leukemic cell line HBP-MLT was fractionated on a 1.5% agarose gel containing 2.2M formaldehyde, transferred to nitrocellulose and hybridized with TCR α, TCR β and TCR γ probes.

Total RNA (3 micrograms) isolated from IDP2 cell line 5 (WT31+T3+), IDP2 cell line 7 (88% WT31−T3+) and HPB-MLT was analyzed as described above.

RNA preparation, electrophoresis, transfer to nitrocellulose and hybridization with $^{32}P$-labeled, nicktranslated probes ($1-3\times10^8$ cpm/microgram) were as described previously (41). α-chain probes were either the human cDNA clones pGA5(8) or L17 α (42). β chain probes were either the human cDNA clones 12A1 (43) or L17 (43). The γ-chain probe was an EcoRI to AccI fragment derived from human cDNA clone Tγ-1 (36). Radioactive bands were visualized by autoradiography using intensifying screens. All probes were labeled to nearly identical specific activity, and identical exposure times are presented.

Immunoprecipitation of IDP2 cell line 7 surface molecules using anti-γ antiserum TX-100 solubilized $^{125}I$-labeled IDP2 cell line 7 (88% WT31−T3+) was denatured (see below) and then immunoprecipitated with NMS or normal rabbit serum and with anti-V γ peptide serum or anti-C γ peptide serum. A specific band was observed at $M_r$ 55,000 in both the anti-V γ and anti-C γ immunoprecipitations. The additional band at $M_r$ 90,000 was not reproducibly observed in the anti-C γ immunoprecipitations (see below).

DSP cross-linked native lysates (1% TX-100) from $^{125}I$-labeled IDP2 cell line 7 were immunoprecipitated with NMS or with the anti-T3 monoclonal antibody UCHT-1. Alternatively, the lysate was denatured (as described below) and immunoprecipitated with either normal rabbit serum or with anti-C γ peptide serum.

An additional aliquot of lysate was subjected to a two stage immunoprecipitation. Polypeptides were immunoprecipitated with the anti-T3 monoclonal antibody UCHT-1, and were eluted from the immunoabsorbent under denaturing and reducing conditions, in order to break the DSP cross-link. Immunoprecipitation from this eluate was then performed using anti-C γ peptide serum.

$^{125}I$-labeling, solubilization in 1% TX-100 and immuno-precipitation were performed as described above. Native lysates (1% TX-100) were denatured by the addition of SDS (final concentration of 1%) and dithiothreitol (final concentration of 2 mM) followed by heating the mixture for 5 minutes at 68° C. After cooling, iodoacetamide was added (20 mM final concentration) and samples were diluted with the addition of 4 volumes of 1.5% TX-100 in Tris buffered saline (pH 8) The initial immunoprecipitate in the experiment was denatured and subsequently partially renatured (28). Samples were immunoprecipitated with 10 microliters of anti-C γ or anti-V γ peptide sera, 1 microgram of UCHT-1 or 1 microliter of NMS or normal rabbit serum and analyzed by 10.5% SDS-PAGE under reducing conditions (5% 2-mercaptoethanol).

Peptides corresponding to deduced V γ or C γ amino acid sequences (residue numbers noted below in the Experimental Result section) were synthesized on a Beckman 990 peptide synthesizer using the method of Erickson and Merrifield (44). Peptide purity was assessed by high pressure liquid chromatography and peptide sequence was confirmed by amino acid analysis. Peptides were coupled to keyhole limpet hemocyanin (KLH) at a ratio of 50 peptides per KLH molecule (45). Mice and rabbits were immunized with the V γ peptides or C γ peptides, respectively. Animals were injected at three week intervals and the antisera screened for binding reactivity on peptide-KLH and peptide-bovine serum albumin conjugates to ascertain the presence of peptide-specific antibodies.

Monoclonal antibodies against the γ chain were generated by standard procedures as described in (47, 50). BALB/c mice were immunized with the KLH-coupled peptide to the variable region γ chain peptide described above using the method of Erickson and Merrifield (44). After four immunizations at two week intervals, spleen cells were fused with P3-X63-Ag8U1 myeloma cells. Positive hybridoma clones were screened and identified by the enzyme immunoassay (EIA) described in (48).

Isolation of DNA sequences of the δ polypeptide from purified proteins DNA sequences of the TCR δ gene may be isolated and determined by strategies utilized to isolate the TCR β gene as described in (49, 50). Briefly, the amino acid sequence of the TCR δ gene may be determined following isolation of the TCR δ polypeptide which is described hereinafter After the amino acid sequence is determined, short, synthetic DNA sequences may be prepared using a commercial DNA synthesizer (Applied Biosystems, Inc., Foster City, Calif.). The synthetic DNA sequences may be used as probes for the isolation of the complete sequence of DNA from a cDNA library of cell lines containing the TCR polypeptide The primary structure of the protein may then be determined (51).

Preparation of monoclonal antibodies against the δ polypeptidesand against γ, δ complexes Monoclonal antibodies against the δ polypeptide may be generated by standard procedures (47, 50). Peptides derived from the TCR δ polypeptide may be prepared from nucleic acid sequences determined by the methods described above. Methods for the selection of such peptides useful for immunization have been described in detail (55, 56, 57).

Monoclonal antibodies directed against γ, δ complexes may be prepared according to published procedures (47, 50). γ, δ complexes may be isolated from the T cell lines described above and used to immunize BALB/c mice as described in previously published procedures (28). Alternatively, BALB/c mice may be immunized with cell lines, e.g., the IDP1 cell line or the IDP2 cell line.

Methods for the fusion, generation and maintenance of hybridoma cell lines have been widely published and are known to those skilled in the art. Hybridoma cells that produce monoclonal antibodies which are directed against specific TCR γ, δ cell lines but which do not cross react with other T cell lines may be selected and recovered.

Immunoprecipitations of TCR γ, δ and T3 from a human tumor and peripheral blood lymphocyte lines Viable lymphocytes were isolated by Ficoll-Hypaque density gradient centrifugation and $2\times10^7$ cells were radio-iodinated by the lactoperoxidase technique as described (28). Labelled cells were lysed in 5 ml of TBS (10 mM Tris pH 8, 140 mM NaCl) with 0.3% 3-[(3-cholamidopropyl) dimethylammonio]-1-propanesulphonate (CHAPS), which preserves the TCR-T3 association (64), containing 2 mM phenyl methylsulphonyl fluoride (PMSF) and 8 mM iodoacetamide (IAA). Immunoprecipitation was carried out using fixed *Staphylococcus aureus* Cowan I (SACI) as described (12), and the immune complexes were washed x 5 in TBS containing 0.1% Triton X-100 (TX-100). Reduced samples were boiled in 2 mM dithiothreitol (DTT) and all samples incubated for 10 min at 23° C. in 10 mM IAA before analysis by SDS-PAGE. Immunoprecipitations using anti-C γ sera were performed on 1% TX-100 lysates that were dialysed to remove IAA and then denatured by the addition of one tenth volume of sodium dodecyl sulfate (SDS) containing 3 mM DTT with boiling for 3 min. After partial renaturation by the addition of 4 vols of 1.5% TX-100 in TBS containing 30 mM IAA, anti-C γ sera or NRS were added and the immunoprecipitates were washed in TBS containing 0.5% TX-100, 0.5% deoxycholate, 0.05% SDS before analysis by SDS-PAGE. Rat anti-mouse δ chain-specific mAb 187.1 15 μg) was added as a second antibody to provide protein A binding of $IgG_I$ mAb βF1, UCHT and P3 (53).

Northern blot analysis of RNA isolated from PBL C1

Approximately 1.5 μg RNA was loaded per lane, probes were labeled to similar specific activity, and identical autoradiographical exposures are presented. RNA sizes were determined based on previously published lengths for TCR β and TCR γ transcripts (36, 4).

Two-dimensional gel analysis of TCR γ polypeptides and precursors

After radioiodination with lactoperoxidase, lymphocytes were treated with 100U of neuraminidase (Gibco) in phosphate-buffered saline (PBS) 1 mg $ml^-$ bovine serum albumin, 1 mg $ml^1$ glucose for 90 minutes at 23° C., washed in PBS and solubilized in 0.3% CHAPS. Immunoprecipitates were prepared as in FIG. 1 and NEPHGE (charge separation) was carried out using pH 3.5–10 ampholines (LKB, Sweden), or IEF using pH 3.5–10, 4–6, 9–11 ampholines (2:15.5:1.5) followed by 10.5% SDS-PAGE gels for size separation as described (12). NEPHGE was carried out (A,B) applying the iodinated IEF sample at the acidic end, while IEF (C,D) was carried out for 20 hours at 400V applying the sample at the other (basic) end. Brackets enclose the T3-associated species.

Cells ($2\times10^7$) were preincubated for 1 hour at 37° C. in 4 ml methionine-free RPMI 1640 supplemented with 10% fetal bovine serum. $^{35}$S-methionine was added to 250 μCi $ml^{-1}$ and incubation was continued for 1 hour at 37° C. Cells were collected, washed and lysed 0.4 ml of boiling solution of 1% SDS, 10 mM Tris-HCl (pH 8.0), 0.1 mM pMSF and 10 mM IAA Lysates were diluted with 1.6 ml of 2.5% Nonidet-P40, 1% gelatin, 10 mM Tris-HCl (pH 8) and 0.2 ml of 1 mg $ml^{-1}$ DNase. 0.5 mg $ml^{-1}$ RNase, 0.5M Tris-HCl (pH 7), 50 mM $MgC_2$ and incubated at 0° C. for 2–4 hours After centrifugation for 15 minutes at 12,000×g to pellet insoluble debris, immunoprecipitations with anti-γ serum were performed using protein A sepharose preincubated with 1% gelatin and washing as described (65). Elution from the immunoabsorbent and treatment with endo-H (Miles Scientific, Naperville, Ill.) were as described (65). Samples were analyzed with anti-serum by two-dimensional gel electrophoresis employing NEPHGE in the first dimension and 10% SDS-PAGE in the second dimension, followed by fluorography (66).

Rearrangements of the γ and β genes in T cells expressing the TCR γ polypeptides Genomic DNA was isolated as described (BamHI or EcoRI), size-fractionated on 0.7 & agarose (BamHI digests) or 0.9% agarose (EcoRI digest), and transferred to nitrocellulose as described (67). Filters were hybridized to a nick-translated $^{32}$P-labelled 0.8 kb HindIII-EcoRI $J_{\gamma\ 1,3}$ probe (20) or a 1.1 kb EcoRI-HindII $C_{\beta 2}$ probe (68). Filters were washed in 2*x* SSC and 0.1% SDS followed by 0.2% SSC and 0.1% SDS at 55° C. before autoradiography with intensifying screens.

Cytolysis by IDP2 and PBL C1 cells

Cytolytic assays were performed in round-bottom 96-well tissue culture plates with $^{51}$Cr-labelling, harvesting and calculation of % specific release as described (34). IDP2 or PBL C1 cells were either preincubated with UCHT1 (1:300 dilution) (+anti-T3) for 30 minutes at 0° C., washed x 3 or mock incubated and placed together with labelled target cells. Anti-HLA Class I and Class II mAb anti-T3 mAb were placed in wells containing the $^{51}$Cr-labelled MOLT 4 cells for 30 minutes at 0° C., then IDP2 cells were added at a 40:1 E:T ratio. All samples were assayed in triplicate, each experiment was performed at least three times, and one representative experiment of each is shown in FIG. 9.

Experimental Results

Figure 1B:
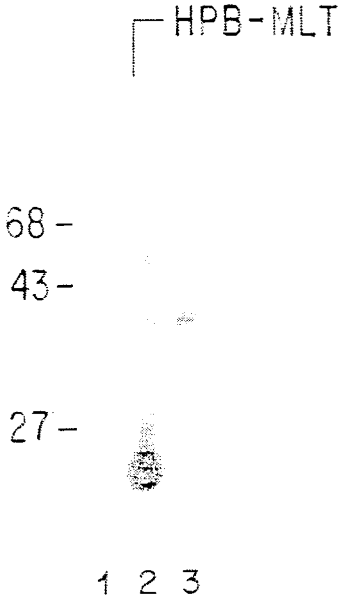
Figure 1C:
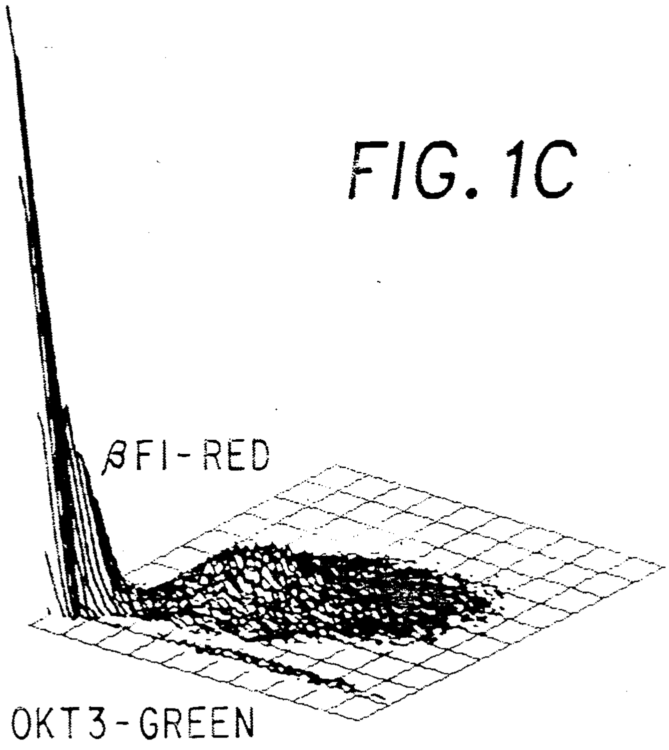

A murine framework antiserum that recognizes the majority of human TCR α, β molecules has previously been reported (28). Subsequently, a murine monoclonal antibody, designated Framework 1 (βF1), that is reactive with shared determinants on the human TCR β chain was obtained (46). The βF1 monoclonal antibody reacts with majority of T3 positive ($T3^+$) human peripheral blood lymphocytes (PBLs) and is capable of immunoprecipitating the TCR α, β heterodimer from all human T cell lines examined that have α, β T cell receptors and express the I′ 3 glycoprotein. Immunoprecipitations from a panel of T cell lines using this monoclonal antibody demonstrate this reactivity as well as the heterogeneity of the TCR α and TCR β subunits from different receptors (FIG. 1A). Like the framework antiserum (28), this monoclonal antibody does not stain the surface of living T cells, but will specifically react with both membrane and cytoplasmic T cell receptors after partial solution of the lymphocyte plasma membrane with 70% ethanol. Double staining of human PBLs with a fluorescein-anti-T3 monoclonal antibody and a biotinyl-βF1 monoclonal antibody followed by PE avidin reveals that the βF1 monoclonal antibody recognizes 95–97% of peripheral blood $T3^+$ lymphocytes However, it clearly defines a small population of T lymphocytes that is βF1 negative (βF1), yet $T3^+$ (FIG. 1C).

A second framework monoclonal antibody designated WT31, initially thought to recognize the T3 antigen (29), has recently been shown to react with a common epitope of human TCR α, β (30). While double staining with an anti-T3 monoclonal antibody (OKT®3) and WT31 revealed that each of these monoclonal antibodies cross-block binding of the other, one-color fluorescence indicated that WT31 typically recognized 1-3% fewer cells in peripheral blood than do anti-T3 monoclonal antibodies. The WT31 monoclonal antibody efficiently binds to the surface of T cells (such as in FACS analyses) and is capable of immunoprecipitating the TCR α, β molecules, albeit inefficiently, from radio labeled detergent lysates (30) (FIG. 1B, lane 3). Thus, the βF1 monoclonal antibody and the WT31 monoclonal antibody appear to recognize all but a small fraction of human peripheral blood T3+ cells, and define a subpopulation that is T3+ but unreactive with both of these framework monoclonal antibodies against the TCR α, β molecules. Evidence that the T3+ lymphocytes that are unreactive with the monoclonal antibody βF1 are also unreactive with the monoclonal antibody WT31 is shown below. WT31 was used primarily for FACS analyses and βF1 was used primarily for immunoprecipitation studies.

Efforts at growing the WT31−T3+ population from normal adult PBLs proved difficult, since the WT31+T3+ lymphocytes usually overgrew the WT31−T3+ cells following mitogenic stimulation. However, growth of the WT31−T3+ population from the PBLs of immunodeficiency patients was successful. Immunodeficiency patient 1 (IDP1) suffered from the bare lymphocyte syndrome and lacked class II MHC antigen expression on lymphoid cells (31, 32), while immunodeficiency patient 2 (IDP2) suffered from an ectodermal dysplasia syndrome (33) and displayed poor in vitro T cell proliferative responses to mitogens.

After activation of PBLs from IDP1 with alloantigen and propagation in conditioned media containing interleukin-2 (IL-2) activity (34),the resultant cell line was observed to be approximately 50% WT31+T3+ and 50% WT31−T3+ (see Table I below, cell line 1). Subsequent sorting of this cell line yielded homogeneous populations of WT31+T3+ cells and WT31−T3+ cells (see Table I below, cell lines 2 and 3, respectively).

TABLE 1

| CELL LINE NUMBER | SOURCE | CELL LINE[1] DESCRIPTION | % POSITIVE WT31 | T3 | T4 | T8 |
|---|---|---|---|---|---|---|
| 1 | IDP1 | allo | 50 | 100 | 11 | 50 |
| 2 | IDP1 | WT31+ sort | 100 | 100 | 70 | 28 |
| 3 | IDP1 | WT31− sort | 0 | 100 | 0 | 62 |
| 4 | IDP2 | fresh PBL | 61 | 63 | 38 | 16 |
| 5 | IDP2 | PHA | 100 | 96 | 18 | 80 |
| 6 | IDP2 | allo | 2 | 100 | 0 | 43 |
| 7 | IDP2 | PHA | 12 | 93 | 1 | 18 |

[1]Cell line description indicates the conditions for activation or source of lymphocytes. WT31+ and WT31− sorted cell lines 2 and 3 (sort) were obtained by fluorescence activated cell sorting of IDP1 cell line 1.

Cell lines were also obtained from IDP2. Fresh PBLs from IDP2 revealed that 63% of the PBLs were T3+ and 1-3% fewer cells (61%) were WT3+, which is typical of normal PBLs (Table I, cell line 4). Activation of these IDP2 PBLs with either phytohemagglutinin (PHA) or alloantigen and propagation in vitro with conditioned media resulted in several cell lines. These included a homogeneous WT31+T3+ cell line (Table I, cell line 5), a homogeneous WT31−T3+ cell line (Table I, cell line 6) and on a third occasion, a cell line that was 88% WT31−T3+ (with 12% contaminating WT31+T3+ cells) Table I, cell line 7). The WT31−T3+ population contained both T4−T8+ and T4−T8− cells (Table I, cell lines 3, 6 and 7). Further phenotypic analysis revealed that this population was T11+ but negative for natural killer cell markers such as Leu 7, Leu 11 and OKM1 and for the immature thymocyte marker T6.

Figure 2A:
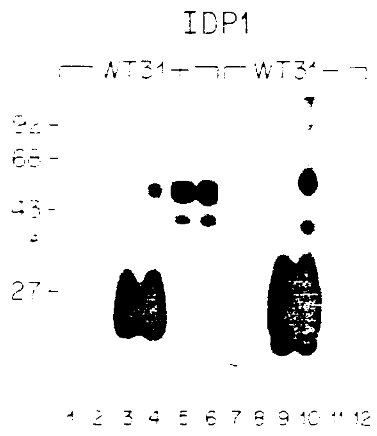
Figure 2B:
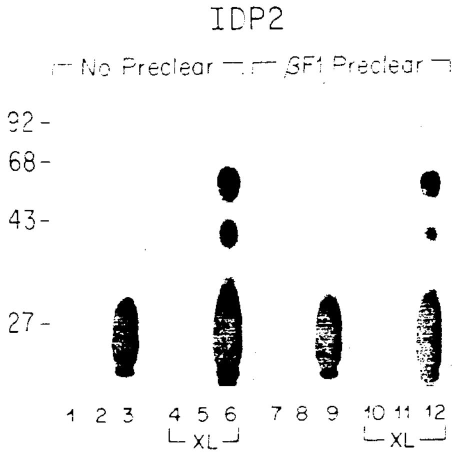
Figure 2C:

The βF1 monoclonal antibody immunochemically defined a heterodimeric structure on the surface of $^{125}$I-labeled WT31+T3+ IDP1 lymphocytes (FIG. 2A, lane 5), yet failed to recognize a similar protein on the WT31−T3+ population from this same individual (FIG. 2A, lane 11). Similar analysis of IDP2 cell lines revealed a trace of TCR α, β on the 88% WT3−T3+ cell line γ (FIG. 2B, lane 2) consistent with the 12% contamination with the WT31+T3+ cells. Thus, the WT31−T3+ cells, identified by the lack of cell surface reactivity with the WT31 monoclonal antibody in FACS analysis, were also βF1−, as determined by the lack of TCR α, β on immuno-precipitation. All WT31+T3+ and WT31−T3+ cell lines expressed similar amounts of T3 by FACS analysis and by immunoprecipitation with an anti-T3 monoclonal antibody (FIG. 2A, lanes 3 and 9; FIG. 2C, lanes 2 and 4). However, the T3 molecule found on WT31−βF1−T3+ lymphocytes was not identical to the T3 molecule found on WT31+βF1[30]T3+ cells by SDS-PAGE. One-dimensional (FIG. 2C) and two-dimensional gel analysis indicated that the difference in T3 was restricted to the light T3 subunits, which reproducibly displayed different SDS-PAGE mobilities (FIG. 2C, arrowhead).

Figure 3A:
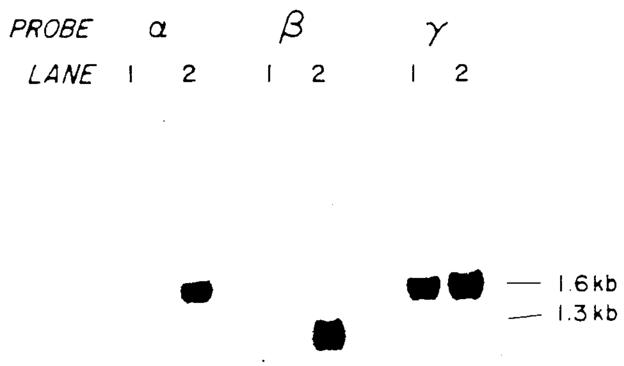
Figure 3B:
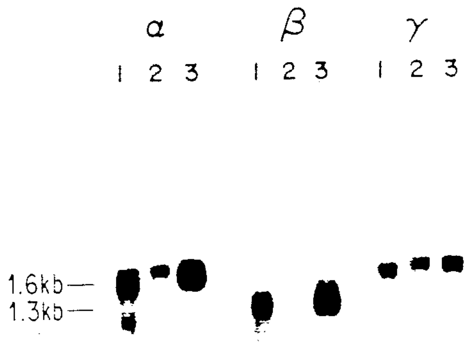

To determine if the WT31−βF1 −T3+ population lacked TCR α, β molecules, or alternatively expressed TCR α, β molecules that failed to react with these monoclonal antibodies, the presence of mRNAs encoding the TCR α and β proteins was investigated. $^{32}$P-labeled cDNA clones encoding TCR α, TCR β, and TCR γ were used to probe Northern blots containing whole cell RNA from WT31−βF1−T3+ and WT31+βF1+T3+ IDP2 cell lines and from HPB-MLT, which is known to contain mRNA for TCR α, TCR β and TCR γ. No TCR α or TCR β mRNA transcripts could be detected in the RNA from the WT31−βF1−T3+ IDP2 cell line 6 (FIG. 3A- probe, lane 1; or β-probe, lane 1), whereas expression of both was clearly detectable in RNA from HPB-MLT (FIG. 3A α-probe, lane 2; and β-probe, lane 2) Notably, TCR γmRNA was present in the WT31−T3+ cells at levels comparable to that in HPB-MLT (FIG. 3A γ-probe, lanes 1 and 2). Thus, the WT31− βF1−T3+ lymphocytes lacked TCR α and γ mRNA. Subsequent experiments on cell lines that were mostly WT31−T3+ corroborated these results. For example, Northern blot analysis performed on IDP2 cell line γ (88% WT31−T3+) and compared with IDP2 cell line 5 (WT31+T3+), as well as with HPB-MLT cells, revealed only a trace of TCR or TCR β mRNA in the 88% WT31−T3+ cells (consistent with the 12% contamination with WT31+T3+ cells) (FIG. 3B, lane 2 for each probe). Further, the majority of the β transcripts that could be detected were 1.0 and not 1.3 kb and were probably nonfunctional (35). In contrast, the IDP2 cell line 5 (WT31+T3+) expressed levels of both RNA species which were comparable to HBP-MLT (FIG. 3B, lane 1 for each probe). However, like the WT31−T3+ cell line shown in FIG. 3A, both the WT31−T3+ and the WT31+T3+ cell lines showed TCR γ RNA levels comparable to HPB-MLT (FIG. 3B γ-probe). Thus, the WT31−T3+ cells lacked α and β T cell receptor mRNA (Northern analysis) and α and β T cell receptor proteins (immunoprecipitation and FACS analysis). The presence of γ mRNA in WT31−T3+cells, while consistent with T γ protein expression, could not be taken as strong evidence for this, since many human cell lines that express T γ mRNA of normal size may express full length transcripts that are out of frame due to defective V-J joining (36).

To determine if proteins analogous to the TCR α, β molecules existed on the WT31−βF1−T3+ cells, the technique of chemical cross-linking was utilized. This procedure has been used to shown directly the physical association of the TCR α, β molecules with the T3 glycoprotein (12). The bifunctional, cleavable reagent, dithio-bis-succinimidyl propionate (DSP) was employed to cross-link $^{125}$I-labeled surface proteins of viable T lymphocytes After cross-linking, the lymphocytes were solubilized in a non-ionic detergent and immunoprecipitated with an anti-T3 monoclonal antibody. As expected, the WT31+βF1+T3+ lymphocytes revealed that the TCR α and β chains were cross-linked to T3. For example, TCR α, β molecules and T3 were found in anti-T3 or βF1 monoclonal antibody immunoprecipitates from cross-linked IDP1 cell line 2 (WT31+T3+) (FIG. 2A, lanes 4 and 6). However, despite the lack of reactivity with the βF1 monoclonal antibody and lack of TCR α or TCR β mRNA, IDP1 cell line 3 (WT31−T3+) and IDP2 cell line γ (88% WT31−T3+) both expressed two protein subunits ($M_r$ 55,000 and 40,000) that specifically cross-linked to T3 (FIG. 2A, lane 10; FIG. 2B, lane 6). The mobilities of these T3 associated molecules were clearly different from those of the TCR α and β chains from WT31+T3+ cell lines (compare FIG. 2A, lanes 4 and 10; or FIG. 2B, lanes 5 and 6).

Since IDP2 cell line γ (88% WT31−T3+) contained 12% WT31+T3+ cells, accounting for the weak βF1 immunoprecipitates noted (FIG. 2B, lane 2), the lysate from these cells was precleared of TCR α, β protein using the βF1 monoclonal antibody. After preclearing, no residual βF1 reactive material could be detected (FIG. 2B, lanes 8 and 11). When this βF1- precleared lysate from cross-linked cells was immunoprecipitated with an anti-T3 monoclonal antibody, $M_r$ 55,000 and 40,000 subunits were still detected (FIG. 2B, lane 12).

Since these WT31−βF1−T3+ cell lines display undetectable levels of TCR α and TCR β mRNA, the molecules found specifically cross-linked to T3 on their cell surfaces cannot represent proteins encoded by the known TCR β or TCR genes.

cDNA clones representing the rearranging human TCR γ gene would encode a polypeptide with a predicted molecular weight of 40,000 daltons (36). However, unlike the murine TCR γ gene, which does not reveal any N-linked glycosylation sites (15), the human TCR γ gene reveals five potential sites for N-linked glycosylation, four of which are located in the constant region (36). Since a TCR γ protein has not previously been isolated, it is not known how many of these potential sites may be used. However, a fully glycosylated human TCR γ protein may have a $M_r$ of about 55,000. The heavy chain of the non-α-non-βT3-associated subunits identified on the WT31−βF1−T3+ IDP1 and IDP2 cell lines has a relative mobility on SDS-PAGE of 55,000 daltons (FIG. 2A and 2B).

Figure 4A:
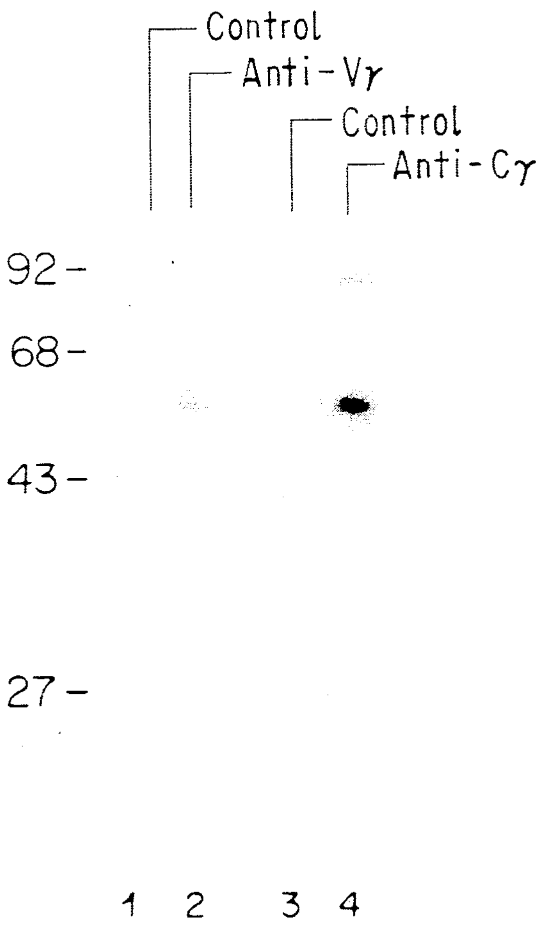

In order to determine if this T3-associated heavy chain was serologically cross-reactive with or identical to the TCR γ protein, antisera were raised to a synthetic peptide having the sequence:

RTKSVTRQTGSSAEITC (representing a 17 amino acid stretch of residues 5–21 from the variable region; anti-V γ peptide serum) and to a synthetic peptide having the sequence:

DKQLDADVSPKPTIFLPSIA (representing a 20 amino acid stretch of residues 117–136 from the constant region; anti-C γ peptide serum) of the TCR amino acid sequence deduced from a human cDNA clone (36). Both the anti-C γ peptide serum and anti-V γ peptide serum immunoprecipitated a molecule with $M_r$ 55,000 from the denatured lysate of $^{125}$I-labeled WT31−βF1−T3+ cells (FIG. 4A, lanes 2 and 4). Such molecules could not be immunoprecipitated from lysates of $^{125}$I-labeled HPB-MLT cells, which express only nonfunctional TCR γ mRNA (36).

Figure 4B:
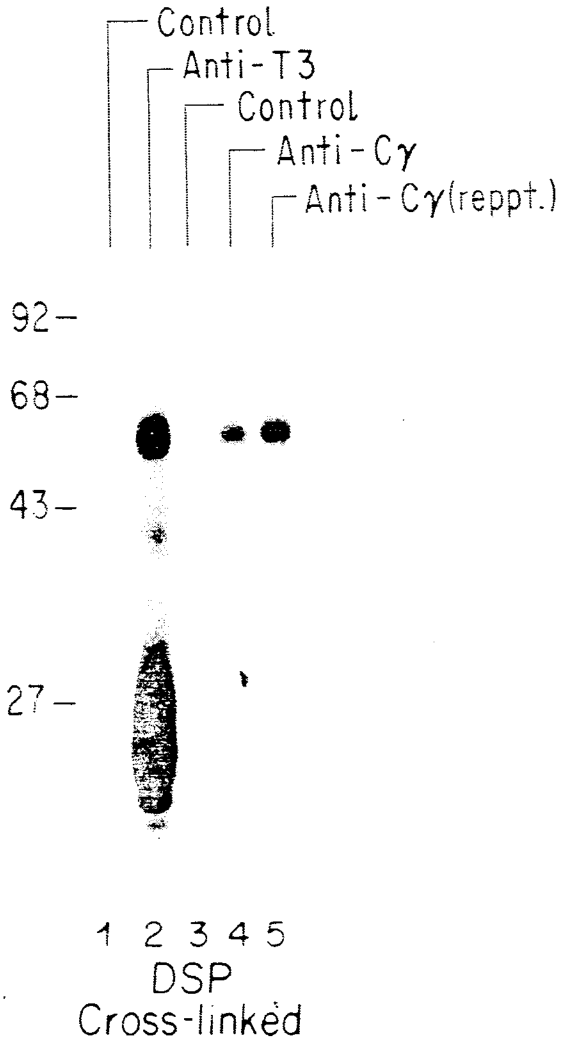

To demonstrate that the 55,000 dalton molecule immunoprecipitated by the anti-C γ and anti-V γ peptide sera was, in fact, &:he heavy chain subunit that cross-linked to T3, an additional experiment was performed (FIG. 4B). A sample of DSP cross-linked lysate from the WT31−βF1−T3+ cells was first immunoprecipitated with an anti-T3 monoclonal antibody, again demonstrating the presence of $M_r$ 55,000 and 40,000 subunits associated with T3 (FIG. 4B, lane 2). In parallel, another aliquot of the cross-linked lysate was immunoprecipitated with an anti-T3 monoclonal antibody, and the immunoprecipitated T3 cross-linked polypeptides were eluted from the immunoabsorbent under denaturing and reducing conditions in order to break the DSP cross-link. This eluate was then re-precipitated with anti-C γ peptide serum. The $M_r$ 55,000 subunit that cross-linked to T3 was re-precipitated by anti-γ peptide serum (FIG. 4B, lane 5), indicating that the $M_r$ 55,000 subunits defined by these two approaches were identical.

Figure 5A:
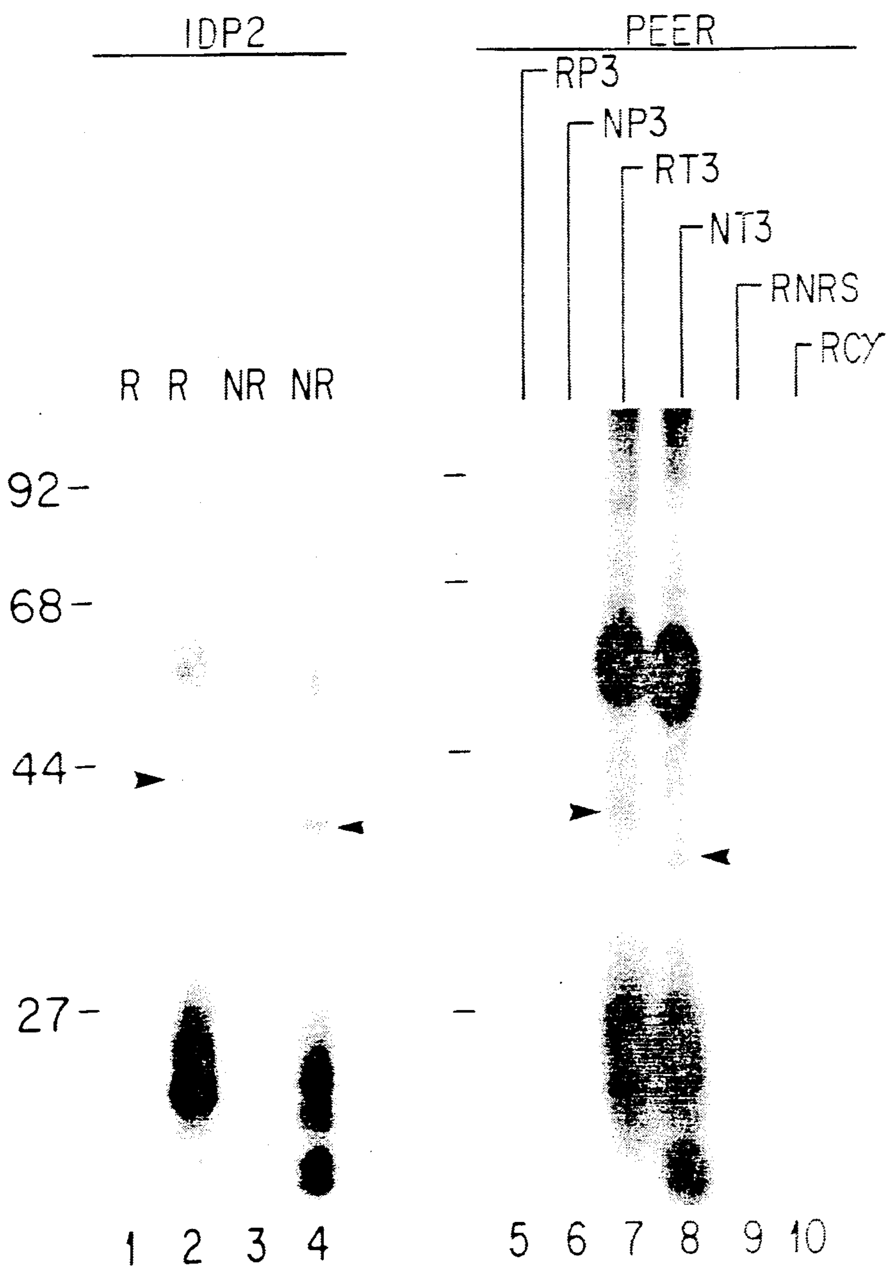

Immunoprecipitations from lysates of surface-iodinated IDP2 lymphocytes using anti-T3 xrAb. (under conditions that do not dissociate TCR subunits from T3, see FIG. 5) yielded two species (55K and 40K) in addition to the T3 subunits (FIG. 5A). This result is identical to the one reported previously using chemical cross-linking The 55K species was shown to react specifically with anti-C γ and anti-V γ peptide sera. The 40K polypeptide was unreactive with these anti-γ peptide sera and is thus likely to represent a non TCR α, β or γ subunit, namely δ. To determine if these subunits are covalently linked, like the TCR α and β subunits, the T3 co-immunoprecipitated polypeptides were examined under reducing and nonreducing conditions. In striking contrast to the TCR α, β subunits, which exist in a heterodimeric disulphide-linked form under nonreducing conditions, the TCR γ and δ subunits on the IDP2 cell line are not covalently linked (FIG. 5A). A small increase in relative mobility on SDS-polyacrylamide gel electrophoresis (PAGE) under nonreducing conditions was observed for the diffuse, heavily glycosylated (see below) TCR γ, whereas a dramatic increase in mobility was observed for the δ subunit, suggesting the presence of one or more intrachain disulphide loops (compare species at arrows, lanes 2 and 4).

Weiss, et al. suggested that the PEER cell line might express the TCR γ polypeptide since it lacked expression of TCR mRNA yet expressed a T3-associated 55–60K polypeptide (69). On further examination, this cell line was found to lack reactivity with a mAb recognizing framework determinants on the TCR β chain, βF1 (FIG. 5A) and to express a strongly iodinated 38K polypeptide. The 55–60K polypeptide was specifically immunoprecipitated with anti-C γ peptide sera and thus appears to represent a further example of the TCR γ protein (FIG. 5A). The TCR γ and δ polypeptides on PEER were of similar size to those on the IDP2 cell line and similarly were not disulphide-linked. Like the δ subunit on IDP2 cells, the counterpart molecule on PEER underwent a marked shift in SDS-PAGE mobility when compared under reducing and nonreducing conditions (compare species at arrows, lane γ and 8). Thus the IDP2 and the PEER cell lines appear to express similar types of TCR γ, δ —T3 complexes, in which the TCR γ and δ subunits are not covalently linked.

Figure 5B:
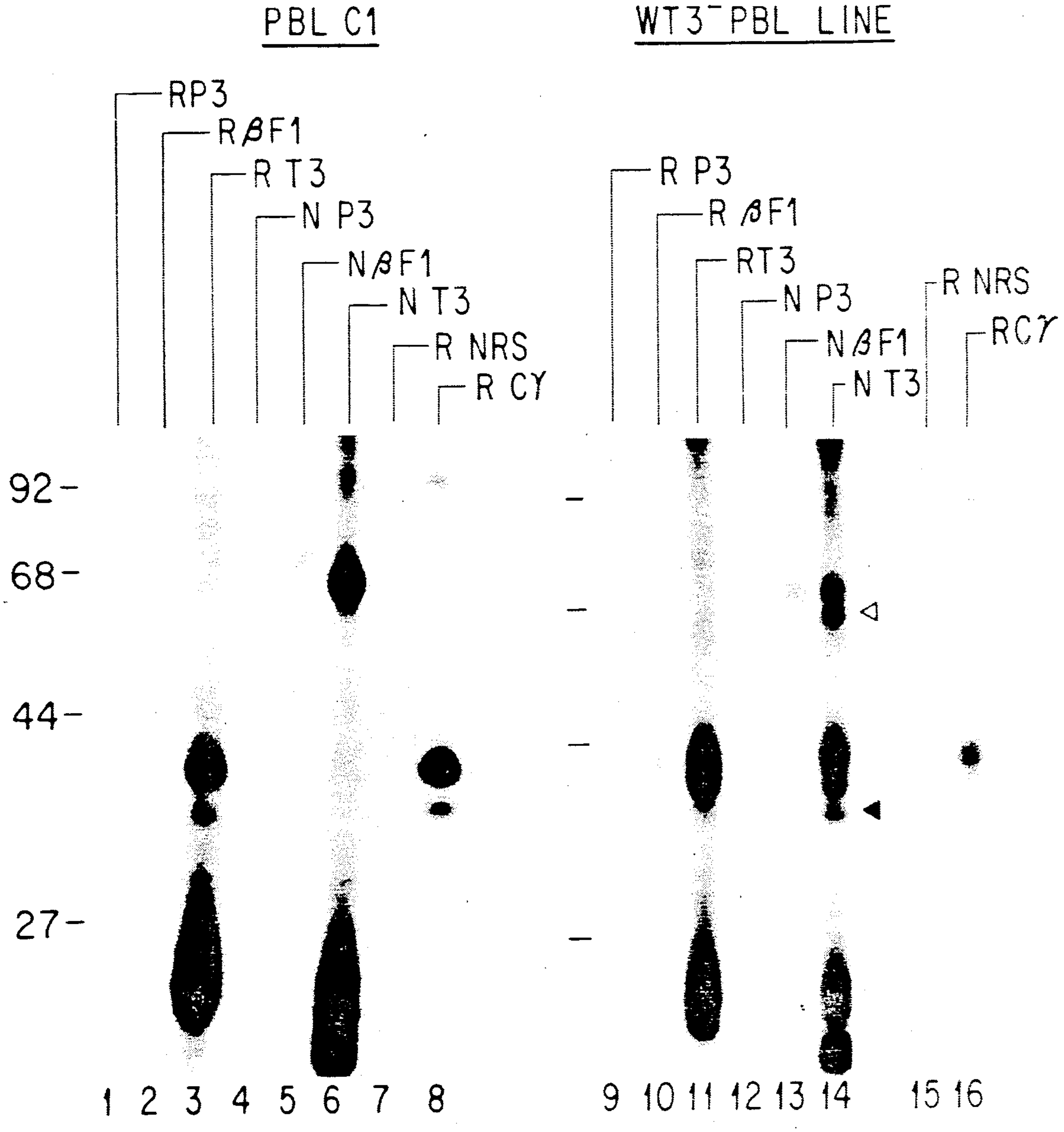

We wished to determine if this second TCR was also expressed as a component of the T cell population in normal peripheral blood. Two-color cytofluorographic analysis comparing staining of human peripheral blood lymphocytes (PBL) with mAb βF1 and OKT®3 showed a discrete population representing 2–5% of the $T3^+$ PBL that appeared to be TCR α, β negative. To examine this lymphocyte population, normal adult PBL were subjected to cytofluorographic cell sorting after staining with mAb WT31. Unstained PBL were isolated and propagated in vitro in IL-2-containing conditioned media receiving biweekly additions of irradiated autologous feeder cells and phytohemagglutinin (PHA-P). The cell line derived, $WT31^-PBL^-$ LINE was cloned by limiting dilution with plating at 0.5 cell well and the cloned cells were propagated as for the polyclonal cell line. Several such peripheral blood derived T cell clones were obtained, and PBL Clone (PBL Cl) was studied in detail. By cytofluorographic analysis, this clone was $T3^+T11^-$ but $T4^-T8^-$ and WT31- The expression of TCR α, β and γ mRNA from PBL Cl was determined by Northern blot analysis (FIG. 6). By comparison with the $WT31^+\beta F1^+T$ cell tumor HPB-MLT, only very low levels of TCR α and β mRNA were detected. In contrast, abundant TCR γ mRNA was noted (FIG. 6 γ probe); interestingly, the TCR γ mRNA was slightly smaller than the 1.6 kilobase (kb) message found in HPB-MLT and in the TCR γ-expressing IDP2 cell line (FIG. 6). Consistent with these observations, WT31 reactivity was not detected in cytofluorographic analysis (data not shown) and only scant levels of TCR α and β polypeptides were found by immunoprecipitation using mAb βF1 (FIG. 5B, lanes 2, 5). In contrast it is likely that the trace levels of TCR α and β protein detected in PBL Cl are accounted for by the 1–2% contamination with irradiated autologous feeder cells used in the propagation of this clone. Two abundant chains (40K and 36K) were observed associated with T3 under reducing conditions in SDS-PAGE analysis (FIG. 5B, lane 3). Anti-C γ sera immunoprecipitated both of these polypeptides from reduced and denatured PBL Cl lysates (FIG. 5B, lane 8).

To determine if these 40K and 36K TCR γ polypeptides were part of a disulphide-linked dimer, coimmunoprecipitations with anti-T3 were examined under nonreducing conditions. A single band of $M_r$ (70K) was observed indicating that, unlike IDP2 and PEER cells, PBL Cl expresses a T3-associated TCR γ product that is part of a disulphide-linked dimeric complex.

Figure 7A:
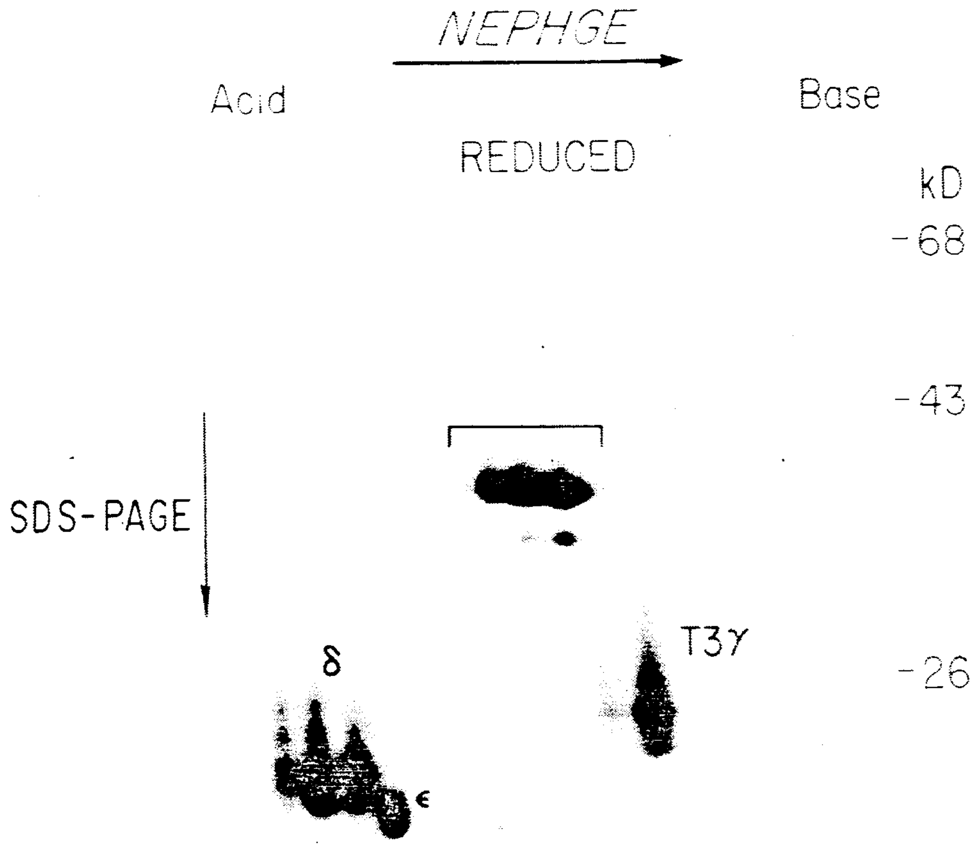

As a TCR γ partner (δ) was present on the non-disulphide linked form of this receptor complex on IDP2 and PEER cells, we examined whether the disulphide-linked form of the receptor on PBL Cl was composed of a homo- or a heterodimer. Immunoprecipitates were analyzed by two-dimensional gel electrophoresis (nonequilibrium pH gel electrophoresis (NEPHGE) followed by SDS-PAGE; FIG. 7A, B). Under reducing conditions, both the TCR γ species (40K and 36K) were found to have identical charges, and displayed heterogeneity typical for a sialylated glycoprotein. These characteristics are like those described previously for differentially glycosylated TCR polypeptides having the same amino-acid backbone. Thus, these species may represent differentially glycosylated forms of the same TCR γ peptide. This conclusion is supported by the results of metabolic pulse-labelling (below) which reveal only a single precursor TCR γ species in PBL Cl.

Figure 7B:
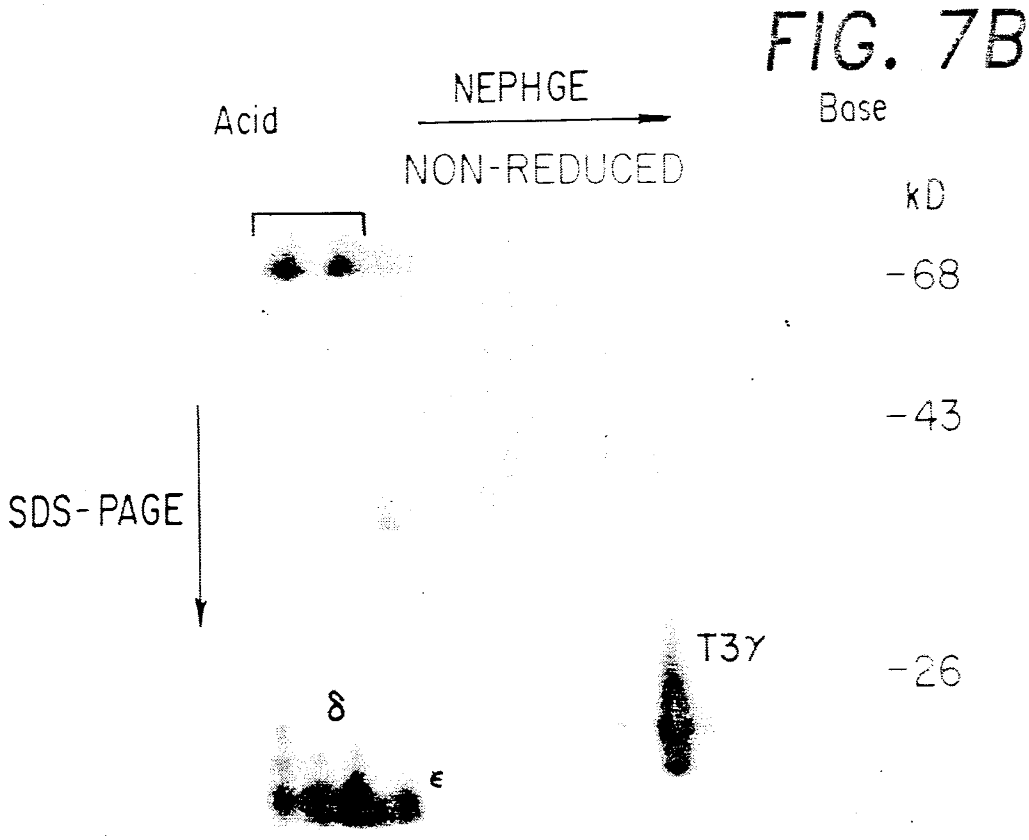
Figure 7C:
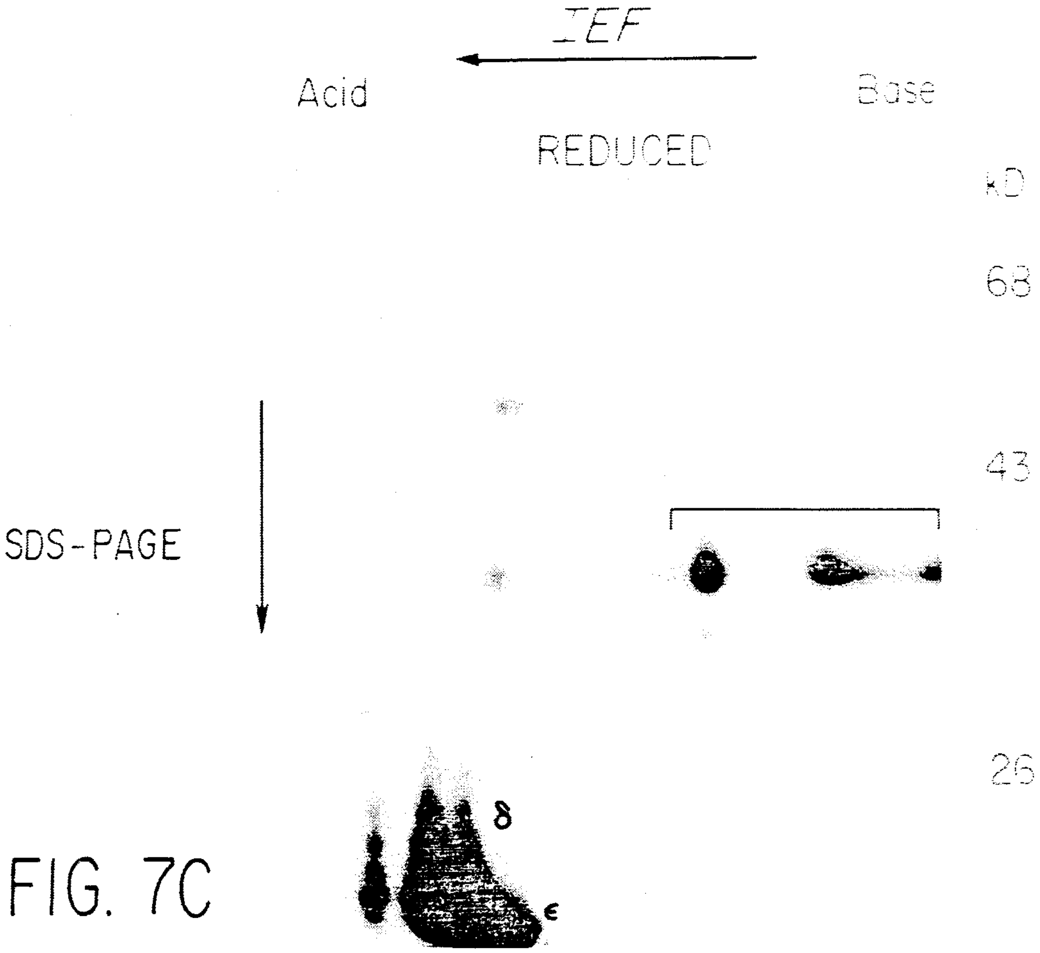
Figure 7D:
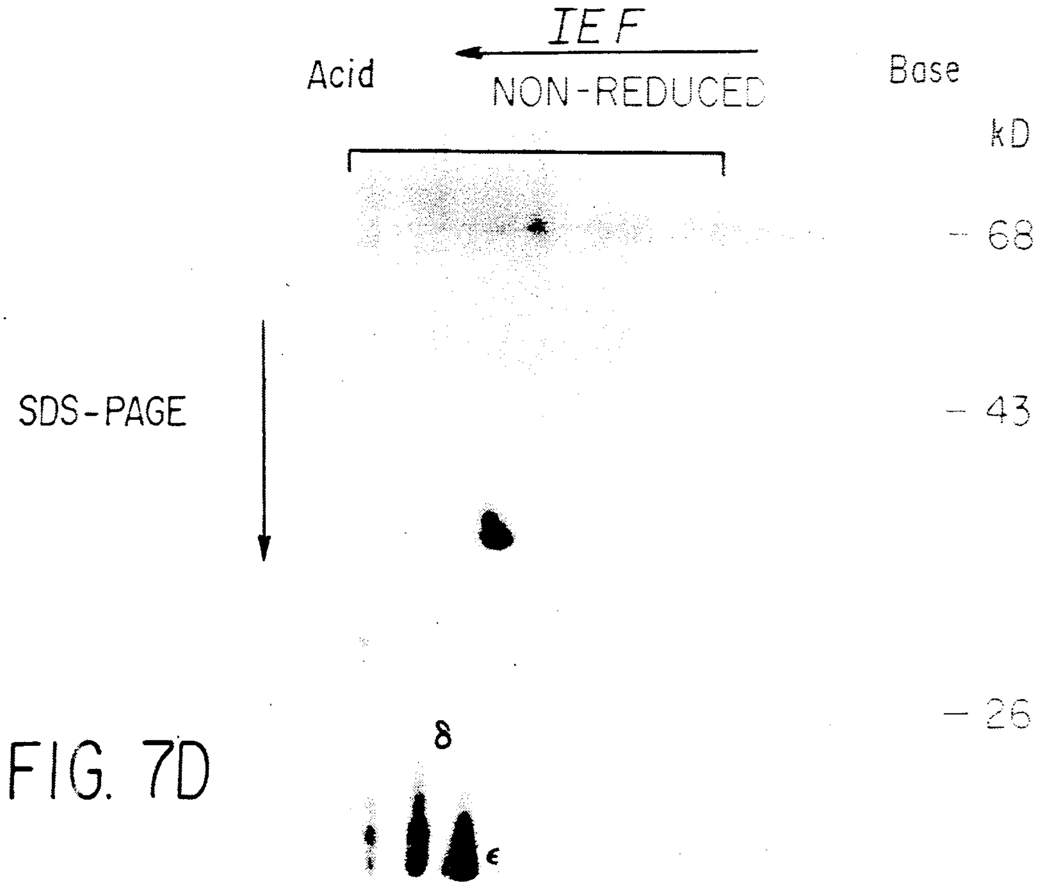

A disulphide-linked dimer composed of one or both of these TCR γ species should have a focusing position similar to either of the two components alone when analyzed by NEPHGE or equilibrium isoelectric focusing (IEF). But a heterodimer composed of TCR γ a distinct polypeptide might have a different charge and focusing position. The position of the disulphide-linked dimer was therefore examined by carrying out NEPHGE under nonreducing conditions, followed by SDS-PAGE under nonreducing conditions (FIG. 7B). Strikingly, the position of the disulphide-linked dimer was substantially more acidic than that of the TCR polypeptides examined under reducing conditions (compare the 40K and 36K species in FIG. 7A with the 70K species in FIG. 7B). This result suggests that the TCR γ species were covalently linked to a polypeptide of distinct NEPHGE mobility. Thus, although a TCR γ partner could not be directly visualized (either because it was inadequately labelled with $^{125}I$ or because it did not resolve in the focusing system used here), the TCR γ polypeptide on PBL Cl appeared to be expressed as a part of a disulphide-linked heterodimer. Experiments using equilibrium IEF (rather than NEPHGE) confirmed this observation (FIG. 3D).

Figure 7E:
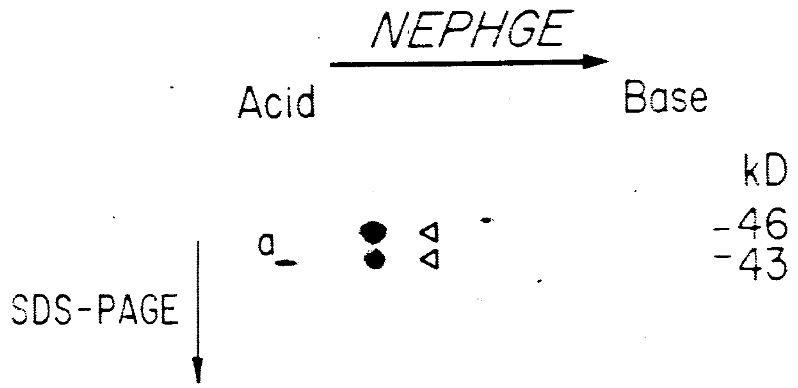
Figure 7F:
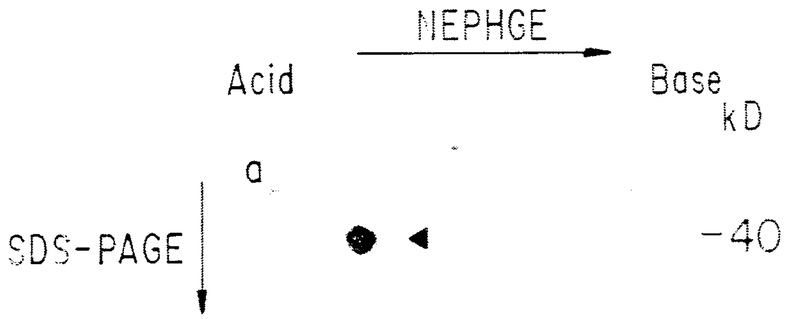
Figure 7G:
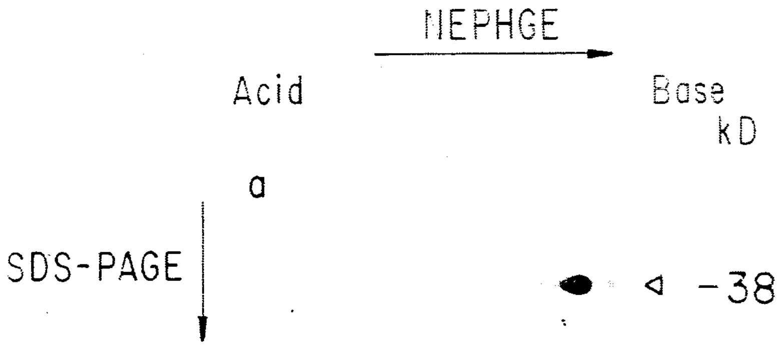
Figure 7H:
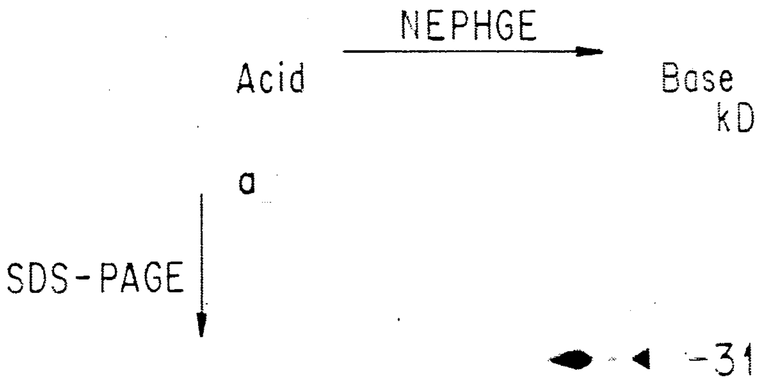

A further distinction between the disulphide-linked and non-linked forms was the size of the mature TCR γ glycopeptide (55–60K on IDP2 and PEER versus 40K and 36K on PBL Cl). To assess how much of this radical size difference is due to differential glycosylation and how much to different peptide backbones, TCR peptides were analyzed in cells pulse-labelled with $^{35}S$-methionine After solubilization under denaturing and reducing conditions, the lysates were immunoprecipitated with anti-C γ sera and examined by two-dimensional gel electrophoresis (FIG. 7E–H). Immunoprecipitates were either treated with endoglycosidase H (endo-H) to remove immature high-mannose glycans from pulse-labelled material, or were mock treated. Two TCR γ polypeptides (46K and 43K) of identical NEPHGE mobility were synthesized by the IDP2 cell line. Treatment with endo-H reduced both forms to a 40K form, suggesting that the 46K and 43K forms carried different numbers of carbohydrates, and that a single TCR γ polypeptide backbone (40K) was synthesized by IDP2 cells (FIG. 7E, F). In contrast, a more basic, 38K glycosylated form was synthesized by PBL Cl, which after endo-H digestion displayed a nonglycosylated 31K peptide backbone (FIG. 7G, H). Thus the TCR γ polypeptides on the non-disulphide-linked (IDP2) and the disulphide-linked (PBL Cl) forms characterized here have radically different peptide backbone sizes (40K and 31K respectively). The fact that the glycosylated TCR γ peptides observed by pulse-labeling are of different molecular weight than those found by cell surface iodination presumably results from the different types of carbohydrates they carry, namely high-mannose versus complex.

We next wished to determine if both a disulphide-linked and a noncovalently associated form occurred in normal adult peripheral blood. The polyclonal peripheral blood cell line (WT31−PBL LINE) from which PBL C1 had been cloned was therefore studied in greater detail. WT31−PBL LINE was homogeneously T3+T11+ and contained 95% WT31−T4−T8− with 5% contaminating WT31+ cells. When examined by immunoprecipitation from iodinated, solubilized cells, weak but detectable reactivity with mAb βF1 was observed (FIG. 5B, lanes 10 reduced and 13 nonreduced), consistent with the expected 5% TCR α, β positive lymphocytes In contrast, anti-T3 mAb immunoprecipitated large amounts of both T3 and associated polypeptides of 35–45K under reducing conditions (FIG. 5B, lane 11). To determine what fraction of these were disulphide-linked, the T3 immunoprecipitate was examined under nonreducing conditions (FIG. 5B, lane 14). Less than half of the T3-associated polypeptides were disulphide-linked. This material included disulphide-linked TCR α, β peptides located above the open arrow, lane 14 (size identified by the βF1 precipitate, lane 13) and disulphide-linked TCR γ peptides of smaller size (open arrow, lane 14). Strikingly, the majority of the T3-associated species were not disulphide-linked and migrated with the same mobility under both reducing and nonreducing conditions. Notably, a fraction of these non-linked species displayed a marked increase in SDS-PAGE mobility under nonreducing conditions, similar to the TCR δ on the IDP2 and PEER cells (see FIG. 5B, lane 14, solid arrow) Reactivity with anti-C γ sera confirmed that most of the labelled material associated with T3 expressed on WT31−PBL LINE was TCR γ gene products (lane 16).

Thus, the protein product of the TCR γ gene occurs on T3+ lymphocytes in adult peripheral blood in both disulphide-linked and unlinked molecular γ forms. Moreover, the non disulphide-linked form of TCR may be further divided into 55–60K glycosylated (IDP2 and PEER) or 35–45K glycosylated (thymic T cell clone C11 (70) and WT31−PBL LINE) species.

Figures 8A, 8B, 8C:
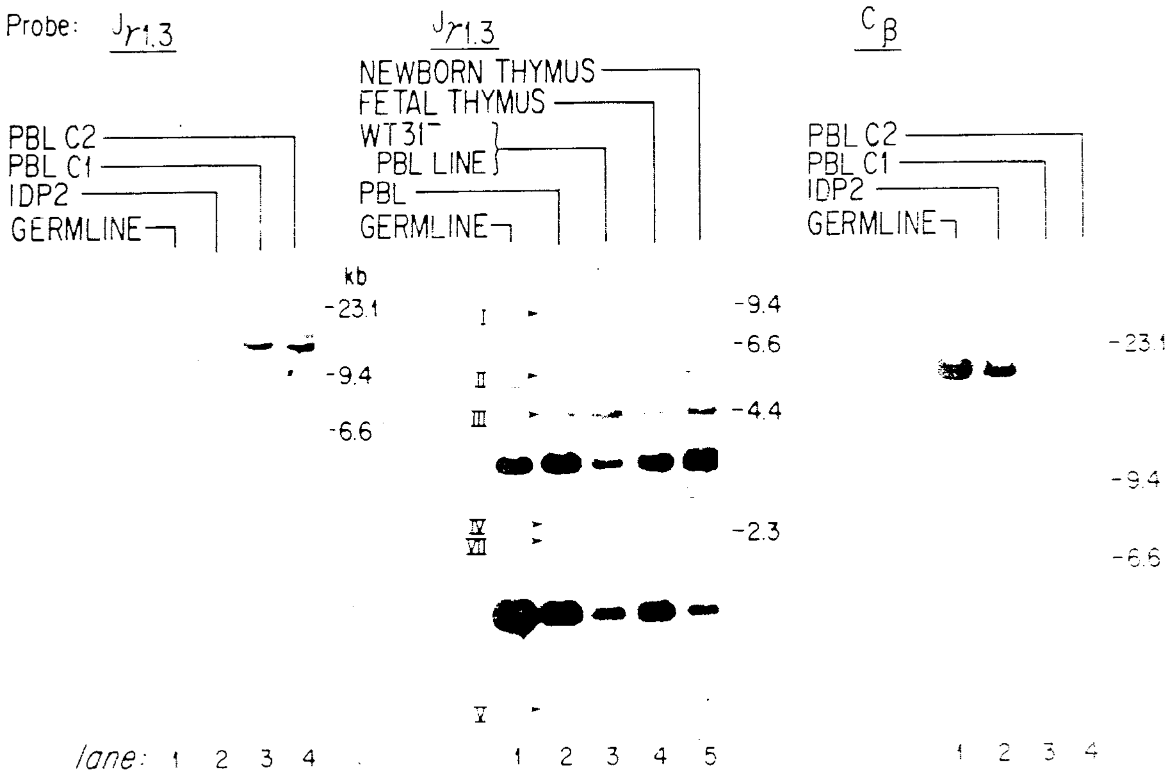

TCR γ and β gene rearrangements were examined in T cells known to express the TCR γ polypeptide on their cell surfaces. Southern blot analysis were carried out using the 0.8 kb EcoRI-HindIII human $J_{\gamma 1,3}$ probe (nomenclature according to Quertermous et al.(71)). This probe detects germline bands of 23kb and 12kb in a BamHI digest of genomic DNA. The 23 kb band encompasses $C_{\gamma 1}$ and the 12 kb band encodes $C_{\gamma 2}$. Using this probe, IDP1, PBL C1 and PBL C2 (also derived from the WT31−PBL LINE) showed rearrangements of the TCR gene (both PBL C1 and PBL C2 displayed an identical rearrangement; FIG. 8A).

Seven rearrangements in PBL using the $J_{\gamma 1.3}$ probe and EcoRI-digested genomic DNA in Southern blot analyses have been detected (20). Six (I, II, III, IV, VII and V) of these seven rearrangements are shown in PBL, fetal thymus, and newborn thymus genomic DNA (FIG. 8B; see arrows and rearrangement numbers). Four rearrangements (I, II, VI and VII) either are not used by peripheral blood lymphocytes which express the TCR γ polypeptide or cells demonstrating them were lost under the propagation conditions used for the WT31−PBL Line. Nevertheless, the WT31−PBL LINE DNA revealed at least three of these rearrangements (III, IV and VI) (FIG. 8B, lane 3) and these same rearrangements were used by IDP2, PBL C1 and PBL C2 (data not shown for the EcoRI digest) and all of these rearrangements are displayed in fetal thymus.

The TCR β gene was also rearranged in IDP2, PBL C1 and PBL C2 cells. The 1.1 kb EcoRI-HindIII $C_{\beta 2}$ probe detects a germline band of 20 kb which encompasses both Cβ constant regions in a BamHI digest of genomic DNA (68). One predominant TCRβ rearrangement for IDP2 and two identical rearrangements for PBL C1 and PBL C2 were observed (FIG. 8C). It is assumed that these TCR β rearrangements are nonproductive based on the immunoprecipitations and Northern analyses for these cell lines. As both PBL C1 and PBL C2 have the same TCR γ and δ rearrangements, they appear to be clonal and derived from the same cell within the WT31−PBL LINE.

Figure 9A:
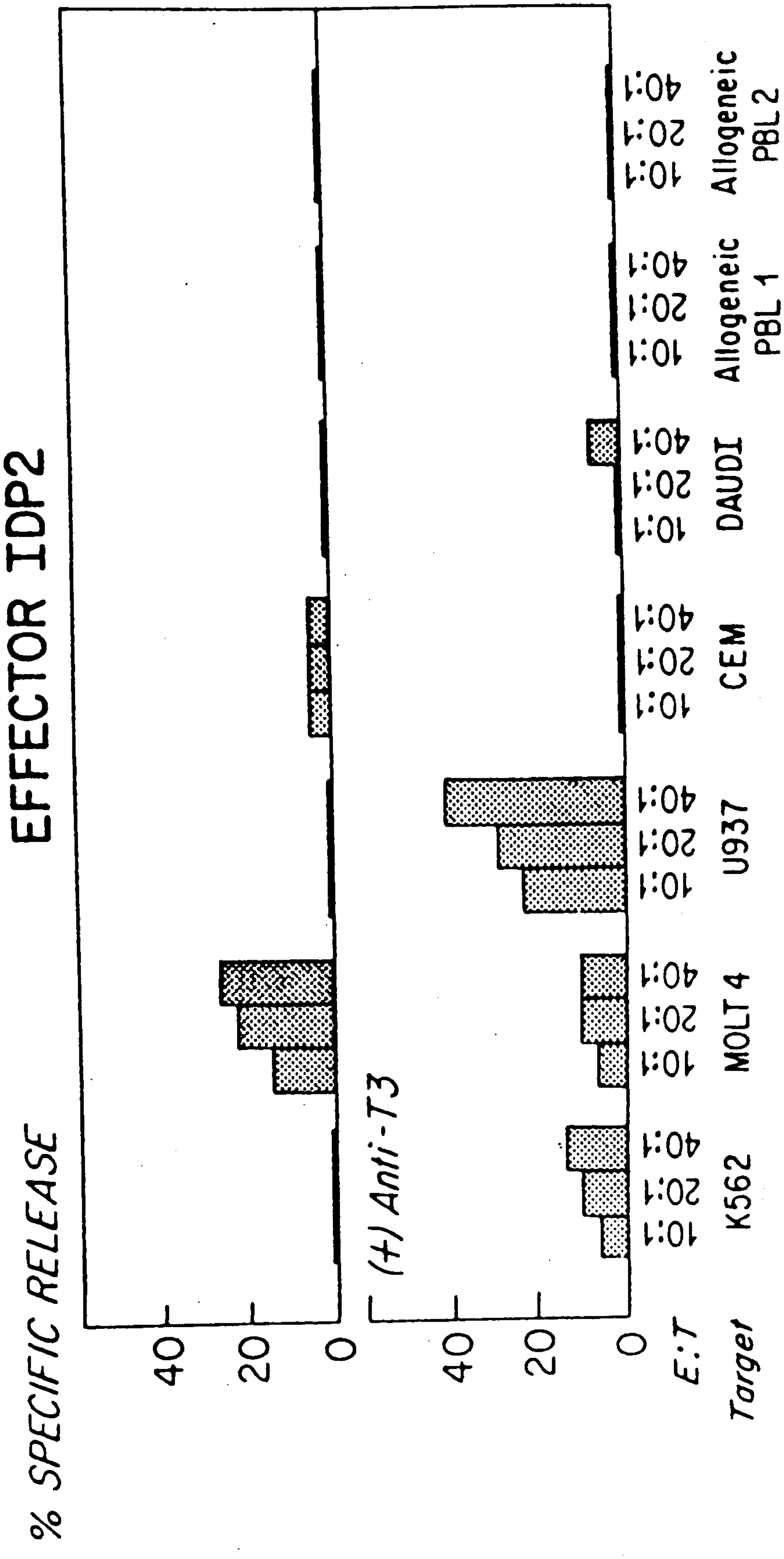
Figure 9B:
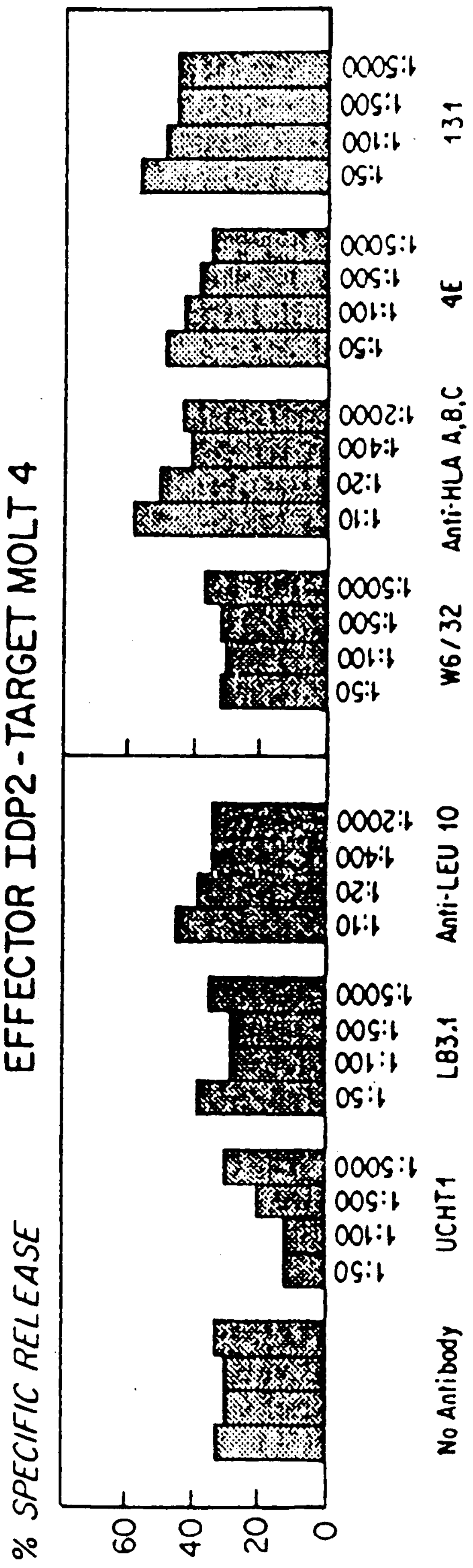

As TCR γ-expressing cells were found in adult peripheral blood, functional studies were carried out to determined whether they have effector capabilities. When IDP2 and PBL C1 were examined for their ability to lyse target cells in $^{51}Cr$ release assays, they proved to have spontaneous effector cytotoxic capability (FIG. 9). Although the IDP2 cell line did not lyse the majority of natural killer (NK) targets or PHA blasts of allogeneic PBL, they were selectively capable of lysing $^{51}Cr$-labelled MOLT-4 cells (FIG. 9A top). In 30 two of six similar assays, weak lysis (10–15% $^{51}Cr$ release) of K562 targets was also observed Lysis of MOLT-4 cells was not inhibited by a variety of mAb directed against monomorphic MHC Class I (W6/32 anti-HLA-A, B, C, 4E and 131) or Class II (LB3.1 and antiLeu 10) determinants (FIG. 9B), although we previously found that these mAb efficiently block killing by both MHC Class I and Class II allospecific CTL (34). These data suggest that lysis of MOLT-4 cells was MHC class I and II independent. Only anti-T3 mAb partially blocked the specific lysis of MOLT-4 cells (FIG. 9B). On the other hand, when triggered by prebinding of anti-T3 mAb to IDP2, as has been previously reported for thymic-derived CII[7], $^{51}Cr$-labelled target cells that express Fc receptors for IgG (for example, U937), were efficiently lysed (FIG. 9A −anti-T3). Such killing could be completely inhibited by aggregated human IgG, confirming that this T3-mediated lysis occurred through a mechanism of enhanced conjugate formation via IgG Fc receptors (data not shown). The paradoxical augmentation of lysis by anti-T3 mAb for some targets (U937) and the blocking of lysis for specifically recognized targets (MOLT-4) might result from the competing effects of triggering and increasing conjugate formation via T3 but sterically blocking antigen recognition via the TCR.

Figure 9C:
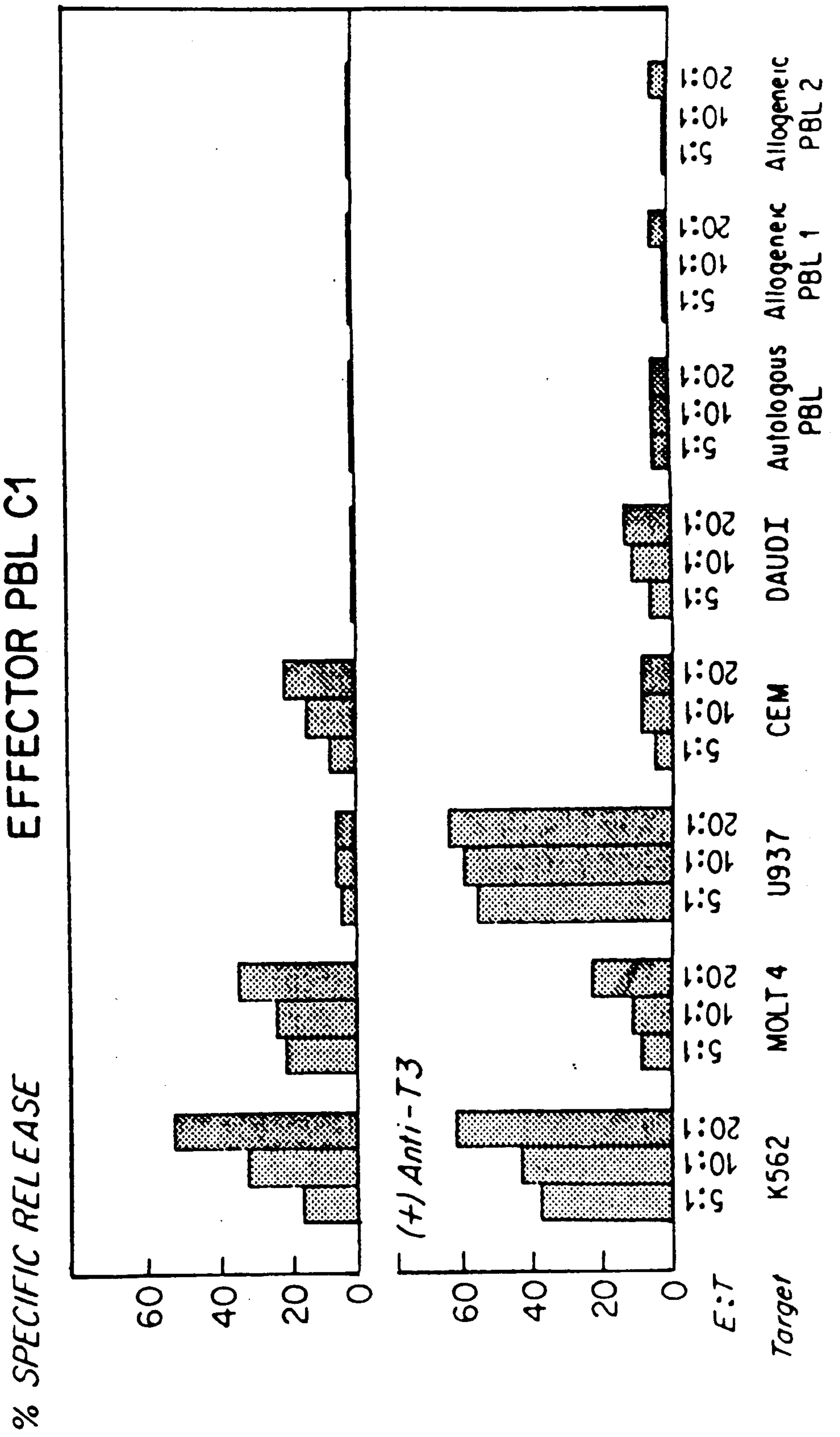

PBL C1 proved a more efficient killer cell than IDP2. PBL C1 displayed spontaneous cytolytic activity against K562 cells (MHC Class I and II negative) showing nearly 50% specific $^{51}Cr$ release when examined at an effector target (E:T) ratio of 20:1 (FIG. 9C top). Moreover, PBL C1 also lysed MOLT-4 cells and to a lesser extent, CEM cells. No lysis of Daudi, U937, or either autologous or allogeneic PBL was detected. Triggering with anti-T3 mAb induced PBL C1 to lyse the U937 cell line. Further, lysis of K562 was slightly augmented while that of MOLT-4 was partially inhibited (FIG. 9C). Taken together, the spontaneous cytolytic activity of IDP2 and PBL C1 on tumor targets such as K562 and MOLT-4 and the failure to block such activity by a MHC mAb indicates that these TCR $\gamma$ lymphocytes are non-MHC class I and class II restricted cytotoxic T lymphocytes.

DISCUSSION

Framework monclonal antibodies against the TCR $\alpha$, $\beta$ molecules, $\beta$F1 and WT31, were used to identify and isolate the WT31−$\beta$F1−T3+ lymphocyte population from the peripheral blood lymphocytes of two immunodeficiency patients. By the criteria of both immunoprecipitation analysis with framework monoclonal antibodies and Northern blot analysis using TCR $\alpha$ and TCR $\beta$ specific cDNA probes, polyclonal human T cell lines of this phenotype were shown to express neither TCR $\alpha$, $\beta$ mRNA transcripts nor polypeptides. Nevertheless, chemical cross-linking studies using the cleavable DSP reagent revealed the existence of a protein complex associated with the T3 glycoprotein on the surface of these cells. The heavier of the two subunits that cross-linked to T3 ($M_r$ 55,000) was also immunoprecipitated by two different antisera, one generated against a 17 amino acid synthetic peptide corresponding to a part of the variable region and another generated against a 20 amino acid synthetic peptide corresponding to a part of the constant region of the deduced amino acid sequence of a rearranged TCR $\gamma$ gene (19, 36) Thus , the $M_r$ 55,000 protein is the TCR $\gamma$ protein encoded by the rearranging TCR $\gamma$ gene (15). The $M_r$ 40,000 polypeptide is a fourth T3-associated protein designated TCR $\delta$ (FIG. 2A and 2B). The TCR $\gamma$ and TCR $\delta$ polypeptides form a T3-associated heterodimeric structure on these cells (T$\gamma$, $\delta$-T3) that is analogous to the previously described T cell receptor complex (TCR $\alpha$, $\beta$).

The TCR $\gamma$ lymphocytes examined here exhibit non MHC restricted cytolytic activity and may be similar to other T3$^+$ NK-like cells whose T-cell receptors have not yet been definitively characterized (39, 72, 73, 74) As NK-like lymphocytes, they may participate in host immune surveillance against malignancy. The specificity of lysis observed suggests that the possibility of TCR $\gamma$ mediated antigen-specific recognition of some but not all tumor targets. As anti-T3 mAb could trigger nonspecific lysis of some target cells or alternatively block specific lysis of other targets, the T3 molecule on these cells appears to be functional.

Example 2

Northern blot analysis of group O hybridizinq transcripts

5 $\mu$g total RNA samples were electrophoresed through 1.5% agarose gels containing 2.2 M formaldehyde and transferred to nitrocellulose. Filters were probed with nick-translated 0-240 or chicken actin (Oncor) (FIG. 12A), or with nick-translated 0-240 (FIG. 12B), a 330 bp Eco RI-Sca I fragment of 0-240/38 (V probe; see FIG. 14) labelled by hexanucleotide priming, or a 550 bp Hae III fragment of 0-240 (3′ UT; see FIG. 14) labeled by nick-translation. Filters were washed with 1xSSC, 0.5% SDS at 23.C followed by 0.1xSSC at 50° C.

Southern blot analysis of group O hybridizinq genomic DNA

Genomic DNA samples were digested with restriction enzymes, electrophoresed through 0.7% agarose, transferred to nitrocellulose, and probed with nick-translated group 0 clones (FIGS. 13A and 13B). Filters were washed with 1xSSC, 0.5% SDS at 23° C. followed by 0.1×SSC, 0.1×SDS at 68° C. (FIG. 13A) or 0.2×SSC, 0.1×SDS at 55° C. (FIG. 13B). In FIG. 13A, note that PBMC and PBL L1 are derived from the same individual. The diminished signal in PBMC presumably results from deletion in most T cells in the sample. The remaining signal (largely B cells and monocytes) serves as a germline control for PBL L1. On this basis the 9.0 kb fragment is interpreted as a polymorphism rather than a rearrangement

Sequence analysis of group O cDNA clones

Nucleotide sequences of clones 0-240, 0-254, 0-240/38 and 0-240/47 were determined using the dideoxy chain termination method via the strategy outlined in FIG. 14.

Experimental Results

A T cell-specific cDNA probe was generated by synthesizing high specific activity $^{32}$P-labeled first strand cDNA from IDP2 poly-A$^+$ RNA, and subjecting this material to two cycles of hybridization with human B cell line JY poly-A$^+$ RNA followed by hydroxylapatite chromatography (76). The twice-subtracted single stranded material was used to probe 4o,000 plaques of an IDP2 λgt10 cDNA library (77), and 391 (1%) hybridizing plaques were obtained. Subsequent analysis organized these clones into 14 cross-hybridizing groups, composed of as many as 139, and as few as 2 members. Three groups were identified as TCR $\lambda$ (10 members), TCR $\beta$ (20 members), and CD3 $\delta/\epsilon$ (7 members), based upon hybridization with appropriate probes. Representative members of the remaining 11 groups (A, B,C,D,E,G,I,K,M,O,R) were $^{32}$P-labelled and used to probe Northern blots. One group (0, consisting of 6 members) detected transcripts expressed in IDP2 and TCR $\gamma\delta$ cell line PEER (69,75,78), but not expressed in JY and the TCR $\alpha\beta$ cell line HPB-ALL. Based on this result, two group 0 clones (0-240 and 0-254) were selected for further study.

Northern blot analysis of a larger panel of RNA samples using 0-240 as a probe (FIG. 12A) revealed the expression of cross-hybridizing transcripts in four TCR $\gamma\delta$ cell lines (IDP2, PEER, Molt-13 (F. Hochstenbach and M. B. Brenner, unpublished data), and PBL L1 (75). Four distinct transcripts, of 2.2 kb, 1.7 kb, 1.3 kb, and 0.8 kb (arrows, FIG. 12A) were detected. However, transcripts were undetectable in B cell line JY, myeloid cell line HL60, TCR $\alpha\beta$ T cell line HPB-ALL and surface TCR$^-$ T cell line SKW3. Transcripts were barely detectable in RNA from fresh or phytohemagglutinin-activated peripheral blood mononuclear cells (PHA PBMC), of which only a small fraction express TCR $\gamma\delta$.

Analysis of genomic DNA digested with a variety of enzymes revealed no evidence for rearrangement of 0-240 hybridizing sequences in TCR $\gamma\delta$ T cells. However although a 9.5 kb Xba I fragment (and a 9.0 kb polymorphic fragment; see FIG. 13A) was detected in B cells, myeloid cells and TCR $\gamma\delta$ T cells, this fragment was deleted on both chromosomes in all other T cell examined. This represents somatic deletion rather than polymorphism, since pairs of B and T cell lines derived from the same individual were analyzed (SB and HSB; 8392 and 8402). These results suggest that deletion of sequences detected by 0-240 may accompany rearrangement at either the TCR α or TCR β locus.

Initial sequence analysis of clones 0-240 (1.5 kb) and 0-254 (0.7 kb) revealed that they both extend from an endogenous Eco RI site at the 5′ terminus through a poly-A tail end an Eco RI site in the linker at the 3′ terminus. These clones were derived from a cDNA library constructed without methylation of Eco RI sites. In order to obtain information 5′ to the natural Eco RI site, 0-240 was used to probe an Eco RI methylated IDP2 λgt10 cDNA library. Two clones that spanned the Eco RI site, 0-240/38 (1.3 kb) and Q-240/47 (1.4 kb), were selected for detailed study. In contrast to the results obtained using probes derived from the 3′ end of the group O cDNA sequence, a probe derived from the 5′ end of 0-240/38 detected discrete rearrangements in both Eco RI and Pvu II digests of genomic DNA from five out of five TCR γδ cell lines (FIG. 13B). Of the three germ line fragments in each digest detected by this probe (arrows, FIG. 13B), rearrangements of the 3.3 kb Eco RI and 23.0 kb Pvu II fragment appeared to be shared by the five TCR γδ cell lines, whereas rearrangements of the 6.6 kb Eco RI and 2.0 kb Pvu II fragments distinguished the different cell lines. As opposed to these discrete rearrangements, a heterogeneous smear of rearrangements was detected in Eco RI digests of two samples of fetal thymus DNA.

The comparative organization and sequencing strategies used to characterize clones 0-240, 0-254, 0-240/38 and 0-240/47 are presented in FIG. 14. Partial restriction maps and the locations of probes V, VJC and 3,UT (hatched bars) are presented. Poly-A tails are noted. FIG. 15 shows the composite nucleotide and deduced amino acid sequences of the group 0 cDNA clones 0-240/38 begins within codon 7 of the composite sequences, whereas 0-240 and 0-254 begin with codon 150. Within the coding region, sequences agree at all positions except for codon 161 (GTG in 0-254 and 0-240/38, TTG in 0-240). This discrepancy is presumed to result from a reverse transcriptase error in 0-240. The composite sequence contains a long open reading frame of 293 amino acids clearly composed of V-, J- and C-like elements similar to those of TCR and immunoglobulin genes. Strikingly, the putative C region sequence is 79% identical at the nucleotide level, and 73% homologous at the amino acid level, to the sequence of a novel murine TCR constant region gene (Cx) recently reported by Chien, et al. (79) to reside within the TCR α locus. The high degree of sequence homology indicates that the group 0 clones reported here represent the human homologue of murine Cx. Thus, the deletion of this sequence in TCR αβ T cells suggests that the human constant region, like its murine counterpart, maps 5′ to Cα within the human TCR α locus.

The 5′ ends of 0-240/38 and 0-240/47 define a partial putative leader (L) sequence and a variable (V) region sequence. The precise processing point between these segments defining the amino terminus of the mature protein is unknown. However, processing of the TCR α chain in HPB-MLT has been suggested to occur between A(−1) and Q(+1) since the amino terminus of TCR α is blocked (8). By analogy, we have tentatively assigned the processing point to this location in our sequence, since in the region from −4 to +8 the two sequences are identical in 11/12 residues.

The putative V region displays 57% amino acid sequence identity with a human Vα sequence (PGA5, ref. 8), 26% identity with a human Vβ sequence (YT35, ref. 4), and 21% identity with a human Vγ sequence (V72, ref. 21). Comparisons among Vα subgroup sequences and among Vβ subgroup sequences can be used to identify consensus residues that occur in 50% or more of Vα or Vβ subgroups. In FIG. 16, the deduced 0-composite V region amino acid sequence is compared to Vα and Vβ subgroup consensus sequences. Consensus residues were assigned based upon their appearance in 50% or more of Vα or Vβ subgroups, using the data compiled in reference 89.

The V region sequence reported here matches the Vα consensus in 75% of these residues (30/40). By contrast, it only matches the Vβ consensus in 49% of these residues (17/35). For comparison, the randomly selected Vα sequences 1.1, 6.1, and 12.1 match the Vα consensus in 70%, 73% and 73% of these positions, respectively, whereas the Vβ sequences 2.2, 5.4 and 8.1 match at 40%, 53% and 60%. Thus, this V region is clearly Vα-like, since it is as close to the consensus as other Vα sequences.

In FIG. 17, the deduced 0-composite J region amino acid sequence is compared to Jα, Jβ and Jγ consensus residues. Consensus residues were assigned based upon their appearance in 40% or more of the Jα, Jβ and Jγ sequences compiled in references 71 and 89. Amino acids 112–125 display significant homology to human TCR consensus J region sequences and with the J region associated with murine Cx (FIG. 15). However, amino acids 94–111 are homologous to neither V nor J sequences, and homology with the murine clone is minimal in this region as well (FIG. 15). Whether and how much of this area is encoded by a separate D element or results from so called N-region diversity (80) remains to be determined. Clearly, as the amino acid sequence remains in frame across the V(D)J junction, the IDP2 group 0 cDNA clones correspond to transcripts from a productively rearranged gene.

The putative constant region sequence includes an immunoglobulin-like region with two cysteine residues separated by 51 amino acids, a connector region carrying a cysteine residue which is typically believed to mediate interchain disulfide bonds between TCR components, and an intramembraneous region. Two potential sites of N-linked glycosylation are situated immediately amino-terminal to the first cysteine and carboxy-terminal to the second cysteine In FIG. 18, the deduced 0-composite C region amino acid sequence is compared with Cα(90), Cβ1(91), Cγ1 (88) and Cλ (92). In FIG. 19, the distribution of charged and uncharged amino acids in the region flanking and including the presumed transmembrane region of the O-composite sequence is compared with those of Cα, Cβ and Cγ. Within the first 91 amino acids of the constant region amino acid sequence identity is highest with Cγ and Cλ (22% and 20%, respectively) and lower with Cα and Cβ (15% and 11%, respectively). The connector region shares elements with each of the other TCR chains. However, the 40 amino acids including and flanking the presumed transmembrane region show a significantly higher number of identities with the homologous region of Cα (30%) than with either Cβ (8%) or Cγ (13%). These relationships are underscored by comparison of the number and distribution of charged and uncharged residues throughout this region. Similar to that of Cα the O-group constant region appears to have at least two positively charged residues which may be buried within the membrane. Such charged residues are thought to be important in mediating interactions with CD3 components, which display acidic residues within their transmembrane regions (81–83). Also, as in the case of Cα, an intracellular tail (if it exists at all) would be extremely short. Whereas Cβ and Cγ display putative intracellular tails which are highly charged, the IDP2 group O sequence contains a single basic residue followed by four hydrophobic amino acids. The corresponding Cα sequence is of equal length. Regardless of how the membrane proximal sequences are disposed relative to the lipid bilayer and to CD3 components, it appears likely that this portion of the constant region is involved in interactions highly analogous to those of Cα. The 3′ untranslated (3′ UT) sequences indicate the use of alternative polyadenylation sites. Whereas the O-240 3′ UT extends some 950 bp to an ATTAAA polyadenylation signal, that of 0–254 extends only 260 bp, with polyadenylation following the sequence TATAAA. Both sequences differ from the consensus AATAAA by a single nucleotide. Potential for additional heterogeneity exists, since the sequence TATAAA occurs twice more within the 0–240 sequence (13 bp 3′ to the signal used in 0–254 and 130 bp 5′ to the signal used in O-240). Variation in the site of polyadenylation is at least partially responsible for the transcript heterogeneity observed in Northern blots (FIG. 12B). Whereas the 2.2 and 1.3 kb transcripts are selectively detected by a V region probe, an O-240-specific 3′ UT probe detects only the 2.2 and 1.7 kb transcripts. Thus in IDP2, PEER and PBL L1 the two most abundant species (2.2 and 1.3 kb) represent differentially polyadenylated transcripts. The minor 1.7 and 0.8 kb species therefore represent transcripts lacking V regions and are presumably transcribed from partially rearranged genes. By contrast, TCR β mRNA heterogeneity primarily results from the latter mechanism (84).

The group O cDNA clones appear to be good candidates to encode the IDP2 TCR δ peptide. They detect transcripts that are expressed specifically in TCR γδ T cells and are encoded by genes specifically rearranged in the same cells. Transcript levels correlate well with the level of expression of cell surface TCR δ polypeptide, which is lower in PEER than in IDP2, and lower still in Molt-13 (unpublished data). Furthermore, the sequence of the group O clones is composed of V, J and C elements which are homologous to those of other TCR and Ig genes. The cDNA clones derived from IDP2 mRNA remain in frame across the V-J junction, indicating that they would encode a functional polypeptide in these cells. The predicted molecular weight of the polypeptide is 31.3 kd, with two potential N-linked glycosylation sites. As demonstrated below, these predictions agree well with the properties of the TCR δ peptide of IDP2 cells. Furthermore, it is demonstrated below by in vitro transcription and translation analysis that clone O-240/38 encodes a polypeptide immunologically crossreactive with the IDP2 TCR δ protein.

Human TCR γ and δ peptides can exist in a disulfide-linked form or an unlinked form in different cell lines (75, 85–89). This structural heterogeneity is known to be controlled at least in part by TCR γ constant region usage, since the Cγ-gene encodes a cysteine in the membrane proximal connector region which is absent in Cγ-2 (77,78,88). IDP2 uses the Cγ-2 gene, lacks this cysteine, and displays a nondisulfide linked receptor on the cell surface (75,77). One might have predicted that the IDP2 TCR δ peptide would lack the analogous cysteine as well. However our cDNA sequences predict that IDP2 TCR δ carries a cysteine in the membrane proximal connector that would be available for disulfide linkage. Moreover, Southern blots (FIG. 13A and data not shown) provide evidence for only a single TCR δ constant region gene. Thus, it appears that a single TCR δ gene product could interact with TCR γ peptides encoded by Cγ-1 to form a disulfide-linked complex, or with TCR γ peptides encoded by Cγ-2 to form a non-linked complex.

In contrast to TCR α and TCR β, only a limited number of functional TCR γ V regions exist (21). Thus the TCR δ V gene pool size will be important in determining the number of antigens that may be recognized by TCR γδ lymphocytes. The V region used by IDP2 is clearly related to TCR α V regions, but whether TCR α and TCR δ draw from the same or distinct pools of V regions is not known. Recent nucleotide sequence analysis indicates that the IDP2, PBL C1 and Molt-13 TCR δ chains all use the same V region (data not shown), an observation consistent with genomic rearrangement data (FIG. 13B). This result might suggest a limited TCR δ V repertoire. The size and nature of the TCR δ V gene pool will have intriguing implications for the relationship between the TCR αβ and TCR γδ repertoires, and will be an important area for further study.

(FIG. 23). The IDP2 0–240/38 cDNA clone 1.5 kb insert begins within codon γ of the composite Group O sequence and includes the remaining coding region and most of the 3′ untranslated region. This insert was cleaved as a single EcoRI fragment from λgt10 arms by partial EcoRI digestion (to prevent cleavage of the internal EcoRI site). This fragment was subcloned into a Bluescript+ vector (Stratagene). The insert was then removed from the vector as a single BamHI-Sal I fragment (ends are from the Bluescript vector polylinker) facilitating directional cloning into pGEM-3 (Promega Biotech) downstream of the Tγ promoter. The resultant pGEM3O-240/38 plasmid was linearized with Sal I and capped transcripts synthesized using Tγ RNA polymerize (77,99,100). Integrity and size of the transcripts were monitored via an aliquot of the reaction mixture containing $^{32}P$-ATP. A single RNA species of 1.5 kb was observed. In vitro translation in the presence of $^{35}S$-methionine was performed in a rabbit reticulocyte lysate (101). After in vitro translation, the samples were boiled in 1% SDS with 2 mM dithiothrietol followed by the addition of 10 volumes of 2% TX-100 in TRIS buffered saline pH 7.5. Samples were immunoprecipitated with control mAb P3 (FIG. 24, lanes 1 and 3) or with anti-TCR δ1 mAb (lanes 2 and 4) and analyzed by SDS-PAGE followed by fluorography (66).

Experimental Results

We have generated a monoclonal antibody (mAb) that is specifically reactive with the TCR δ subunit and used it to characterize the TCR δ polypeptide. We present immunochemical evidence that a novel cDNA clone encodes the T cell receptor δ subunit.

Example 3

Culture method

The Peer cell line described hereinabove was cultured in vitro in a medium composed of RPMI 1640, 10% fetal calf serum, penicillin-streptomycin, and L-glutamine. The culture was fed twice a week and was kept at 37° C. in a humidified incubator with 5% $CO_2$.

Hybridoma production for monoclonal antibodies specific for the TCR γ chain

A BALB/c mouse was immunized intraperitoneally (I.P.) with $2\times10^7$ Peer cells suspended in 0.2 ml of phosphate buffered saline (PBS). The mouse was boosted by I.P. injection every 10 days with $2\times10^7$ Peer cells for a total of 20 injections. Three days before fusion, the mouse was boosted by intravenous (I.V.) injection with $2\times10^7$ Peer cells for 3 sequential daily I.V. injections. The mouse was sacrificed and the spleen was removed at the last I.V. injection. Immune spleen cells were fused with mouse myeloma cell P3 x 63Ag8.653 in the presence of polyethylene glycol 1500 at the ratio of 5:1 by standard procedures. After fusion, cells were suspended in the culture medium containing hypoxanthine ($1\times10^{-4}$,), aminopterin ($8\times10^8$M), and thymidine ($1.6\times10^5$M) and plated at $2\times10^5$ cells per well in microliter plates which contained $2\times10^5$ BALB/c thymocytes per well as feeder cells. The cultures were fed with the same medium on day 7. Beginning on day 14, cultures were fed with the same medium lacking aminopterin.

Hybridoma screening for monoclonal antibodies specific for the TCR γ chain

Since both the γ and δ chains of the T cell antigen receptor protein on Peer cells are complexed with CD3 antigen, antibodies against the Peer T cell antigen receptor should be able to co-modulate these surface proteins with an anti-CD3 monoclonal antibody such as OKT ®3 (2). Such co-modulation was employed as the primary screen of desirable hybridomas as follows. Each of the hybridoma culture supernatants was harvested and screened for its ability to co-modulate surface CD3 protein complexes with an anti-CD3 monoclonal antibody. One hundred microliters of a culture supernatant were added to each well of a 96-well microliter plate containing $5\times10^5$ Peer cells per well. After overnight incubation at 37° C., fluorescein isothyiocyanate-conjugated OKT ®3 was added to each well and cultured for an additional 30 minutes at 0° C. Samples were then analyzed by flow cytometry. Supernatants which induced a significant decrease in fluorescence intensity were selected and further characterized by the immunoprecipitation methods described below. The cells in selected wells which secreted anti-human T cell antigen receptor proteins were subsequently cloned by the limiting dilution method.

Immunoprecipitation

Peer cells were radiolabeled with $^{125}$I and solubilized in Tris buffered saline (TBS) containing 1% Nonidet P-40 as described hereinabove. Immunoprecipitation was performed by incubating $^{125}$I-labeled Peer cell lysates with each of the selected supernatants under reducing conditions. After immunoprecipitation, the samples were analyzed by 10% sodium dodecyl sulfate-polyacrylamide gel electrophoresis (SDS-PAGE). The gels were dried and autoradiographed, and the molecular weight of proteins was determined by comparison with molecular weight standards (75).

Production and screening of hybridomas which produce a monoclonal antibody specific for the TCR δ chain Monoclonal antibodies were made by immunizing BALB/c mice with immunoprecipitated TCR γ, δ-CD3 from the Peer cell line. Briefly, gram of Peer cells was solubilized in 0.3% CHApS detergent and immunoprecipitated with 5 microliters of UCHT1 ascites and fixed *Staphylococcus aureas* Cowan I strain bacteria as the immunoadsorbant similar to the procedure described in (46). The washed immune complexes were injected intraperitoneally at 4 week intervals for a total of 5 immunizations (46). The mice were then sacrificed and the spleen cells fused to P3X63Ag8.653 myeloma cells. The hybridomas were grown in HAT selection, screened and characterized by immunoprecipitation on $^{125}$I-labeled Peer cells and other cells as described in (75).

Results

As shown in FIG. 10, Lane 4, the antibody in hybridoma 34D12 supernate immunoprecipitated a 55 Kd protein and a 20 Kd protein under reducing conditions from the iodinated lysate of Peer cells. This 55 kd protein corresponds to the γ chain of the T cell antigen receptor and the 20 kd protein of the T3 protein on Peer cells.

In a separate experiment a monoclonal against the T cell antigen receptor δ chain, i.e., 4A1, was produced and characterized As shown in FIG. 11, lane 5, 4A1 specifically reimmunoprecipitated a T cell antigen receptor δ chain (40 kd) from IDP2 cells (75). 4A1 has also been shown to immunoprecipitate the T cell antigen receptor γ, δ complex from several other T cell antigen receptor γ, δ positive cell lines, including IDP2, Molt-13 and PBL line 2.

Example 4

Cytofluorographic analysis of T cell lines with anti-TCR δ1

TCR γδ cell lines PEER and IDP2 or TCR αβ cell lines HPB-MLT and JURKAT were stained with 50 μl of anti-TCR δ1 culture supernatant followed by staining with FITC-conjugated goat anti-mouse Ig F(ab)'$_2$ fragments with analysis on an Ortho cytofluorograph as previously described (95) (see FIG. 20). Control was the mAb secreted by P3X63.Ag8 hybridoma (P3) and anti-CD3 mAb was anti-Leu 4 (97). The anti-TCR δ mAb was made as follows: One gram of PEER cells were solubilized in 50 ml of 0.3% CHAPS (3-[(3-cholamidopropyl)dimethylammonio]1-propanesulfonate) detergent and were immunoprecipitated with 1 μl of UCHT1 (40) ascites, 500 μl of mAb 187.1 culture supernatant and *Staphylococcus aureus* Cowan I strain (SACI). Four intraperitoneal injections at six week intervals were carried out followed by a final boost of TCR γδ (without CD3) isolated by selective elution of TCR γδ from the immune complexes using 2% TX-100. The eluted material was administered both intravenously and intraperitoneally; four days after this boost, the mice were sacrificed and fusion carried out as previously described (46).

Immunochemical analysis of the specificity of mAb anti-TCR δ1

Surface $^{125}$I-labeled IDP2 cells were solubilized and their proteins immunoprecipitated using control mAb P3, anti-Leu 4, anti-TCR δ1, or anti-Cγ serum. Precipitated samples and were analyzed by SDS-PAGE followed by autoradiography. In CHAPS detergent, TCR γδ and CD3 remain associated and are immunoprecipitated as a complex by anti-Leu 4 (FIG. 21, lanes 3 and 4). However, after solubilization in 2% TX-100 detergent, anti-TCR δ1 immunoprecipitates TCR γδ as a dimeric complex without CD3 (lane 6) and anti-Leu 4 immunoprecipitates CD3 as a trimeric complex without TCR γδ (lane 5). After separation of the TCR γδ-CD3 component chains, anti-TCR δ1 immunoprecipitates TCR δ alone (lane γ and 8), while anti-Cγ serum immunoprecipitates TCR γ alone (lane 9). For chain separation experiments (lane 7-9), anti-Leu 4 immunoprecipitates from CHAPS solubilized IDP2 cells were boiled in 1% SDS and were then diluted with 4 volumes of 2% TX-100 followed by immunoprecipitation with anti-TCR δ1 or anti-Cγ serum. This follows procedures used previously (96).

N-linked qlycosylation of the TCR δ polypeptide $^{125}$I-labeled IDP2 cells were solubilized in 0.3% CHAPS, immunoprecipitated with anti-Leu 4 and resolved by SDS-PAGE (FIG. 22). Control lane is mock-digested IDP2 TCR δ. N-glycanase digestion of TCR δ was performed as follows: TCR δ was eluted from a gel slice followed N-glycanase (Genzyme Corp.) digestion (10U/ml) carried out in 30 μ0.17% SDS, 1.25% Nonidet P-40, 0.2M sodium phosphate buffer pH 8.6 for 16 hr at 37 C (98). The digested or mock-incubated TCR δ samples were analyzed by SDS-PAGE and visualized by autoradiography.

Recognition of in vitro translation products cf cDNA clone IDP2 0-240/38 by mAb anti-TCR δ1

A plasmid designated pGEM3-0-240/38 was constructed as follows and used for in vitro transcription-translation The TCR γδ-CD3 complex from the PEER cell line (69,75) was used as immunogen in the production of antibody-secreting hybridoma cell lines. Hybridomas were screened both by cell surface binding (cytofluorographic analysis) and by immunoprecipitation of PEER cell proteins followed by SDS-PAGE analysis Two hybridoma supernatants (5A6 and 4Al) bound to the surface of PEER cells. After subcloning, one mAb (5A6.E9) was characterized further. This mAb bound to the surface of TCR γδ lymphocytes (PEER, IDP2) but failed to react with TCR αβ cells (HPB-MLT, JURKAT) or with non-T leukocytes (FIG. 20 and data not shown). Although the immunogen was composed of a complex of TCR γδ and CD3, the greater affinity of the mAb for TCR γδ cell lines suggested the mAb was not directed against CD3 determinants.

The specificity of the mAb was determined in immunoprecipitation studies using various detergents which affect the association of the proteins comprising the receptor complex. After $^{125}$I-labeled IDP2 cells are solubilized in CHAPS detergent, TCR γ and δ, and CD3 γ, δ and subunits remain part of an associated complex immunoprecipitated by anti-CD3 (FIG. 21, lanes 3, 4). However, if radiolabeled IDP2 cells are solubilized in 2% TX-100 detergent, TCR γδ and CD3 become largely dissociated, and the use of anti-CD3 mAb results in selective precipitation of CD3 (FIG. 21, lane 5). Under these latter conditions, mAb 5A6.E9 immunoprecipitates TCR γδ as a heterodimer without associated CD3 (FIG. 21, lane 6). This observation provides the first direct evidence that TCR γ and TCR δ exist as a non-disulfide-linked heterodimer. To determine whether mAb 5A6.E9 reacts with TCR γ, TCR δ or a combinatorial determinant, immunoprecipitation of separated polypeptide chains was performed. An anti-Leu 4 immunoprecipitate from radiolabeled, CHAPS-solubilized IDP2 cells was boiled in 1% SDS to dissociate the TCR γ, TCR δ, and CD3 proteins. After dilution with four volumes of 2% TX-100, mAb 5A6.E9 specifically immunoprecipitated the 40K (TCR δ) species (FIG. 21, lane 7). When an aliquot of the same immunoprecipitate was analyzed under reducing conditions (FIG. 21, lane 8) a dramatic shift in SDS-PAGE mobility was observed This phenomenon is characteristic of TCR δ from the IDP2 and PEER cell lines (75). In contrast, when the separated chains were immunoprecipitated with anti-Cγ sera, the 55K species (TCR γ), but not the 40K species (TCR δ) was immunoprecipitated (FIG. 21, lane 9). Based on these biochemical and surface binding studies, mAb 5A6.E9 is referred to as anti-TCR δ1.

In addition to PEER and IDP2, anti-TCR δ1 also immunoprecipitates TCR δ from other TCR γδ cell lines including MOLT-13 and PBL LINE 2 (data not shown). It is not known if anti-TCR δ1 reacts with a determinant encoded by a commonly used TCR δ V- or TCR δ C-gene segment. However, the data indicate the presence of the TCR δ polypeptide in cases where visualization of the protein by cell surface labeling is not possible. Such serological cross-reactivity suggests a relatedness among δ proteins from different cell lines, consistent with the results of peptide mapping experiments (95). Further studies utilizing the anti-TCR δ mAb may also resolve the controversy regarding the proposed existence of TCR γγ homodimer (85, 86, 93, 94).

We have isolated cDNA clones from the IDP2 cell line (e.g., IDP2 0-240/38) by the subtractive approach representing a candidate gene which may encode the TCR δ subunit. Genes to which IDP2 group O cDNA clones hybridize in Southern blotting experiments are expressed and rearranged in TCR γδ lymphocytes but are typically not expressed (and are often deleted) in TCR αβ cells. By sequence comparison with other TCR genes, these cDNA clones appear to be composed of novel V, D (?), J, and C gene segments. The IDP2 Group O composite DNA sequence contains a long open reading frame predicting a polypeptide with two potential asparagine-linked glycosylation sites and a molecular weight of 31.3 kilodaltons. To determine the molecular weight of the unglycosylated TCR δ protein and the number of asparagine-linked carbohydrates .that are present on the mature IDP2 TCR δ polypeptide, gel purified TCR δ was either treated with N-glycanase or mock-incubated and analyzed by SDS-PAGE (FIG. 22). Removal of N-linked carbohydrates resulted in a 5K decrease in apparent molecular weight (40K to 35K), suggesting the presence of two (2.5-3K) N-linked glycans on the IDP2 TCR δ. This correlates well with the number of N-linked glycans predicted by the translated amino acid sequence in FIG. 24. The apparent molecular weight of the protein is in general agreement, differing from that predicted by 3.7K.

Given the reactivity of anti-TCR δ1 on IDP2 cells, the specificity for the TCR δ polypeptide, and the recognition of partially denatured (SDS boiled) TCR δ, we tested whether this mAb would recognize directly polypeptide encoded by the candidate TCR δ cDNA clone. Thus, the insert from cDNA clone IDP2 0-240/38 was subcloned into the pGEM-3 expression vector downstream of the Tγ promoter (FIG. 23). Transcripts generated in vitro with Tγ RNA polymerize were then used in a rabbit reticulocyte lysate system to direct the synthesis of protein in the presence of $^{35}S$-methionine. Following in vitro transcription-translation, the reactions were boiled in 1% SDS, diluted with ten volumes of 2% TX-100, and then immunoprecipitated with either an isotype-matched control mAb or with anti-TCR δ1. Anti-TCR δ1 mAb specifically immunoprecipitated a predominant species (34K) (FIG. 24, lane 4). No such band was observed in immunoprecipitates when control mAbs were used (lane 3), when RNA transcripts were omitted (lanes 1 and 2), or when TCR γ constructs were used (data not shown). Thus, the radiolabeled species immunoprecipitated by mAb anti-TCR δ1 corresponds to a polypeptide whose synthesis was specifically directed by the IDP2 0–240/38 cDNA clone. This polypeptide (34K) is very similar in size to the N-glycanase treated IDP2 TCR δ chain (35K). The IDP2 0–240/38 clone lacks a natural ATG initiation codon as well as the leader sequence. There are two potential internal ATG codons (at residues 12 and 44) within the V region of this clone (FIG. 24). Use of these codons to initiate synthesis could result in more than one polypeptide species possibly accounting for the minor species noted (FIG. 24, lane 4).

Taken together, the correlation between predicted and determined extent of glycosylation and peptide size, the selective expression and rearrangement in TCR γδ cells, and the direct serological recognition of the polypeptide encoded by IDP2 0–240/38, argue compellingly that this candidate cDNA represents the gene encoding the IDP2 TCR δ subunit. The constant region of this cDNA clone is 79% homologous at the nucleotide level to the recently described murine Cx gene (79) which may therefore correspond to the murine TCR δ equivalent. Cloning of both TCR γ and TCR δ make it possible to more fully elucidate the expression, rearrangement, and diversity of the receptor. Moreover, mAbs against TCR δ that bind to the surface of γδ-bearing T cells should facilitate functional studies and move us closer to understanding the role these cells play in the immune system.

Example 5

Immunoprecipitation and SDS-PAGE analysis of T cell antigen receptor

Motl-13, PEER, and HPB-ALL cell lines were iodinated using the lactoperoxidase technique. The $^{125}I$-labeled cells were solubilized in Tris-buffered saline (pH 8) containing 1% Triton X-100. Lysates were immunoprecipitated using δ TCAR-3 antibody or βF1 antibody. All samples were analyzed by SDS-PAGE under reducing or non-reducing conditions (FIG. 25). Molt-13 and PEER are both $CD3^+4^-8^-WT31^-$. HPB is $CD3^+4^+8^+WT31^+$.

Note that in FIG. 25 δTCAR-3 immunoprecipitates nondisulfide-linked γ and δ chains from Molt-13 and PEER while βF1 immunoprecipitates disulfide-linked α and β chains from HPB-ALL. The δTCAR-3 antibody was generated as follows: One mouse was immunized with $2\times10^7$ Molt-13 cells by intraperitoneal injection. One month later the mouse was boosted with $1\times10^7$ Molt-13 cells by intravenous injection each day for 3 sequential days, and then immune splenocytes were fused with mouse myeloma P3x63Ag8.653 cells in the presence of 50% polyethylene glycol 1500. The hybridomas were screened by analyzing the CD3 co-modulation with flow cytometry. The analysis of CD3 co-modulation was based on the observation that antibody to T cell antigen receptor, when incubated with the cells, caused the internalization of the CD3 complex (103, 104). βF1 is a framework monoclonal antibody to the β chain and is described elsewhere (46). The difference in autoradiographic intensity between the bands corresponding to the δ and γ chains represents differences in the extent of iodination of these two proteins.

Immunoprecipitation of δ chain by δTCAR-3 Antibody

FIG. 26 shows $^{125}I$-labeled Molt-13 cells solubilized in Tris-buffered saline (pH 8) containing 0.3% CHAPS (3-[(3-cholamidopropyl)dimethylammoni]1-propanesulfonate) or in 1% Triton X-100. In 1% Triton X-100, the γδ receptor dissociates from the CD3 complex, while in 0.3% CHAPS, the γδ receptor remains associated with the CD3 complex. Prior to immunoprecipitation, the $^{125}I$-labeled lysates used in lanes 3, 4, and γ of FIG. 26 were denatured by adding SDS to a final concentration of 1% followed by heating for 5 minutes at 68° C. After cooling, iodoacetamide was added to a final concentration of 20 mM. The mixture was then diluted with 4 volumes of 1.5% Triton X-100 in Tris-buffered saline (pH 8). This denaturing process completely dissociates γ chain, δ chain, and CD3 proteins from one another. All samples were analyzed by SDS-PAGE under non-reducing conditions (N) except for the sample in lane 4 which is under reducing conditions (R). Note the difference in mobility of δ chain under reducing and non-reducing conditions. The Anti-Cγ antiserum was generated by immunizing a rabbit with a 20 amino acid synthetic peptide from the γ constant region (residues 117–136).

Analysis of cell surface staining by flow cytometry $5\times10^5$ cells were incubated with the appropriate antibodies (NMS, δTCAR-3' OKT3, or WT31) at 4° C. for 30 minutes and then washed two times with 0.2% BSA in PBS (pH 7.4). Following incubation with fluorescein-conjugated goat anti-mouse IgG for 30 minutes at 4° C. cells were analyzed on an Ortho cytofluorograph (FIG. 27).

Two color cytofluorographic analysis of $\delta TCAR-3^+$ and OKT $3^+$ peripheral blood lymphocytes The peripheral blood lymphocytes were first incubated with δTCAR-3 at 4° C. for 30 minutes. After washing, cells were incubated with phycoerythrin (PE)-conjugated goat anti-mouse IgG for an additional 30 minutes at 4° C. After washing the cells were incubated with fluorescein (FITC)-conjugated OKT3 for 30 minutes at 4° C. and then cells were analyzed on an Ortho cytofluorograph (FIG. 28).

Measurement of intracytoplasmic $Ca^{2+}$ concentration ($[Ca^{2+}]_i$) versus time Molt-13 cells were labeled with the acetoxymethyl ester form of the $Ca^{2+}$-sensitive probe fura-2 (2 'M from a 1 mM stock in DMSO, Molecular Probes, Eugene, Oregon) at a concentration of $10^7$ cells/ml in RPMI 1640 plus 10% fetal bovine serum for 30 minutes at 37° C. Cells were then washed and resuspended at $10^7$ cells/ml in Hanks balanced salt solution (HBSS) plus 5% fetal bovine serum and kept in the dark at room temperature until use. Immediately prior to fluorescent measurement, $2\times10^6$ cells were centrifuged and then resuspended in 2 mls. of fresh HBSS and placed in a quartz cuvette at 37° C. and constantly stirred. Fluorescence was measured on the cell suspension in a SPF-500C fluorometer (SLM Aminco, Urbana, Illinois), the excitation wavelength alternating between 340 (±2) and 380 (±2) nm and emission was detected at 510 (±5) nm. The ratio of 340/380 was automatically calculated (1 ratio every 2 seconds), plotted, and stored in an IBM PC AT. Quantification of $[Ca^{2+}]_i$ from the fluorescence ratio was performed as described by Grynkiewicz, et al. (105). Addition of irrelevant antibodies did not alter $[Ca^{2+}]_i$ while cell lysis resulted in a $[Ca^{2+}]_i$ of 1 uM (data not shown).

Results

We have generated a monoclonal antibody, εTCAR-3, that is directed against the TCR δ chain and which can be used to characterize the δ polypeptide. This monoclonal antibody binds to T cells bearing the γδ receptor and also elicits a fura-2 $Ca^{2+}$ signal upon binding to Molt-13 cells. Using this antibody we can now analyze possible functions of γδ receptors.

The δTCAR-3 monoclonal antibody was generated by immunizing a mouse with the Molt-13 cell line which has a $CD3^+4^-8^-WT31^-$ phenotype. The hybridomas were first screened by CD3 co-modulation as described in Materials and Methods. The positive clones were further screened by immunoprecipitation. δTCAR-3 immunoprecipitation of γδ heterodimer from $^{125}I$-labeled Molt-13 and PEER lysates is shown in FIG. 25. δTCAR-3 does not immunoprecipitate any polypeptide from HPB-ALL (FIG. 25). In contrast, βF1 a framework monoclonal antibody specific to the β chain (46), immunoprecipitates the αβ heterodimer from the HPB-ALL cell line (FIG. 25, lanes 10 and 12). The immunoprecipitated γδ receptor from both Molt-13 and PEER cells, when analyzed under either reducing or non-reducing conditions, displays a heterodimeric structure indicating a non-disulfide-linked γδ receptor in these two cell lines. There is a slight shift in mobility of the δ chain under reducing conditions relative to that observed under non-reducing conditions (FIG. 25, lanes and 3, 5 and 7), a phenomenon which has been noted previously in IDP2 and PEER cell lines (75) suggesting the existence of intrachain disulfide linkages. In order to demonstrate that the δTCAR-3 antibody recognizes a CD3-associated γδ receptor, immunoprecipitations were performed using $^{125}I$-labeled Molt-13 cell lysates solubilized in 0.3% CHAPS detergent (FIG. 26, lane 1). Under these conditions, the CD3 complex remains associated with the receptor, and both γδ heterodimer and the CD3 complex are immunoprecipitated by δTCAR-3. However, when $^{125}I$-labeled lysates were solubilized in 1% Triton X-100 detergent which largely dissociates the CD3 complex from the γδ receptor, only γδ heterodimer is immunoprecipitated by δTCAR-3 (FIG. 26, lane 2). As a control, the anti-CD3 antibody, UCHT-1 (40) immunoprecipitates only the CD3 complex, but not the γδ heterodimer FIG. 26, lane 5).

The specificity of δTCAR-3 was fur&her analyzed by using immunoprecipitations of denatured, $^{125}I$-labeled Molt-13 lysates in which γ, δ and CD3 proteins were completely dissociated. δTCAR-3 specifically immunoprecipitates the δ chain which has an apparent molecular weight of 38kd under non-reducing conditions (FIG. 26, lane 3) and 40 kd under reducing conditions (lane 4). The anti-Cγ antiserum immunoprecipitates the γ chain 1with molecular weight 42 kd under reducing conditions (FIG. 26, lane 7). These data indicate that δTCAR-3 is δ chain specific.

δTCAR-3 not only immunoprecipitates γ, δ heterodimer from the PEER and Molt-13 cell lines, it also binds to the surface of these cell lines and to the IDP2 clone (75). It does not bind to the αβ-bearing HPB-ALL and JURKAT cell lines (FIG. 27). In contrast, WT31 (29), a framework monoclonal antibody to the αβ receptor, reacts with αβ positive HPB-ALL and JURKAT cell lines, but not with γδ positive Molt-13, PEER, and IDP2 cells (FIG. 27). When normal peripheral blood lymphocytes (PBL) were examined, a subpopulation (0.9–2.4%) of $CD3^+$ lymphocytes were positive with δTCAR-3 (FIG. 28). When δTCAR-3, immobilized on tissue culture plates was used for culture of normal human PBL, it selectively stimulated the proliferation of the γδ positive subpopulation. After 45 days in culture, the γδ subpopulation represents 96% of the total cell count.

The immunoprecipitation and cell surface staining of multiple γδ positive T cell lines and T cell clones by δTCAR-3, suggest that it may recognize a common determinant (or framework) of the δ chain shared by PEER, Molt-13, IDP2, and two other leukemias, and a subpopulation of $CD3^+$ T lymphocytes. Alternatively, these γδ-bearing T cells could preferentially use a particular Vδ gene segment. The cloning and sequencing of the δ gene and subsequent expression of δ peptides is necessary to conclusively determine whether δTCAR-3 reacts with the constant or the variable regions of the δ chains.

Antibodies to the αβ T cell antigen receptor stimulate a rise in the cytoplasmic free calcium ion concentration $[Ca^{2+}]_i$ (102). Incubation of Molt-13 cells with δTCAR-3 elicits a rapid increase in $[Ca^{2+}]_i$ similar to the response induced by T3 antibodies (FIG. 29). Moreover, δTCAR-3 similarly stimulated a $Ca^{2+}$ flux in PEER cells and in the γδ positive cell line generated from PBL as described above. We have also observed that incubation of Molt-13, PEER, and IDP2 cells with δTCAR-3 causes the co-modulation of the CD3 protein complex.

The physiological role of γδ-bearing T lymphocytes is not yet understood. The identification of a novel monoclonal antibody that apparently cross reacts with many γδ positive cell types should be invaluable in characterizing the physical and functional properties of the γδ receptor and cells that bear it.

Hybridoma δ TCAR-3, producing monoclonal antibody δ TCAR-3, has been deposited with the American Type Culture Collection, Rockville, Md., and has been assigned accession number HB 9578.

Hybridoma 5A6.E9, producing monoclonal antibody anti-TCRδ1, has been deposited with the American Type Culture Collection, Rockville, Md., and has been assigned accession number HB 9772.

REFERENCES

1. Allison, J. P., McIntyre, B. W. & Bloch, D. J. Immunol. 129, 2293–2300 (1982).
2.Meuer, S. C., Fitzgerald, K. A., Hussey, R. E., Hodgdon, J. C., Schlossman, S. F. & Reinherz, E. L. J.Exp. Med. 157, 705–719 (1983).
3. Haskins, K., Kubo, R., White, J., Pigeon, M., Kappler, J. & Marrack, P. J. Exp. Med. 157, 1149–1169 (1983).
4. Yanagi, Y., Yoshikai, Y., Leggett, K., Clark, S. P., Aleksander, I. & Mak, T. W. Nature 308, 145–149 (1984).
5. Hedrick, S. M., Nielson, E. A., Kavaler, J., Cohen, D. I. & Davis, M. M. Nature 308, 153–158 (1984).

6. Chien, Y., Becker, D. M., Lindsten, T., Okamura, M., Cohen, D. I. & Davis, M. M. Nature 312, 31-35 (1984).
7. Saito, H., Kranz, D. M., Takagaki, Y., Hayday, A. C., Eisen, H. N. & Tonegawa, S. Nature 312, 36-40 (1984).
8. Sim, G. K., Yague, J., Nelson, J., Marrack., P., Palmer, E., Augustin, A. & Kappler, J. Nature 312, 771-775 (1984).
9. M. B. Brenner et al., Nature (London) 322, 145 (1986).
10. Oettgen, H. C., Kappler, J., Tax, W. J. M. & Terhorst, C. J. Biol. Chem 259, 12,039-12,048 (1984).
11. Weiss, A. & Stobo, J. D. J. Exp. Med. 160, 1284-1299 (1984).
12. Brenner, M. B., Trowbridge, I. S. & Strominger, J. L. Cell 40, 183-190 (1985).
13. Allison, J. P. & Lanier, L. L. Nature 314, 107-109 (1985).
14. Samelson, L. E. & Schwartz R. H. Immunol. Rev. 81, 131-144 (1984).
15. Saito, H., Dranz, D. M., Takagaki, Y., Hayday, A. C., Eisen, H. N. & Tonegawa, S. Nature 309, 757-762 (1984).
16. Kranz, D. M., Saito, H., Heller, M., Takagaki, Y., Haas, W., Eisen, H. N. & Tonegawa, S. Nature 313, 752-755 (1985).
17. Hayday, A. C., Saito, H., Gillies, D., Kranz, D. M., Tanigawa, G., Eisen, H. N. & Tonegawa, S. Cell 40, 259-269 (1985)
18. Lefranc, M-P & Rabbitts, T. H. Nature 316, 464-466 (1985).
19. Murre, C., Waldmann, R. A., Morton, C. C., Bongiȯvanni, K. F., Waldman, T. A., Shows, T. B. & Seidman, J. G. Nature 316, 549-552 (1985).
20. Quertermous, T., Murre, C., Dialynas, D., Duby, A. D., Strominger, J. L., Waldman, T. A. & Seidman, J. G. Science 231, 252-255 (1986).
21. LeFranc, M-P, Forster, A., Baer, R., Stinson, M. A. & Rabbitts, T. H. Cell 45, 237-246 (1986).
22. Iwamoto, A., Rupp, F., Ohashi, P. S., Walker, C. L., Pircher, H., Joho, R., Hengartner H. & Mak, T. W. J. Exp. Med. 163, 1203-1212 (1986).
23. Zauderer, M., Iwamoto, A. & Mak, T. W. J. Exp. Med. 163, 1314-1318 (1986).
24. Yague, J., White, J., Coleclough, C., Kappler, J , Palmer, E. & Marrack, P. Cell 42, 81-87 (1985).
25. Dembic, Z., Haas, W., Weiss, S., McCubrey, J., Keifer, H., von Boehmer, H. & Steinmetz, M. Nature 320, 232-238 (1986).
26. Hedrick, S. M. et al. Proc. Natl. Acad. Sci. U.S.A. 82, 531-535 (1985).
27. Blanckmeister, C. A., Yamamoto, K., Davis, M. M. & Hammerling, G. J. J. Exp. Med. 162, 851-863 (1985).
28. Brenner, M. B., Trowbridge, I. S., McLean, J. & Strominger, J. L. J. Exp. Med. 160, 541-551 (1984).
29. Tax, W. J. M., Willens, H. W., Reekers, P. P. M., Capel, P. J. A. & Koene, R. A. P. Nature 304, 445-447 (1983).
30. Spits, H., Borst, J., Tax, W., Capel. P. J. A., Terhorst, C. & de Vries, J. E. J. Immunol. 135, 1922-1228 (1985).
31. Griscelli, C. , Durandy, A., Virelizier, J. L. et al. (1980) In: Seligmann, M. & Hitzig, H. (eds) Primary immunodeficiencies, Elsevier, North-Holland pp 499-504.
32. Hadman, M. R., Dopfer, R. Hans-Harmut, P. & Neithammer, D. (1984) In: Griscelli, C., Vossen, J. (eds) Progress in immunodeficiency research and therapy I. Elsevier Science Publishers B. V., Amsterdam pp 43-50.
33. Levin, L. S., Perrin, J. C. S, Ose, L., Dorst J. P., Miller, J. D. & McKusick, V. A. J. Ped. 90, 55-61 (1977).
34. Brenner, M. B., McLean, J., Yarg, S. Y., van der Poel, J. J., Pious, D. & Strominger, J. L. J. Immunol. 135, 384-390 (1985).
35. Yasunobu, Y., Anatoniou, D., Clark, S. P., Yanagi, Y., Sangster, R., Var den Elsen, P., Terhorst, C. & Mak, T. Nature 312, 521-524 (1984).
36. Dialynas, D. P., Murre, C., Quertermous, T., Boss, J. M., Leiden, J. M., Seidman, J. G. & Strominger, J. L. Proc. Natl. Acad. Sci. U.S.A. 83, 2619-2623 (1986).
37. Raulet, D. H., Garman, R. D., Saito, H. & Tonegawa, S. Nature 314, 103-107 (1985).
38. Snodgrass, H. R., Dembic, Z., Steinmetz, M. & von Boehmer, H. Nature 315, 232-233 (1985).
39. De la Hera, A., Toribio, M. L., Marquez, C. & Martinez-A., . C. Proc. Natl. Acad. Sci. U.S.A. 82, 6268-6271 (1985).
40. Beverley, P. C. & Callard, R. E. Eur. J. Immunol. 11, 329-334 (1981).
41. Krangel, M. S. EMBO J. 4, 1205-1210 (1985).
42. Leiden, J. M., Fraser, J. D. & Strominger, J. L. In press, Immunogenetics (1986).
43. Leiden, J. M. & Strominger, J. L. In press, Proc. Natl. Acad. Sci. U.S.A. (1986).
44. Erickson, B. W. & Merrifield, R. B. (1976) In: Neurath, H. & Hill, R. L. (eds) The proteins. Academic Press N.Y. pp 255-527.
45. Liu, F-T, Zinnecker, M. Hamaoka, T. & Katz, D. H. Biochem. 18, 690-697 (1979).
46. Brenner, M. B., et al. J. Immunol. 138, 1502-1509 (1987).
47. Kenneth, R. H., McKern, T. J. and Bechtol, K. B. (eds) Monoclonal Antibodies: a new dimension in biological analysis. Plenum Press, N.Y. (1980).
48. Ischimori, Y., Kurokawa, T., Honda, S., Suzuki, N., Wakimasu, M. and Tsukamoto, K., J. Immun. Method. 80, 55-66 (1985).
49. Royer, H. D., Bensussan, A., Acuto, O. and Reinherz, E. L., J. Exp. Med. 160: 947-953 (1984).
50. Acuto, 0., Fabbi, M., Smart, J., Poole, C. B., Protentis, J., Royer, H. D., Schlossman, S. F. and Reinherz, E. L., Proc. Natl. Acad. Sci. U.S.A., 81, 3851-3855 (1984).
51. Maniatis, T., Fritsch, E. and Sambrook, F., *Molecular Cloning, A Laboratory Manual,* Cold Spring Harbor Laboratory, Cold Spring Harbor, N.Y. 11724 (1982).
52. Schreier, M., Kohler, G., Hengartner, H., Berek, C., Trucco, M. and Formi, L., *Hybridoma Techniques,* Cold Spring Harbor Laboratory, Cold Spring Harbor, N.Y. 11724 (1980).
53. Yelton, D. E., Desaymard, C. and Scharff, M. D., Hybridoma 1, 5-11 (1981).
54. Brenner, M. B., McLean, J. and Strominger, J. L., Feb. Proc. 45, 1292 (1986).
55. Hopp, T. P., and Wood, K. R., Proc. Natl. Acad. Sci. USA 78, 3824-3828 (1981).
56. Kyte, J. and Doolittle, R. F., J. Mol. Biol. 157, 105-132 (1982).

57. Geysen, H. M., Barteling, S. J. and Meloen, R. H., Proc. Natl. Acad. Sci. USA 82, 178–182 (1985)
58. Barnstable, C. J. et al., Cell 14, 9–20 (1978).
59. Bushkin, Y., et al., J. Exp. Med. 164, 458–473 (1986).
60. Yang, S. Y., et al., Immunogenetics 19, 217–231 (1984).
61. Spear, B. T., et al., J. Exp. Med. 162, 1802–1810 (1985).
62. Gorga, J. C., et al., Meth. Enzym. 106, 607–613 (1984).
63. Chen, Y. X., et al., Hum. Immun. 10, 221–235 (1984).
64. Samelson, L. E., et al., PNAS USA 82, 1969–1973 (1985)
65. Krangel, M. S., et al., Cell 18, 979–991 (1979).
66. Bonner, W. J. and Laskey, R. A., Eur. J. Biochem 46, 83–88 (1974).
67. Southern, E. M., J. Molec. Biol. 98, 503–517 (1975).
68. Duby, A. D. and Seidman, J. G. PNAS U.S.A. 83, 4890–4894 (1986).
69. Weiss, A., et al., PNAS USA 83, 6998–7002 (1986).
70. Bank, I., et al., Nature 322, 179–181 (1986).
71. Quertermous, T., et al., J. Immunol. (in press).
72. Nowill, A., et al., J. Exp. Med. 163, 1601–1606 (1986).
73. Lanier, L. L., et al., J. Exp. Med. 164, 339–344 (1986).
74. Moingeon, P., et al., Nature 323, 638–640 (1986).
75. Brenner, M., et al., Nature 325, 689–694 (1987).
76. M. M. Davis et al., Proc. Natl. Acad. Sci U.S.A. 81, 2194 (1984).
77. M. S. Krangel et al., Science 237, 64 (1987).
78. D. R. Littman, et al., Nature (London) 326, 85 (1987).
79. Y. Chien et al., Nature (London) 327, 677 (1987).
80. S. Tonegawa, Nature (London) 302, 575 (1983).
81. P. Van den Elsen et al., Nature (London) 312, 413 (1984).
82. D. P. Gold et al., Nature (London) 321, 431 (1986).
83. G. W. Krissansen, et al., (MBO J. 5, 1799 (1986)
84. Y. Yoshikai et al., Nature (London) 312, 521 (1984).
85. J. Borst et al., Nature (London) 325, 683 (1987).
86. P. Moingeon, et al., Nature (London) 325, 723 (1987).
87. L. L. Lanier et al., J. Exp. Med. 165, 1076 (1987).
88. M. P. Lefranc, A. Forster, T. H. Rabbitts, Proc. Natl. Acad. Sci. USA 83, 9596 (1986).
89 B. Toyonaga and T. W. Mak, Ann. Rev. Immunol. 5, 585 (1987).
90. Y. Yoshikai, et al. Nature (London) 316, 837 (1985).
91. B. Toyonaga, et al., Proc. Natl. Acad. Sci. U.S.A. 82, 8624 (1985).
92. B. Langer, M. Steinmetz-Kayne, N. Hilschmann, Z. Physiol. Chem. 349, 945 (1968).
93. B. Alarcon, et al. Proc. Natl. Acad. Sci. U.S.A. 84, 3861 (1987).
94. C. G. Ionnides, et al., Proc. Natl. Acad. Sci. U.S.A. 84, 4244 (1987).
95. F. Hochsteinbach, M. B. Brenner, In preparation. 96 M. B. Brenner, et al. Nature (London) 322, 145 (1986).
97. J. A. Ledbetter et al., J. Exp. Med. 153, 310 (1981).
98. A. L. Tarentino, C. M. Gomez, T. H. Plummer, Biochemistry 24, 4665 (1985).
102. A. Weiss, et al., Ann. Rev. Immunol. 4, 593 (1986).
103. L. L. Lanier, J. J. Ruitenberg, J. P. Allison, A. Weiss, J. Immunol. 137,2286 (1986).
104. S. C. Meuer, et al., J. Exp. Med. 157, 705 (1983).
105. G. Grynkiewicz et al., J. Biol. Chem. 260, 3440 (1985).

What is claimed is:

1. A substantially pure nucleotide sequence comprising the nucleotide sequence substantially as shown in FIG. 15 designated "Group O Composite," encoding a delta chain of a T cell antigen receptor polypeptide.

2. The nucleotide sequence of claim 1 in which the nucleotide sequence encoding the delta chain of the T cell antigen receptor is expressed in a host cell which glycosylates the delta chain of the T cell antigen receptor, and which glycosylated delta chain of the T cell antigen receptor has a molecular weight of about 40,000 as determined by denaturing polyacrylamide gel electrophoresis.

3. The nucleotide sequence of claim 1 in which the delta chain of the T cell antigen receptor encoded by the nucleotide sequence comprises an unglycosylated protein core having a molecular weight of about 31,000.

4. The nucleotide sequence of claim 1 which is a DNA sequence.

5. A method of producing a delta chain of the T cell antigen receptor polypeptide which comprises expressing the DNA sequence of claim 4 in a suitable host, the DNA sequence being part of an expression construct adapted for expression of the DNA sequence in the host.

6. The nucleotide sequence of claim 1 in which the T cell antigen receptor polypeptide is a human T cell antigen receptor polypeptide.

7. A substantially pure nucleotide sequence encoding the amino acid sequence substantially as shown in FIG. 15 of a delta chain of a T cell antigen receptor.

8. The nucleotide sequence of claim 7 in which the nucleotide sequence encoding the delta chain of the T cell antigen receptor is expressed in a host cell which glycosylates the delta chain of the T cell antigen receptor, and which glycosylated delta chain of the T cell antigen receptor has a molecular weight of about 40,000 as determined by denaturing polyacrylamide gel electrophoresis.

9. The nucleotide sequence of claim 7 in which the delta chain of the T cell antigen receptor encoded by the nucleotide sequence comprises an unglycosylated protein core having a molecular weight of about 31,000.

10. The nucleotide sequence of claim 7 which is a DNA sequence.

11. A method of producing a delta chain of the T cell antigen receptor polypeptide which comprises expressing the DNA sequence of claim 10 in a suitable host, the DNA sequence being part of an expression construct adapted for expression of the DNA sequence in the host.

12. The nucleotide sequence of claim 7 in which the T cell antigen receptor polypeptide is a human T cell antigen receptor polypeptide.

13. A substantially pure nucleotide sequence comprising a portion of a second nucleotide sequence, which second nucleotide sequence is substantially as shown in FIG. 15, which portion encodes a variable region of a delta chain of a T cell antigen receptor polypeptide.

14. The substantially pure nucleotide sequence of claim 13 in which, when the second nucleotide sequence is expressed in a host cell which glycosylates the delta chain of the T cell antigen receptor, the glycosylated delta chain of the T cell antigen receptor encoded by the second nucleotide sequence has a molecular weight of about 40,000 as determined by denaturing polyacrylamide gel electrophoresis.

15. The substantially pure nucleotide sequence of claim 13 in which the second nucleotide sequence encodes a delta chain of the T cell antigen receptor comprising an unglycosylated protein core having a molecular weight of about 31,000.

16. The substantially pure nucleotide sequence of claim 13 which is a DNA sequence.

17. A method of producing at least a portion of a delta chain of the T cell antigen receptor polypeptide which comprises expressing the DNA sequence of claim 16 in a suitable host, the DNA sequence being part of an expression construct adapted for expression of the DNA sequence in the host.

18. The nucleotide sequence of claim 13 in which the T cell antigen receptor polypeptide is a human T cell antigen receptor polypeptide.

19. A substantially pure nucleotide sequence comprising a portion of a second nucleotide sequence, which second nucleotide sequence is substantially as shown in FIG. 15, which portion encodes a joining region of a delta chain of a T cell antigen receptor polypeptide.

20. The substantially pure nucleotide sequence of claim 19 in which, when the second nucleotide sequence is expressed in a host cell which glycosylates the delta chain of the T cell antigen receptor, the glycosylated delta chain of the T cell antigen receptor encoded by the second nucleotide sequence has a molecular weight of about 40,000 as determined by denaturing polyacrylamide gel electrophoresis.

21. The substantially pure nucleotide sequence of claim 19 in which the second nucleotide sequence encodes a delta chain of the T cell antigen receptor comprising an unglycosylated protein core having a molecular weight of about 31,000.

22. The substantially pure nucleotide sequence of claim 19 which is a DNA sequence.

23. A method of producing at least a portion of a delta chain of the T cell antigen receptor polypeptide which comprises expressing the DNA sequence of claim 22 in a suitable host, the DNA sequence being part of an expression construct adapted for expression of the DNA sequence in the host.

24. The nucleotide sequence of claim 19 in which the T cell antigen receptor polypeptide is a human T cell antigen receptor polypeptide.

25. A substantially pure nucleotide sequence comprising a portion of a second nucleotide sequence, which second nucleotide sequence is substantially as shown in FIG. 15, which portion encodes a constant region of a delta chain of a T cell antigen receptor polypeptide.

26. The substantially pure nucleotide sequence of claim 25 in which, when the second nucleotide sequence is expressed in a host cell which glycosylates the delta chain of the T cell antigen receptor, the glycosylated delta chain of the T cell antigen receptor encoded by the second nucleotide sequence has a molecular weight of about 40,000 as determined by denaturing polyacrylamide gel electrophoresis.

27. The substantially pure nucleotide sequence of claim 25 in which the second nucleotide sequence encodes a delta chain of the T cell antigen receptor comprising an unglycosylated protein core having a molecular weight of about 31,000.

28. The substantially pure nucleotide sequence of claim 25 which is a DNA sequence.

29. A method of producing at least a portion of the delta chain of the T cell antigen receptor polypeptide which comprises expressing the DNA sequence of claim 28 in a suitable host, the DNA sequence being part of an expression construct adapted for expression of the DNA sequence to the host.

30. The nucleotide sequence of claim 25 in which the T cell antigen receptor polypeptide is a human T cell antigen receptor polypeptide.

31. A substantially pure nucleotide sequence encoding a delta chain of a T cell antigen receptor, which chain (a) is of a form capable of being found associated in a complex with the T3 antigen on the surface of a T cell, (b) is not reactive with antibodies to the alpha or beta chain of the T cell antigen receptor, and (c) is not reactive with antibodies to the gamma chain of the T cell antigen receptor.

32. The nucleotide sequence of claim 31 which, when expressed in a host cell which glycosylates the delta chain of the T cell antigen receptor, the delta chain of the T cell antigen receptor encoded by the nucleotide sequence has a molecular weight of about 40,000 as determined by denaturing polyacrylamide gel electrophoresis.

33. The nucleotide sequence of claim 31 in which the delta chain of the T cell antigen receptor encoded by the nucleotide sequence comprises an unglycosylated protein core having a molecular weight of about 31,000.

34. The nucleotide sequence of claim 31 in which the nucleotide sequence encodes a delta chain of a human T cell antigen receptor.

35. A portion of the nucleotide sequence of claim 31, 32, 33 or 34 encoding the variable region of the delta chain.

36. A portion of the nucleotide sequence of claim 31, 32, 33 or 34 encoding the joining region of the delta chain.

37. A portion of the nucleotide sequence of claim 31, 32, 33 or 34 encoding the constant region of the delta chain.

38. A nucleotide sequence comprising the portion of claim 35.

39. A nucleotide sequence comprising the portion of claim 36.

40. A nucleotide sequence comprising the portion of claim 37.

41. A substantially pure nucleotide sequence encoding a delta chain of a T cell antigen receptor polypeptide, or antigenic fragment thereof, which reacts with the monoclonal antibody δTCAR-3 produced by hybridoma δTCAR-3 deposited with the American Type Culture Collection and assigned accession number HB 9578.

42. A substantially pure nucleotide sequence encoding a delta chain of a T cell antigen receptor polypeptide, or antigenic fragment thereof, which reacts with the monoclonal antibody anti-TCRδ1 produced by the hybridoma 5A6.E9 as deposited with the American Type Culture Collection and assigned accession number HB 9772.

43. A substantially pure nucleotide sequence encoding a delta chain of a T cell antigen receptor polypeptide, which chain (a) is of a form capable of being found associated in a complex with the T3 antigen on the surface of a T cell, and (b) has a molecular weight of about 40,000 as determined by denaturing polyacrylamide gel electrophoresis.

44. A portion of the nucleotide sequence of claim 43 encoding the variable region of the delta chain.

45. A portion of the nucleotide sequence of claim 43 encoding the joining region of the delta chain.

46. A portion of the nucleotide sequence of claim 43 encoding the constant region of the delta chain.

47. The nucleotide sequence of claim 43 in which the T cell antigen receptor polypeptide is human.

* * * * *